(12) United States Patent
Lagu et al.

(10) Patent No.: US 6,218,390 B1
(45) Date of Patent: Apr. 17, 2001

(54) MORPHOLINONE AND MORPHOLINE DERIVATIVES AND USES THEREOF

(75) Inventors: Bharat Lagu, Maywood; Dhanapalan Nagarathnam, Ramsey; Dake Tian, Plainsboro, all of NJ (US); Charles Gluchowski, Danville, CA (US)

(73) Assignee: Synaptic Pharmaceutical Corporation, Paramus, NJ (US)

( * ) Notice: Subject to any disclaimer, the term of this patent is extended or adjusted under 35 U.S.C. 154(b) by 0 days.

(21) Appl. No.: 09/213,539

(22) Filed: Dec. 17, 1998

(51) Int. Cl.[7] .................. A61K 31/5375; C07D 265/28; C07D 265/32; C07D 295/00
(52) U.S. Cl. .................... 514/237.5; 514/238.2; 514/231.5; 544/98; 544/99; 544/111; 544/159; 544/176; 544/106; 544/162; 544/173; 544/175
(58) Field of Search .................... 544/111, 106, 544/162, 173, 175, 176, 56, 58.2, 358, 384, 98, 99, 159; 514/302, 301, 249, 231.5, 231.8, 232.8, 237.5, 238.2

(56) References Cited

U.S. PATENT DOCUMENTS

| | | | |
|---|---|---|---|
| 5,574,030 | 11/1996 | Masaki et al. | 514/212 |
| 5,719,149 | * 2/1998 | Finke et al. | 514/231.8 |

FOREIGN PATENT DOCUMENTS

| | | | |
|---|---|---|---|
| 577394 | * | 1/1994 | (EP) . |
| 9410989 | * | 1/1994 | (WO) . |

OTHER PUBLICATIONS

J.Phar.&Expt. Ther.242,326(1987)"Alpha–1Adrenoceptores in Hum.Prostate" S.Yamada et al., Jan. 1987.*
Europ.J.Phar.172,131(1989)"(+)–Niguldipine binds with very hifh affi.to Ca2+"R.Boer et al., Jan. 1989.*
Mol.Pharm.45,703(1994)"The alpha–1–Adrenergic Rec.that Mediates . . . "C.Forray et al., Jan. 1987.*

* cited by examiner

Primary Examiner—Mukund J. Shah
Assistant Examiner—Sudhaker B. Patel
(74) Attorney, Agent, or Firm—John P. White; Cooper & Dunham LLP

(57) ABSTRACT

This invention is directed to morpholinone and morpholine derivatives which are selective antagonists for human $\alpha_{1a}$ receptors. This invention is also related to uses of these compounds for lowering intraocular pressure, inhibiting cholesterol synthesis, relaxing lower urinary tract tissue, the treatment of benign prostatic hyperplasia, impotency, cardiac arrhythmia, sympathetic mediated pain, migraine, and for the treatment of any disease where the antagonism of the $\alpha_{1a}$ receptor may be useful. The invention further provides a pharmaceutical composition comprising a therapeutically effective amount of the above-defined compounds and a pharmaceutically acceptable carrier.

43 Claims, 6 Drawing Sheets

Compound 18

Compound 20

Compound 17

Compound 19

Compound 21

MORPHOLINONE AND MORPHOLINE DERIVATIVES AND USES THEREOF

Throughout this application, various references are referred to within parentheses. Disclosures of these publications in their entireties are hereby incorporated by reference into this application to more fully describe the state of the art to which this invention pertains.

BACKGROUND OF THE INVENTION

The designation "$\alpha_{1a}$" is the appellation recently approved to the IUPHAR Nomenclature Committee for the previously designated "$\alpha_{1c}$" cloned subtype as outlined in the Pharmacological Reviews (Hieble, et al. (1995) *Pharmacological Reviews* 47: 267 270). The designation $\alpha_{1a}$ is used throughout this application and the supporting tables and figures to refer to this receptor subtype. At the same time, the receptor formerly designated $\alpha_{1a}$ was renamed $\alpha_{1d}$. The new nomenclature is used throughout this application. Stable cell lines expressing these receptors are described herein; however, these cell lines were deposited with the American Type Culture Collection (ATCC) under the old nomenclature (infra).

Benign Prostatic Hyperplasia (BPH), also called Benign Prostatic Hypertrophy, is a progressive condition which is characterized by a nodular enlargement of prostatic tissue resulting in obstruction of the urethra. This results in increased frequency of urination, nocturia, a poor urine stream, and hesitancy or delay in starting the urine flow. Chronic consequences of BPH can include hypertrophy of bladder smooth muscle, a decompensated bladder, and an increased incidence of urinary tract infection. The specific biochemical, histological, and pharmacological properties of the prostate adenoma leading to the bladder outlet obstruction are not yet known. However, the development of BPH is considered to be an inescapable phenomenon for the aging male population. BPH is observed in approximately 70% of males over the age of 70. Currently, in the United States, the method of choice for treating BPH is surgery (Lepor, H., *Urol. Clinics North Amer.*, 17: 651, 1990). Over 400,000 prostatectomies are performed annually (data from 1986). The limitations of surgery for treating BPH include the morbidity rate of an operative procedure in elderly men, persistence or recurrence of obstructive and irritative symptoms, as well as the significant cost of surgery. A medicinal alternative to surgery is clearly very desirable.

α-Adrenergic receptors (McGrath et al., *Med. Res. Rev.* 2, 407–533, 1989) are specific neuroreceptor proteins located in the peripheral and central nervous systems on tissues and organs throughout the body. These receptors are important switches for controlling many physiological functions and, thus, represent important targets for drug development. In fact, many α-adrenergic drugs have been developed over the past 40 years. Examples include clonidine, phenoxybenzamine and prazosin (for treatment of hypertension), naphazoline (a nasal decongestant), and apraclonidine (for treatment of glaucoma). α-adrenergic drugs can be broken down into two distinct classes: agonists (e.g., clonidine and naphazoline), which mimic the receptor activation properties of the endogenous neurotransmitter norepinephrine, and antagonists (e.g., pheoxybenzamine and prazosin), which act to block the effects of norepinephrine. Many of these drugs are effective, but also produce unwanted side effects (e.g., clonidine produces dry mouth and sedation in addition to its antihypertensive effects).

During the past 15 years, a more precise understanding of α-adrenergic receptors and their drugs has evolved through increased scientific scrutiny. Prior to 1977, only one α-adrenergic receptor was kown to exist. Between 1977 and 1988, it was accepted by the scientific community that at least two α-adrenergic receptors, $\alpha_1$ and $\alpha_3$, existed in the central and peripheral nervous systems. Since 1988, new techniques in molecular biology have led to the identification of at least six α-adrenergic receptors which exist throughout the central and peripheral nervous systems: $\alpha_{1a}$ (new nomenclature), $\alpha_{1b}$, $\alpha_{1d}$ (new nomenclature), $\alpha_{2a}$, $\alpha_{2b}$ and $\alpha_{2c}$ (Bylund, D. B., *FASEB J* 6: 832, 1992). In many cases, it is not known precisely which physiological responses in the body are controlled by each of these receptors. In addition, current α-adrenergic drugs are not selective for any particular α-adrenergic receptor. Many of these drugs produce untoward side effects that may be attributed to their poor α-adrenergic receptor selectivity.

Since the mid 1970's, nonselective α antagonists have been prescribed to treat BPH. In 1976, M. Caine et al. (*Brit. J. Urol.* 48: 955, 1976) reported that the nonselective α-antagonist phenoxybenzamine was useful in relieving the symptoms of BPH. This drug may produce its effects by interacting with α-receptors located on the prostate. However, this drug also produces significant side effects such as dizziness and aethenia, which severely limit its use in treating patients on a chronic basis. More recently, the α-adrenergic antagonists prazosin and torazosin have also been found to be useful for treating BPH. However, these drugs also produce untoward side effects. It has recently been discovered that the $\alpha_{1a}$ receptor is responsible for mediating the contraction of human prostate smooth muscle (Gluchowski, C. et al., WO 94/10989, 1994; Forray, C. et al., *Mol. Pharmacol.* 45: 703, 1994). This discovery indicates that the $\alpha_{1a}$ antagonists may be effective agents for the treatment of BPH with decreased side effects. Further studies have indicated that the $\alpha_{1a}$ receptor may also be present in other lower urinary tract tissues, such as urethral smooth muscle (Ford et al., *Br. J. Pharmacol.* 114; 24P, 1995).

SUMMARY OF THE INVENTION

This invention is directed to a compound having the structure:

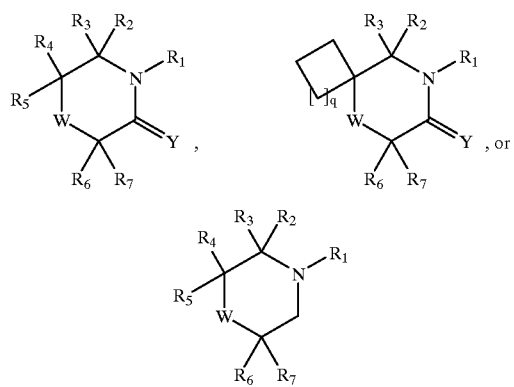

where W is O, S, or $NR_8$; wherein $R_8$ is independently H, straight chained or branched $C_1$–$C_7$ alkyl, straight chained or branched $C_2$–$C_7$ alkenyl or alkynyl, $C_3$–$C_7$ cycloalkyl, or $C_5$–$C_7$ cycloalkenyl;

where Y is independently O or S;

where $R_2$ is aryl or heteroaryl; wherein the aryl or heteroaryl may be substituted with one or more of F; Cl; Br; I; —CN; —NO$_2$; —N(R$_8$)$_2$; —SO$_2$R$_8$; —(CH$_2$)$_n$ C(Y)R$_8$; —(CH$_2$)$_n$YR$_8$; —(CH$_2$)$_n$C(Y)N(R$_8$)$_2$; —(CH$_2$)$_n$CO$_2$R$_8$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl; and wherein n independently is an integer from 0 to 7 inclusive;

where $R_3$ is independently H; straight chained or branched $C_1$–$C_7$ alkyl, monofluoroalkyl, or polyfluoroalkyl;

where $R_4$ is H, —(CH$_2$)$_t$YR$_8$, —(CH$_2$)$_t$C(Y)N(R$_8$)$_2$, —(CH$_2$)$_t$C(Y)R$_8$, —(CH$_2$)$_t$CO$_2$R$_8$, —(CH$_2$)$_t$N(R$_8$)$_2$, —(CH$_2$)$_t$CN, —C(Y)R$_8$, —C(Y)N(R$_8$)$_2$, —CO$_2$R$_8$, straight chained or branched $C_1$–$C_7$ alkyl, straight chained or branched $C_2$–$C_7$ alkenyl or alkynyl, $C_3$–$C_7$ cycloalkyl, $C_5$–$C_7$ cycloalkenyl, or phenyl or benzyl; wherein the phenyl or benzyl may be substituted with one or more of F; Cl; Br; I; —CN; —NO$_2$; —N(R$_8$)$_2$; —SO$_2$R$_8$; —(CH$_2$)$_n$C(Y) R$_8$; —(CH$_2$)$_n$YR$_8$; —(CH$_2$)$_n$C(Y)N(R$_8$)$_2$; —(CH$_2$)$_n$CO$_2$R$_8$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl; and wherein t independently is an integer from 1 to 4 inclusive;

where $R_5$ is H, —(CH$_2$)$_t$YR$_8$, —(CH$_2$)$_t$C(Y)N(R$_8$)$_2$, —(CH$_2$)$_t$C(Y)R$_8$, —(CH$_2$)$_t$CO$_2$R$_8$, —(CH$_2$)$_t$N(R$_8$)$_2$, —(CH$_2$)$_t$CN, straight chained or branched $C_1$–$C_7$ alkyl, straight chained or branched $C_2$–$C_7$ alkenyl or alkynyl, $C_3$–$C_7$ cycloalkyl, $C_5$–$C_7$ cycloalkenyl, or phenyl or benzyl; wherein the phenyl or benzyl may be substituted with one or more of F; Cl; Br; I; —CN; —NO$_2$; —N(R$_8$)$_2$; —SO$_2$R$_8$; —(CH$_2$)$_n$C(Y)R$_8$; —(CH$_2$)$_n$YR$_8$; —(CH$_2$)$_n$C(Y)N(R$_8$)$_2$; —(CH$_2$)$_n$CO$_2$R$_8$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

where $R_6$ is H, —(CH$_2$)$_t$YR$_8$, —(CH$_2$)$_t$C(Y)N(R$_8$)$_2$, —(CH$_2$)$_t$C(Y)R$_8$, —(CH$_2$)$_t$CO$_2$R$_8$, —(CH$_2$)$_t$N(R$_8$)$_2$, —(CH$_2$)$_t$CN, —C(Y)R$_8$, —C(Y)N(R$_8$)$_2$, —CO$_2$R$_8$, straight chained or branched $C_1$–$C_7$ alkyl, straight chained or branched $C_2$–$C_7$ alkenyl or alkynyl, $C_3$–$C_7$ cycloalkyl, $C_5$–$C_7$ cycloalkenyl, or phenyl or benzyl; wherein the phenyl or benzyl may be substituted with one or more of F; Cl; Br; I; —CN; —NO$_2$; —N(R$_8$)$_2$; —SO$_2$R$_8$; —(CH$_2$)$_n$C(Y)R$_8$; —(CH$_2$)$_n$YR$_8$; —(CH$_2$)$_n$C(Y)N(R$_8$)$_2$; —(CH$_2$)$_n$CO$_2$R$_8$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

where $R_7$ is H, —(CH$_2$)$_t$YR$_8$, —(CH$_2$)$_t$C(Y)N(R$_8$)$_2$, —(CH$_2$)$_t$C(Y)R$_8$, —(CH$_2$)$_t$CO$_2$R$_8$, —(CH$_2$)$_t$N(R$_8$)$_2$, —(CH$_2$)$_t$CN, straight chained or branched $C_1$–$C_7$ alkyl, straight chained or branched $C_2$–$C_7$ alkenyl or alkynyl, $C_3$–$C_7$ cycloalkyl, $C_5$–$C_7$ cycloalkenyl, or phenyl or benzyl; wherein the phenyl or benzyl may be substituted with one or more of F; Cl; Br; I; —CN; —NO$_2$; —N(R$_8$)$_2$; —SO$_2$R$_8$; —(CH$_2$)$_n$C(Y)R$_8$; —(CH$_2$)$_n$YR$_8$; —(CH$_2$)$_n$C(Y)N(R$_8$)$_2$; —(CH$_2$)$_n$CO$_2$R$_8$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

where q is an integer from 0 to 4 inclusive;

where each $R_8$, n, and t independently is as defined above;

where $R_1$ is

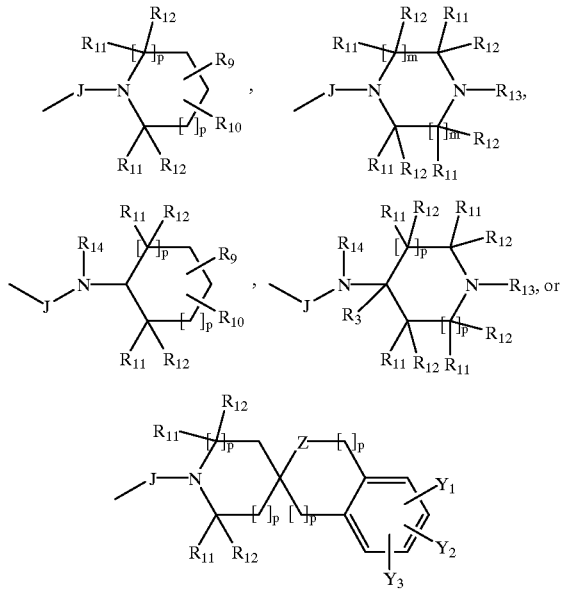

wherein each $R_9$ is H; straight chained or branched $C_1$–$C_7$ alkyl, hydroxyalkyl, aminoalkyl, alkoxyalkyl, monofluoroalkyl, or polyfluoroalkyl; straight chained or branched $C_2$–$C_7$ alkenyl or alkynyl; $C_3$–$C_7$ cycloalkyl, monofluorocycloalkyl, or polyfluorocycloalkyl; $C_5$–$C_7$ cycloalkenyl; or aryl or heteroaryl, wherein the aryl or heteroaryl may be substituted with one or more of F; Cl; Br; I; —(CH$_2$)$_n$YR$_8$; —(CH$_2$)$_n$C(Y)R$_8$; —(CH$_2$)$_n$C(Y)N(R$_8$)$_2$; —(CH$_2$)$_n$CO$_2$R$_8$; —CN; —NO$_2$; —N(R$_8$)$_2$; —SO$_2$R$_8$; straight chained or branched $C_1$–$C_7$ alkyl, monofluoroalkyl, or polyfluoroalkyl; straight chained or branched $C_2$–$C_7$ alkenyl or alkynyl; $C_3$–$C_7$ cycloalkyl, monofluorocycloalkyl, or polyfluorocycloalkyl; or $C_5$–$C_7$ cycloalkenyl;

wherein each $R_{10}$ is H; F; —OH; —(CH$_2$)$_n$C(Y)R$_8$; —(CH$_2$)$_n$YR$_8$; —(CH$_2$)$_n$C(Y)N(R$_8$)$_2$; (CH$_2$)$_n$CO$_2$R$_8$; —CN; —NO$_2$; —N(R$_8$)$_2$; aryl or heteroaryl; straight chained or branched $C_1$–$C_7$ alkyl, hydroxyalkyl, aminoalkyl, carboxamidoalkyl, alkoxyalkyl, monofluoroalkyl, or polyfluoroalkyl; straight chained or branched $C_2$–$C_7$ alkenyl or alkynyl; $C_3$–$C_7$ cycloalkyl, monofluorocycloalkyl, or polyfluorocycloalkyl; or $C_5$–$C_7$ cycloalkenyl; wherein the alkyl, hydroxyalkyl, alkoxyalkyl, aminoalkyl, carboxamidoalkyl, alkenyl, alkynyl, cycloalkyl or cycloalkenyl may be substituted with one or more aryl or heteroaryl; wherein the aryl or heteroaryl may be substituted with one or more of F; Cl; Br; I; —(CH$_2$)$_n$YR$_8$; —(CH$_2$)$_n$C(Y)R$_8$; —(CH$_2$)$_n$C(Y)N(R$_8$)$_2$; —(CH$_2$)$_n$CO$_2$R$_8$; —CN; —NO$_2$; —N(R$_8$)$_2$; —SO$_2$R$_8$; straight chained or branched $C_1$–$C_7$ alkyl, monofluoroalkyl, or polyfluoroalkyl; straight chained or branched $C_2$–$C_7$ alkenyl or alkynyl; $C_3$–$C_7$ cycloalkyl, monofluorocycloalkyl, or polyfluorocycloalkyl; or $C_5$–$C_7$ cycloalkenyl;

wherein each $R_{11}$ is independently H, —(CH$_2$)$_t$YR$_8$, —(CH$_2$)$_t$C(Y)N(R$_8$)$_2$, —(CH$_2$)$_t$C(Y)R$_8$, —(CH$_2$)$_t$ $CO_2R_8$, $-(CH_2)_tN(R_8)_2$, $-(CH_2)_tCN$, $-C(Y)R_8$, $-C(Y)N(R_8)_2$, $-CO_2R_8$, straight chained or branched $C_1-C_7$ alkyl, straight chained or branched $C_2-C_7$ alkenyl or alkynyl, $C_3-C_7$ cycloalkyl, or $C_5-C_7$ cycloalkenyl;

wherein each $R_{12}$ is independently H, $-(CH_2)_tYR_8$, $-(CH_2)_tC(Y)N(R_8)_2$, $-(CH_2)_tC(Y)R_8$, $-(CH_2)_tCO_2R_8$, $-(CH_2)_tN(R_8)_2$, $-(CH_2)_tCN$, straight chained or branched $C_1-C_7$ alkyl, straight chained or branched $C_2-C_7$ alkenyl or alkynyl, $C_3-C_7$ cycloalkyl or $C_5-C_7$ cycloalkenyl;

wherein $R_{13}$ is H, $C_1-C_7$ alkyl, $-C(O)R_2$, aryl, heteroaryl, $C_1-C_7$ alkyl substituted with one or two aryl, or $C_1-C_7$ alkyl substituted with one or two heteroaryl; wherein the aryl or heteroaryl may be substituted with one or more of F; Cl; Br; I; $-CN$; $-NO_2$; $-N(R_8)_2$; $-SO_2R_8$; $-(CH_2)_nC(Y)R_8$; $-(CH_2)_nYR_8$; $-(CH_2)_nC(Y)N(R_8)_2$; $-(CH_2)_nCO_2R_8$; straight chained or branched $C_1-C_7$ alkyl, monofluoroalkyl, polyfluoroalkyl, or carboxamidoalkyl; straight chained or branched $C_2-C_7$ aminoalkyl, alkenyl, or alkynyl; $C_3-C_7$ cycloalkyl; or $C_5-C_7$ cycloalkenyl;

wherein $R_{14}$ is H, straight chained or branched $C_1-C_7$ akyl;

wherein Z is O, S, $NR_{14}$, CO, $CH_2$,

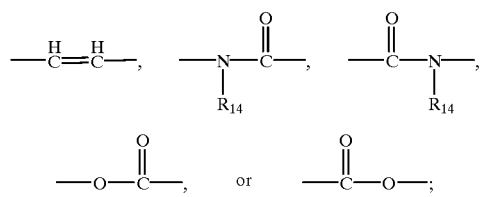

wherein $Y_1$, $Y_2$, and $Y_3$ independently are H; F; Cl; Br; I; $-CN$; $-NO_2$; $-N(R_8)_2$; $-SO_2R_8$; $-(CH_2)_nC(Y)R_8$; $-(CH_2)_nYR_8$; $-(CH_2)_nC(Y)N(R_8)_2$; $-(CH_2)_nCO_2R_8$; straight chained or branched $C_1-C_7$ alkyl, monofluoroalkyl, polyfluoroalkyl, aminoalkyl, or carboxamidoalkyl; straight chained or branched $C_2-C_7$ alkenyl or alkynyl; $C_3-C_7$ cycloalkyl; or $C_5-C_7$ cycloalkenyl;

wherein each m is independently 1 or 2;

wherein each p is independently an integer from 0 to 2 inclusive;

wherein J is

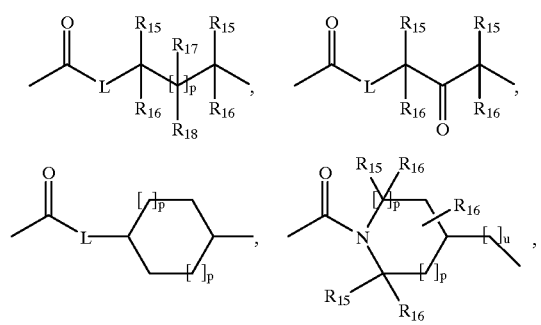

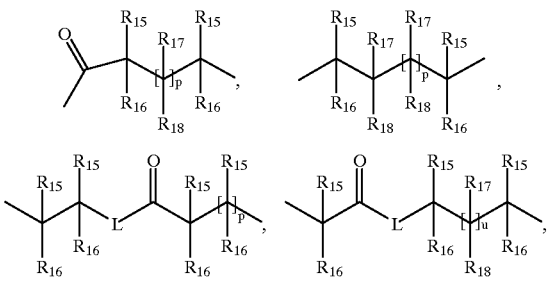

or $C_2-C_7$ alkenyl;

wherein each $R_{15}$ is independently H, $-(CH_2)_tYR_8$, $-(CH_2)_tC(Y)N(R_8)_2$, $-(CH_2)_tC(Y)R_8$, $-(CH_2)_tCO_2R_8$, $-(CH_2)_tN(R_8)_2$, $-(CH_2)_tCN$, $-C(Y)R_8$, $-C(Y)N(R_8)_2$, $-CO_2R_8$, straight chained or branched $C_1-C_7$ alkyl, straight chained or branched $C_2-C_7$ alkenyl or alkynyl, $C_3-C_7$ cycloalkyl, or $C_5-C_7$ cycloalkenyl;

wherein each $R_1$ is independently H, $-(CH_2)_tYR_8$, $-(CH_2)_tC(Y)N(R_8)_2$, $-(CH_2)_tC(Y)R_8$, $-(CH_2)_tCO_2R_8$, $-(CH_2)_tN(R_8)_2$, $-(CH_2)_tCN$, straight chained or branched $C_1-C_7$ alkyl, straight chained or branched $C_2-C_7$ alkenyl or alkynyl, $C_3-C_7$ cycloalkyl, or $C_5-C_7$ cycloalkenyl;

wherein each $R_{17}$ is independently H; F; $-(CH_2)_tYR_8$; $-(CH_2)_tC(Y)N(R_8)_2$; $-(CH_2)_tC(Y)R_8$; $-(CH_2)_tCO_2R_8$; $-(CH_2)_tN(R_8)_2$; $-(CH_2)_tCN$; $-C(Y)R_8$; $-C(Y)N(R_8)_2$; $-CO_2R_8$; straight chained or branched $C_1-C_7$ alkyl, monofluoroalkyl, polyfluoroalkyl, aminoalkyl, or carboxamidoalkyl; straight chained or branched $C_2-C_7$ alkenyl or alkynyl; $C_3-C_7$ cycloalkyl; or $C_5-C_7$ cycloalkenyl;

wherein each $R_{18}$ is independently H; F; $-(CH_2)_tYR_8$; $-(CH_2)_tC(Y)N(R_8)_2$; $-(CH_2)_tC(Y)R_8$; $-(CH_2)_tCO_2R_8$; $-(CH_2)_tN(R_8)_2$; $-(CH_2)_tCN$; straight chained or branched $C_1-C_7$ alkyl, monofluoroalkyl, polyfluoroalkyl, aminoalkyl, or carboxamidoalkyl; straight chained or branched $C_2-C_7$ alkenyl or alkynyl; $C_3-C_7$ cycloalkyl; or $C_5-C_7$ cycloalkenyl;

wherein L is S, O, or $N(R_8)$;

wherein u is an integer from 0 to 1 inclusive;

or a pharmaceutically acceptable salt thereof.

This invention provides for a pharmaceutical composition comprising a therapeutically effective amount of any one of the compounds described herein and a pharmaceutically acceptable carrier.

This invention provides for a method of treating a subject suffering from benign prostatic hyperplasia which comprises administering to the subject an amount of any one of the compounds described herein effective to treat benign prostatic hyperplasia.

This invention provides for a method of treating a subject suffering from high intraocular pressure which comprises administering to the subject an amount of any one of the compounds described herein effective to lower intraocular pressure.

This invention provides for a method of treating a subject suffering from a disorder associated with high cholesterol which comprises administering to the subject an amount of any one of the compounds described herein effective to inhibit cholesterol synthesis.

This invention provides for a method of treating a subject suffering from cardiac arrhythmia which comprises administering to the subject an amount of any one of the compounds described herein effective to treat cardiac arrhythmia.

This invention provides for a method of treating a subject suffering from impotency which comprises administering to the subject an amount of any one of the compounds described herein effective to treat impotency.

This invention provides for a method of treating a subject suffering from sympathetically mediated pain which comprises administering to the subject an amount of any one of the compounds described herein effective to treat sympathetically mediated pain.

This invention provides for a method of treating a subject suffering from migraine which comprises administering to the subject an amount of any one of the compounds described herein effective to treat migraine.

This invention provides for a method of treating a disease which is susceptible to treatment by antagonism of the $\alpha_{1a}$ receptor which comprises administering to the subject an amount of any one of the compounds described herein effective to treat the disease.

This invention provides for a method of treating a subject suffering from benign prostatic hyperplasia which comprises administering to the subject an amount of any one of the compounds described herein in combination with a 5-alpha reductase inhibitor effective to treat benign prostatic hyperplasia.

This invention provides for a pharmaceutical composition comprising a therapeutically effective amount of any one of the compounds described herein in combination with a therapeutically effective amount of finasteride and a pharmaceutically acceptable carrier.

This invention provides for a method of relaxing lower urinary tract tissue which comprises contacting the lower urinary tract tissue with an amount of any one of the compounds described herein effective to relax lower urinary tract tissue.

This invention provides for a method of relaxing lower urinary tract tissue in a subject which comprises administering to the subject an amount of any one of the compounds described herein effective to relax lower urinary tract tissue.

This invention provides for a pharmaceutical composition made by combining a therapeutically effective amount of any one of the compounds described herein and a pharmaceutically acceptable carrier.

This invention provides for a pharmaceutical composition made by combining a therapeutically effective amount of any one of the compounds described herein with a therapeutically effective amount of finasteride and a pharmaceutically acceptable carrier.

This invention provides for a process for making a pharmaceutical composition comprising combining a therapeutically effective amount of any one of the compounds described herein and a pharmaceutically acceptable carrier.

This invention provides for a process for making a pharmaceutical composition comprising combining a therapeutically effective amount of any one of the compounds described herein with a therapeutically effective amount of finasteride and a pharmaceutically acceptable carrier.

BRIEF DESCRIPTION OF THE FIGURES

FIGS. 1A–1F show the structures of the compounds described herein in the Examples.

DETAILED DESCRIPTION OF THE INVENTION

Figure 1A:
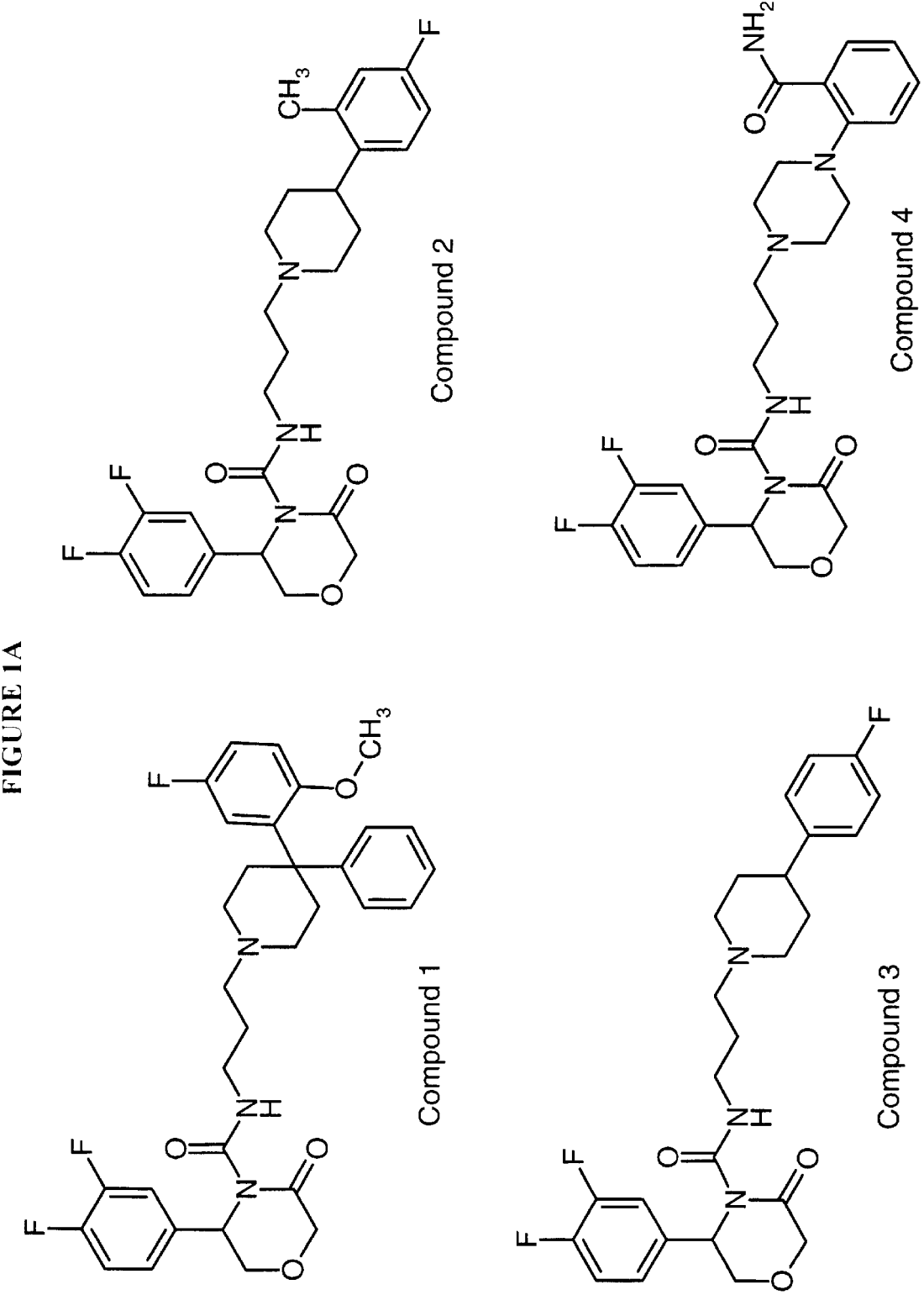
FIGS. 1A–1F
Figure 1B:
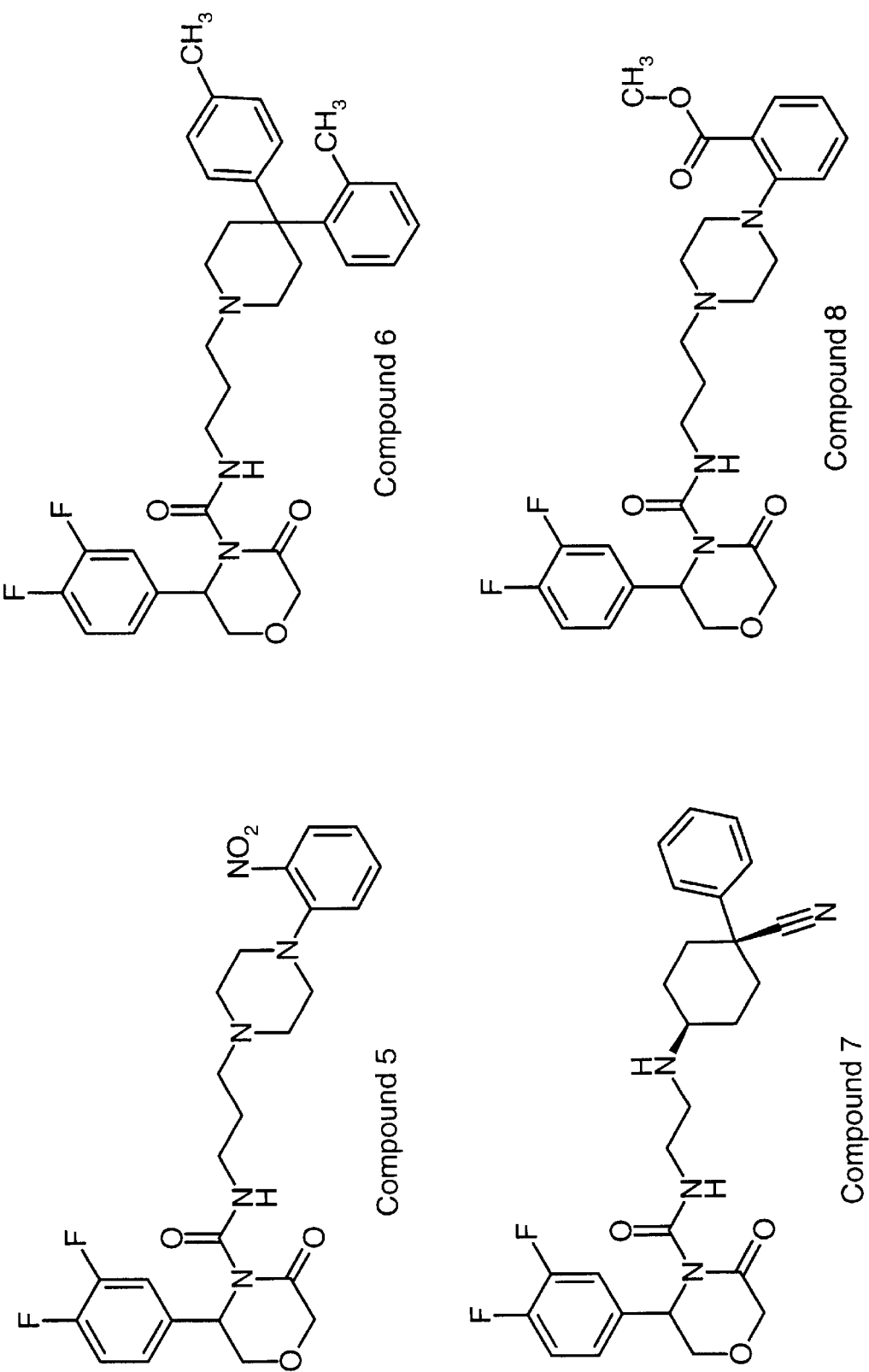
Figure 1C:
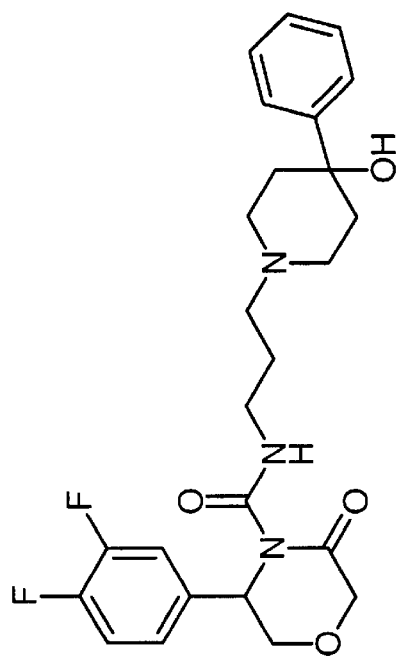
Figure 1C:
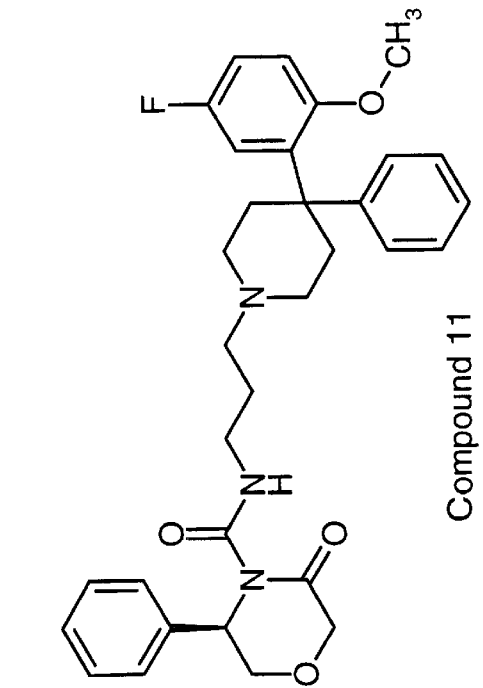
Figure 1C:
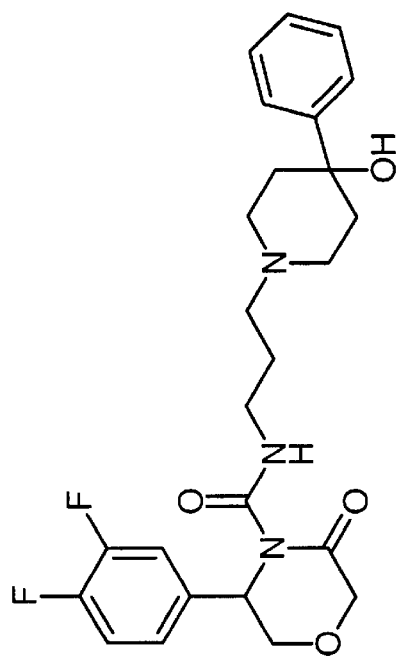
Figure 1C:
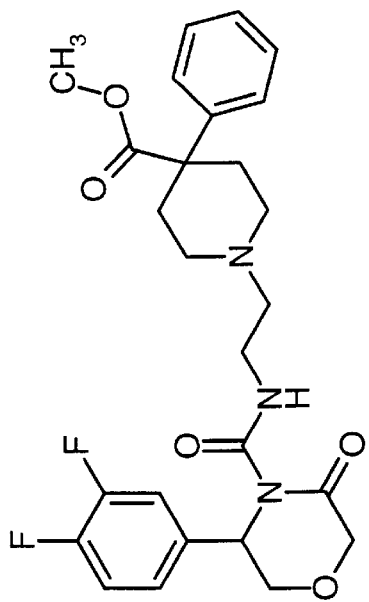
Figure 1C:
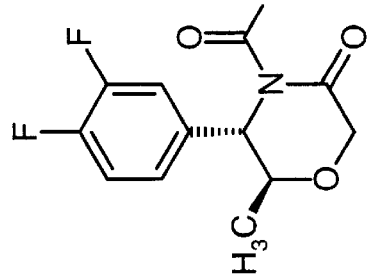
Figure 1D:
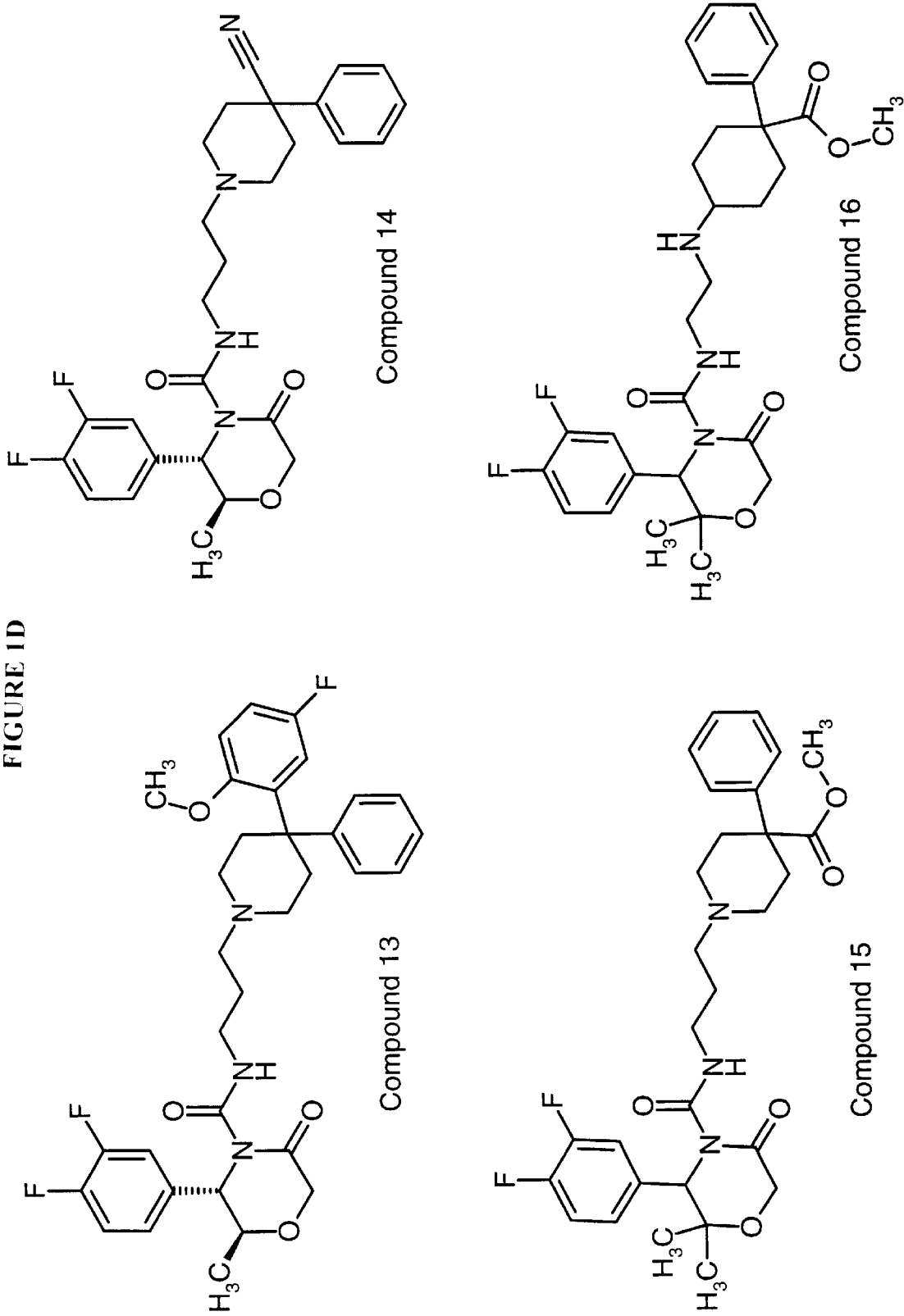
Figure 1E:
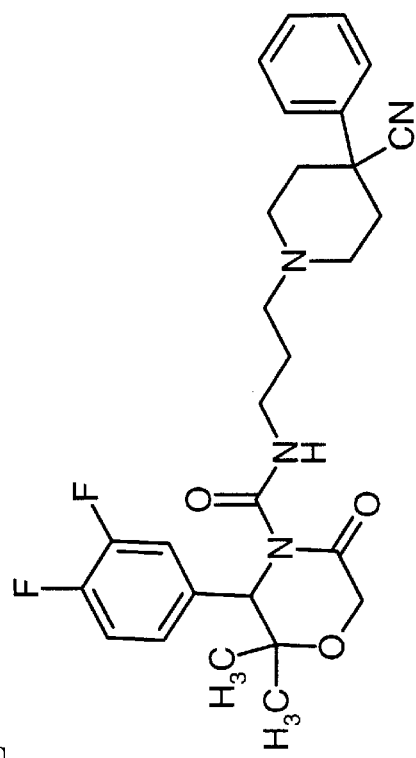
Figure 1E:
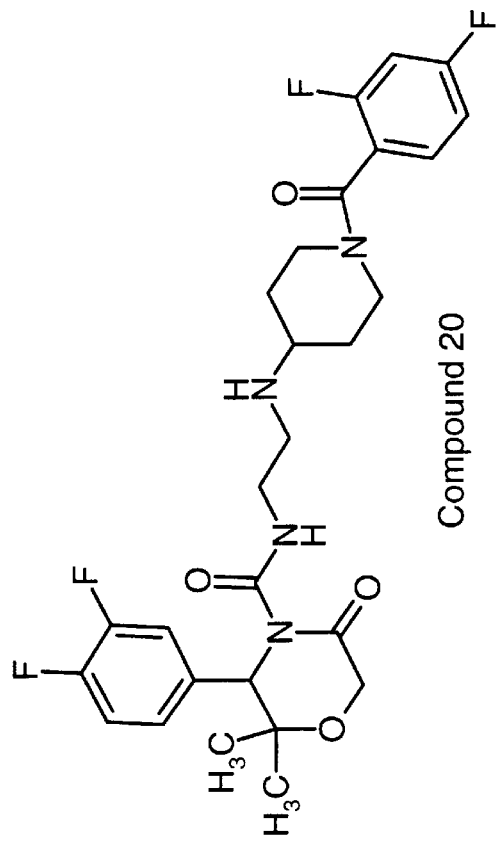
Figure 1E:
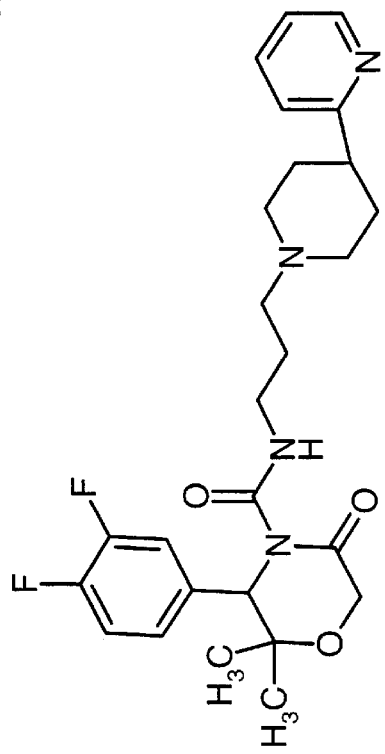
Figure 1E:
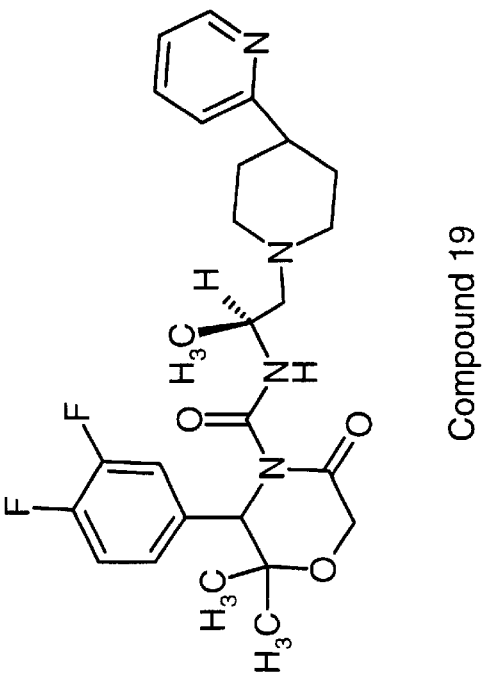
Figure 1F:
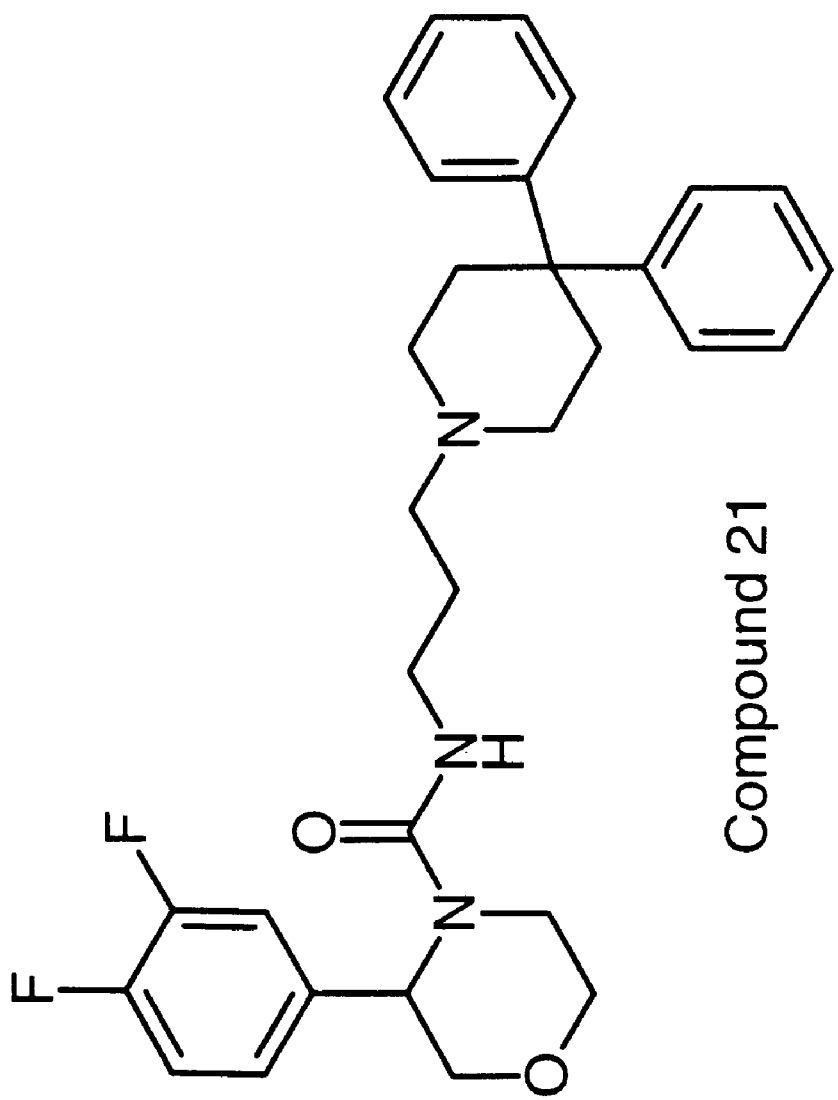

This invention provides for a compound having the structure:

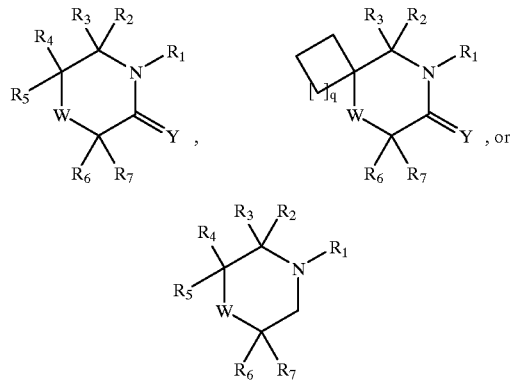

where W is O, S, or $NR_8$; wherein $R_8$ is independently H, straight chained or branched $C_1$–$C_7$ alkyl, straight chained or branched $C_2$–$C_7$ alkenyl or alkynyl, $C_3$–$C_7$ cycloalkyl, or $C_5$–$C_7$ cycloalkenyl;

where Y is independently O or S;

where $R_2$ is aryl or heteroaryl; wherein the aryl or heteroaryl may be substituted with one or more of F; Cl; Br; I; —CN; —$NO_2$; —$N(R_8)_2$; —$SO_2R_8$; —$(CH_2)_n$ $C(Y)R_8$; —$(CH_2)_nYR_8$; —$(CH_2)_nC(Y)N(R_8)_2$; —$(CH_2)_nCO_2R_8$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl; and wherein n independently is an integer from 0 to 7 inclusive;

where $R_3$ is independently H; straight chained or branched $C_1$–$C_7$ alkyl, monofluoroalkyl, or polyfluoroalkyl;

where $R_4$ is H, —$(CH_2)_tYR_8$, —$(CH_2)_tC(Y)N(R_8)_2$, —$(CH_2)_tC(Y)R_8$, —$(CH_2)_tCO_2R_8$, —$(CH_2)_tN(R_8)_2$, —$(CH_2)_tCN$, —$C(Y)R_8$, —$C(Y)N(R_8)_2$, —$CO_2R_8$ straight chained or branched $C_1$–$C_7$ alkyl, straight chained or branched $C_2$–$C_7$ alkenyl or alkynyl, $C_3$–$C_7$ cycloalkyl, $C_5$–$C_7$ cycloalkenyl, or phenyl or benzyl; wherein the phenyl or benzyl may be substituted with one or more of F; Cl; Br; I; —CN; —$NO_2$; —$N(R_8)_2$; —$SO_2R_8$; —$(CH_2)_nC(Y)R_8$; —$(CH_2)_nYR_8$; —$(CH_2)_nC(Y)N(R_8)_2$; —$(CH_2)_nCO_2R_8$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl; and wherein t independently is an integer from 1 to 4 inclusive;

where $R_5$ is H, —$(CH_2)_tYR_8$, —$(CH_2)_tC(Y)N(R_8)_2$, —$(CH_2)_tC(Y)$ $R_8$, —$(CH_2)_tCO_2R_8$, —$(CH_2)_tN(R_8)_2$, —$(CH_2)_tCN$, straight chained or branched $C_1$–$C_7$ alkyl, straight chained or branched $C_2$–$C_7$ alkenyl or alkynyl, $C_3$–$C_7$ cycloalkyl, $C_5$–$C_7$ cycloalkenyl, or phenyl or benzyl; wherein the phenyl or benzyl may be substituted with one or more of F; Cl; Br; I; —CN; —$NO_2$; —$N(R_8)_2$; —$SO_2R_8$; —$(CH_2)_nC(Y)R_8$; —$(CH_2)_nYR_8$; —$(CH_2)_nC(Y)N(R_8)_2$; —$(CH_2)_nCO_2R_8$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

where $R_6$ is H, $-(CH_2)_tYR_8$, $-(CH_2)_tC(Y)N(R_8)_2$, $-(CH_2)_tC(Y)R_8$, $-(CH_2)_tCO_2R_8$, $-(CH_2)_tN(R_8)_2$, $-(CH_2)_tCN$, $-C(Y)R_8$, $-C(Y)N(R_8)_2$, $-CO_2R_8$, straight chained or branched $C_1-C_7$ alkyl, straight chained or branched $C_2-C_7$ alkenyl or alkynyl, $C_3-C_7$ cycloalkyl, $C_5-C_7$ cycloalkenyl, or phenyl or benzyl; wherein the phenyl or benzyl may be substituted with one or more of F; Cl; Br; I; $-CN$; $-NO_2$; $-N(R_8)_2$; $-SO_2R_8$; $-(CH_2)_nC(Y)R_8$; $-(CH_2)_nYR_8$; $-(CH_2)_nC(Y)N(R_8)_2$; $-(CH_2)_nCO_2R_8$; straight chained or branched $C_1-C_7$ alkyl, monofluoroalkyl, polyfluoroalkyl, aminoalkyl, or carboxamidoalkyl; straight chained or branched $C_2-C_7$ alkenyl or alkynyl; $C_3-C_7$ cycloalkyl; or $C_5-C_7$ cycloalkenyl;

where $R_7$ is H, $-(CH_2)_tYR_8$, $-(CH_2)_tC(Y)N(R_8)_2$, $-(CH_2)_tC(Y)R_8$, $-(CH_2)_tCO_2R_8$, $-(CH_2)_tN(R_8)_2$, $-(CH_2)_tCN$, straight chained or branched $C_1-C_7$ alkyl, straight chained or branched $C_2-C_7$ alkenyl or alkynyl, $C_3-C_7$ cycloalkyl, $C_5-C_7$ cycloalkenyl, or phenyl or benzyl; wherein the phenyl or benzyl may be substituted with one or more of F; Cl; Br; I; $-CN$; $-NO_2$; $-N(R_8)_2$; $-SO_2R_8$; $-(CH_2)_nC(Y)R_8$; $-(CH_2)_nYR_8$; $-(CH_2)_nC(Y)N(R_8)_2$; $-(CH_2)_nCO_2R_8$; straight chained or branched $C_1-C_7$ alkyl, monofluoroalkyl, polyfluoroalkyl, aminoalkyl, or carboxamidoalkyl; straight chained or branched $C_2-C_7$ alkenyl or alkynyl; $C_3-C_7$ cycloalkyl; or $C_5-C_7$ cycloalkenyl;

where q is an integer from 0 to 4 inclusive;

where each $R_8$, n, and t independently is as defined above;

where $R_1$ is

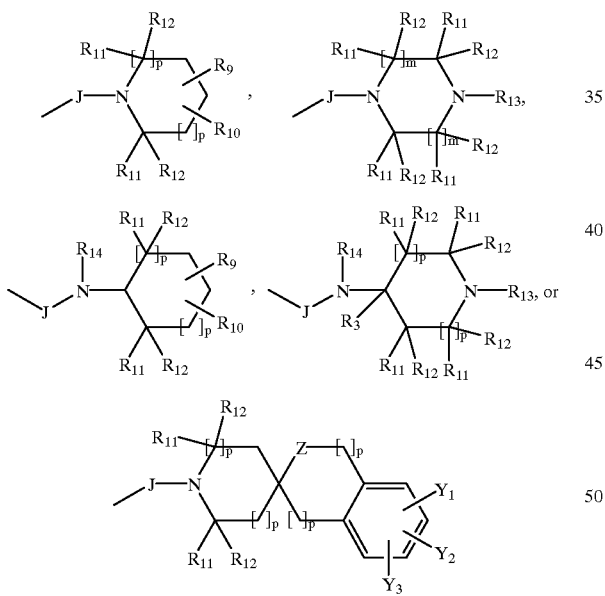

wherein each $R_9$ is H; straight chained or branched $C_1-C_7$ alkyl, hydroxyalkyl, aminoalkyl, alkoxyalkyl, monofluoroalkyl, or polyfluoroalkyl; straight chained or branched $C_2-C_7$ alkenyl or alkynyl; $C_3-C_7$ cycloalkyl, monofluorocycloalkyl, or polyfluorocycloalkyl; $C_5-C_7$ cycloalkenyl; or aryl or heteroaryl; wherein the aryl or heteroaryl may be substituted with one or more of F; Cl; Br; I; $-(CH_2)_nYR_8$; $-(CH_2)_nC(Y)R_8$; $-(CH_2)_nC(Y)N(R_8)_2$; $-(CH_2)_nCO_2R_8$; $-CN$; $-NO_2$; $-N(R_8)_2$; $-SO_2R_8$; straight chained or branched $C_1-C_7$ alkyl, monofluoroalkyl, or polyfluoroalkyl; straight chained or branched $C_2-C_7$ alkenyl or alkynyl; $C_3-C_7$ cycloalkyl, monofluorocycloalkyl, or polyfluorocycloalkyl; or $C_5-C_7$ cycloalkenyl;

wherein each $R_{10}$ is H; F; $-OH$; $-(CH_2)_nC(Y)R_8$; $-(CH_2)_nYR_8$; $-(CH_2)_nC(Y)N(R_8)_2$; $(CH_2)_nCO_2R_8$; $-CN$; $-NO_2$; $-N(R_8)_2$; aryl or heteroaryl; straight chained or branched $C_1-C_7$ alkyl, hydroxyalkyl, aminoalkyl, carboxamidoalkyl, alkoxyalkyl, monofluoroalkyl, or polyfluoroalkyl; straight chained or branched $C_2-C_7$ alkenyl or alkynyl; $C_3-C_7$ cycloalkyl, monofluorocycloalkyl, or polyfluorocycloalkyl; or $C_5-C_7$ cycloalkenyl; wherein the alkyl, hydroxyalkyl, alkoxyalkyl, aminoalkyl, carboxamidoalkyl, alkenyl, alkynyl, cycloalkyl or cycloalkenyl may be substituted with one or more aryl or heteroaryl; wherein the aryl or heteroaryl may be substituted with one or more of F; Cl; Br; I; $-(CH_2)_nYR_8$; $-(CH_2)_nC(Y)R_8$; $-(CH_2)_nC(Y)N(R_8)_2$; $-(CH_2)_nCO_2R_8$; $-CN$; $-NO_2$; $-N(R_8)_2$; $-SO_2R_8$; straight chained or branched $C_1-C_7$ alkyl, monofluoroalkyl, or polyfluoroalkyl; straight chained or branched $C_2-C_7$ alkenyl or alkynyl; $C_3-C_7$ cycloalkyl, monofluorocycloalkyl, or polyfluorocycloalkyl; or $C_5-C_7$ cycloalkenyl;

wherein each $R_{11}$ is independently H, $-(CH_2)_tYR_8$, $-(CH_2)_tC(Y)N(R_8)_2$, $-(CH_2)_tC(Y)R_8$, $-(CH_2)_tCO_2R_8$, $-(CH_2)_tN(R_8)_2$, $-(CH_2)_tCN$, $-C(Y)R_8$, $-C(Y)N(R_8)_2$, $-C_2R_8$, straight chained or branched $C_1-C_7$ alkyl, straight chained or branched $C_2-C_7$ alkenyl or alkynyl, $C_3-C_7$ cycloalkyl, or $C_5-C_7$ cycloalkenyl;

wherein each $R_{12}$ is independently H, $-(CH_2)_tYR_8$, $-(CH_2)_tC(Y)N(R_8)_2$, $-(CH_2)_tC(Y)R_8$, $-(CH_2)_tCO_2R_8$, $-(CH_2)_tN(R_8)_2$, $-(CH_2)_tCN$, straight chained or branched $C_1-C_7$ alkyl, straight chained or branched $C_2-C_7$ alkenyl or alkynyl, $C_3-C_7$ cycloalkyl or $C_5-C_7$ cycloalkenyl;

Q wherein $R_{13}$ is H, $C_1-C_7$ alkyl, $-C(O)R_2$, aryl, heteroaryl, $C_1-C_7$ alkyl substituted with one or two aryl, or $C_1-C_7$ alkyl substituted with one or two heteroaryl; wherein the aryl or heteroaryl may be substituted with one or more of F; Cl; Br; I; $-CN$; $-NO_2$; $-N(R_8)_2$; $-SO_2R_8$; $-(CH_2)_nC(Y)R_8$; $-(CH_2)_nYR_8$; $-(CH_2)_nC(Y)N(R_8)_2$; $-(CH_2)_nCO_2R_8$; straight chained or branched $C_1-C_7$ alkyl, monofluoroalkyl, polyfluoroalkyl, or carboxamidoalkyl; straight chained or branched $C_2-C_7$ aminoalkyl, alkenyl, or alkynyl; $C_3-C_7$ cycloalkyl; or $C_5-C_7$ cycloalkenyl;

wherein $R_{14}$ is H, straight chained or branched $C_1-C_7$ akyl;

wherein Z is O, S, $NR_{14}$, CO, $CH_2$,

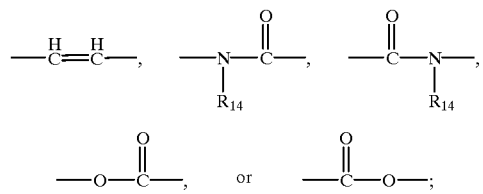

wherein $Y_1$, $Y_2$, and $Y_3$ independently are H; F; Cl; Br; I; $-CN$; $-NO_2$; $-N(R_8)_2$; $-SO_2R_8$; $-(CH_2)_nC(Y)R_8$; $-(CH_2)_nYR_8$; $-(CH_2)_nC(Y)N(R_8)_2$; $-(CH_2)_nCO_2R_8$; straight chained or branched $C_1-C_7$ alkyl, monofluoroalkyl, polyfluoroalkyl, aminoalkyl, or carboxamidoalkyl; straight chained or branched $C_2-C_7$ alkenyl or alkynyl; $C_3-C_7$ cycloalkyl; or $C_5-C_7$ cycloalkenyl;

wherein each m is independently 1 or 2;
wherein each p is independently an integer from 0 to 2 inclusive;
wherein J is

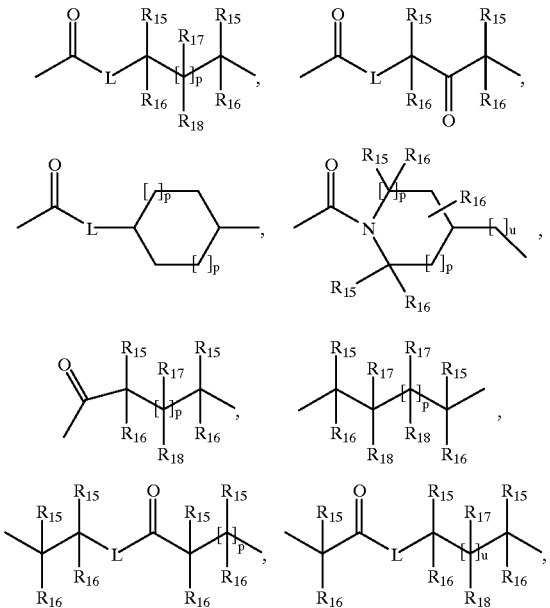

or $C_2$–$C_7$ alkenyl;

wherein each $R_{15}$ is independently H, —$(CH_2)_t YR_8$, —$(CH_2)_t C(Y)N(R_8)_2$, —$(CH_2)_t C(Y)R_8$, —$(CH_2)_t CO_2R_8$, —$(CH_2)_t N(R_8)_2$, —$(CH_2)_t CN$, —$C(Y)R_8$, —$C(Y)N(R_8)_2$, —$CO_2R_8$, straight chained or branched $C_1$–$C_7$ alkyl, straight chained or branched $C_2$–$C_7$ alkenyl or alkynyl, $C_3$–$C_7$ cycloalkyl, or $C_5$–$C_7$ cycloalkenyl;

wherein each $R_{16}$ is independently H, —$(CH_2)_t YR_8$, —$(CH_2)_t C(Y)N(R_8)_2$, —$(CH_2)_t C(Y)R_8$, —$(CH_2)_t CO_2R_8$, —$(CH_2)_t N(R_8)_2$, —$(CH_2)_t CN$, straight chained or branched $C_1$–$C_7$ alkyl, straight chained or branched $C_2$–$C_7$ alkenyl or alkynyl, $C_3$–$C_7$ cycloalkyl, or $C_5$–$C_7$ cycloalkenyl;

wherein each $R_{17}$ is independently H; F; —$(CH_2)_t YR_8$; —$(CH_2)_t C(Y)N(R_8)_2$; —$(CH_2)_t C(Y)R_8$; —$(CH_2)_t CO_2R_8$; —$(CH_2)_t N(R_8)_2$; —$(CH_2)_t CN$; —$C(Y)R_8$; —$C(Y)N(R_8)_2$; —$CO_2R_8$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

wherein each $R_{18}$ is independently H; F; —$(CH_2)_t YR_8$; —$(CH_2)_t C(Y)N(R_8)_2$; —$(CH_2)_t C(Y)R_8$; —$(CH_2)_t CO_2R_8$; —$(CH_2)_t N(R_8)_2$; —$(CH_2)_t CN$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

wherein L is S, O, or $N(R_8)$;
wherein u is an integer from 0 to 1 inclusive;
or a pharmaceutically acceptable salt thereof.

The invention also provides for the (−) and (+) enantiomers of all compounds of the subject application described herein.

The invention further provides for the cis and trans enantiomers of all of the compounds of the subject application described herein. It is noted herein that the terms "cis" and "trans" correspond to relative stereochemistry, as determined, for example, by NOE (Nuclear Overhauser Effect) experiments.

The compounds of the present invention are preferably at least 80% pure, more preferably at least 90% pure, and most preferably at least 95% pure.

In the present invention, the term "aryl" is used to include phenyl, benzyl, benzoyl, or naphthyl; and the term "heteroaryl" is used to include pyrazinyl, pyrrolyl, furanyl, thiophenyl, pyridyl, imidazolyl, indolyl, aminophenyl, benzamidyl, benzimidazolyl, benzfurazanyl, benzfuranyl, or quinolyl.

The compounds of this invention exhibit greater affinity, preferably at least ten-fold greater affinity, for the human $\alpha_{1a}$ receptor over the human $\alpha_{1b}$ or human $\alpha_{1d}$ receptors.

In one embodiment, W is O.
In another embodiment, J is

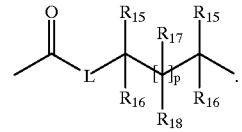

In another embodiment, $R_1$ is

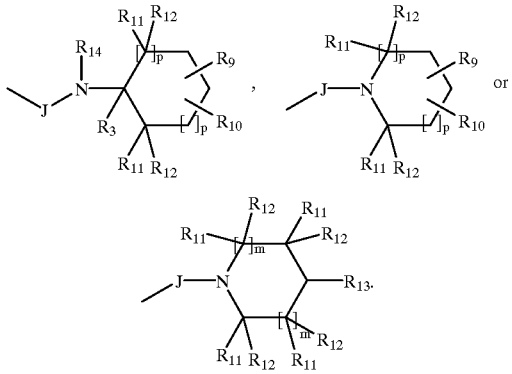

In another embodiment, $R_9$ is aryl or heteroaryl, wherein the aryl or heteroaryl may be substituted with one or more of F; Cl; Br; I; —$(CH_2)_n YR_8$; —$(CH_2)_n C(Y)R_8$; —$(CH_2)_n C(Y)N(R_8)_2$; —$(CH_2)_n CO_2R_8$; —CN; —$NO_2$; —$N(R_8)_2$; —$SO_2R_8$; straight chained or branched $C_1$–$C_7$ alkyl, monofluoroalkyl, or polyfluoroalkyl; and $R_{10}$ is H; —CN; —OH; —$CO_2R_9$; aryl or heteroaryl; wherein the aryl or heteroaryl may be substituted with one or more of F; Cl; Br; I; —$(CH_2)_n YR_8$; —$(CH_2)_n C(Y)R_8$; —$(CH_2)_n C(Y)N(R_8)_2$; —$(CH_2)_n CO_2R_8$; —CN; —$NO_2$; —$N(R_8)_2$; —$SO_2R_8$; straight chained or branched $C_1$–$C_7$ alkyl, monofluoroalkyl, or polyfluoroalkyl.

In another embodiment of the invention, the compound has the structure:

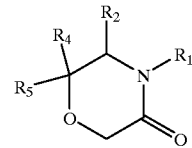

wherein $R_2$ is phenyl; wherein the phenyl may be substituted with one or more of F; Cl; Br; I; —CN; —$NO_2$; —$N(R_8)_2$;

—SO$_2$R$_8$; —(CH$_2$)$_n$C(Y)R$_8$; —(CH$_2$)$_n$YR$_8$; —(CH$_2$)$_n$C(Y)N(R$_8$)$_2$; —(CH$_2$)$_n$CO$_2$R$_8$; straight chained or branched C$_1$–C$_7$ alkyl, monofluoroalkyl, or polyfluoroalkyl.

In another embodiment, J is

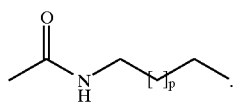

In another embodiment, R$_1$ is

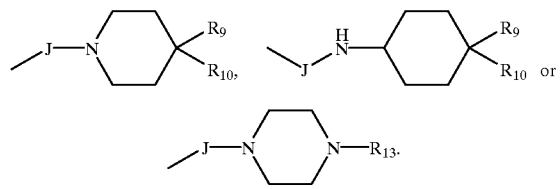

In another embodiment, R$_9$ is phenyl or pyridyl, wherein the phenyl or pyridyl may be substituted with one or more of F; Cl; Br; I; —(CH$_2$)$_n$YR$_8$; —(CH$_2$)$_n$C(Y)R$_8$; —(CH$_2$)$_n$C(Y)N(R$_8$)$_2$; —(CH$_2$)$_n$CO$_2$R$_8$; —CN; —NO$_2$; —N(R$_8$)$_2$; —SO$_2$R$_8$; straight chained or branched C$_1$–C$_7$ alkyl, monofluoroalkyl, or polyfluoroalkyl;

R$_{10}$ is H, —CN, —OH, —CO$_2$R$_8$, or phenyl; wherein the phenyl may be substituted with one or more of F; Cl; Br; I; —(CH$_2$)$_n$YR$_8$; —(CH$_2$)$_n$C(Y)R$_8$; —(CH$_2$)$_n$C(Y)N(R$_8$)$_2$; —(CH$_2$)$_n$CO$_2$R$_8$, —CN; —NO$_2$; —N(R$_8$)$_2$; —SO$_2$R$_8$; straight chained or branched C$_1$–C$_7$ alkyl, monofluoroalkyl, or polyfluoroalkyl; and R$_{13}$ is phenyl; wherein the phenyl may be substituted with one or more of F; Cl; Br; I; —CN; —NO$_2$; —N(R$_8$)$_2$; —SO$_2$R$_8$; —(CH$_2$)$_n$C(Y)R$_8$; —(CH$_2$)$_n$YR$_8$; —(CH$_2$)$_n$C(Y)N(R$_8$)$_2$; —(CH$_2$)$_n$CO$_2$R$_8$; straight chained or branched C$_1$–C$_7$ alkyl, monofluoroalkyl, polyfluoroalkyl, or carboxamidoalkyl; straight chained or branched C$_2$–C$_7$ aminoalkyl, alkenyl, or alkynyl; C$_3$–C$_7$ cycloalkyl; or C$_5$–C$_7$ cycloalkenyl.

In another preferred embodiment, the R$_4$ is H, alkyl, cycloalkyl, —CO$_2$R$_3$, or —C(Y)N(R$_3$)$_2$; and R$_{10}$ is H, F, C$_1$–C$_7$ alkyl, C$_1$–C$_7$ alkoxy, or OH.

The invention provides for a pharmaceutical composition comprising a therapeutically effective amount of any of the compounds described above and a pharmaceutically acceptable carrier. In the subject invention, a "therapeutically effective amount" is any amount of a compound which, when administered to a subject suffering from a disease against which the compounds are effective, causes reduction, remission, or regression of the disease.

In one embodiment, the therapeutically effective amount is an amount from about 0.01 mg per subject per day to about 800 mg per subject per day, preferably from about 0.01 mg per subject per day to about 500 mg per subject per day, more preferably from about 0.01 mg per subject per day to about 250 mg per subject per day, more preferably from about 0.1 mg per subject per day to about 60 mg per subject per day and most preferably from about 1 mg per subject per day to about 20 mg per subject per day. In the practice of this invention, the "pharmaceutically acceptable carrier" is any physiological carrier known to those of ordinary skill in the art useful in formulating pharmaceutical compositions.

In one embodiment the pharmaceutical carrier may be a liquid and the pharmaceutical composition would be in the form of a solution. In another embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes, and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The compound can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

In another embodiment, any one of the compounds described herein additionally does not cause a fall in blood pressure at dosages effective to alleviate benign prostatic hyperplasia.

The invention provides a method of treating a subject suffering from benign prostatic hyperplasia, which comprises administering to the subject any one of the compounds described herein effective to treat benign prostatic hyperplasia. In a preferred embodiment, the compound of the pharmaceutical composition additionally does not cause a fall in blood pressure at dosages effective to alleviate benign prostatic hyperplasia. In a preferred embodiment, the compound effects treatment of benign prostatic hyperplasia by relaxing lower urinary tract tissue and in particular where lower urinary tract tissue is prostatic smooth muscle.

In the practice of this invention, the term "lower urinary tract tissue" is used to include prostatic capsule, prostate urethra, urethral smooth muscle, prostatic smooth muscle, and bladderneck.

The invention further provides a method of treating a subject suffering from elevated intraocular pressure, which comprises administering to the subject one of the compounds described herein effective to lower intraocular pressure.

The invention further provides a method of treating a subject suffering from a disorder associated with elevated blood cholesterol, which comprises administering to the subject one of the compounds described herein effective to inhibit cholesterol synthesis.

The invention provides a method of treating a subject suffering from cardiac arrhythmia, which comprises administering to the subject one of the compounds described herein effective to treat cardiac arrhythmia.

The invention further provides a method of treating a subject suffering from impotency, which comprises administering to the subject one of the compounds described herein effective to treat impotency.

The invention further provides a method of treating a subject suffering from sympathetically mediated pain, which comprises administering to the subject one of the compounds described herein effective to treat sympathetically mediated pain.

This invention provides a method of treating a subject suffering from migraine which comprises administering to the subject one of the compounds described herein effective to treat migraine.

The invention also provides a method of treating a disease which is susceptible to treatment by antagonism of the $\alpha_{1a}$ receptor, which comprises administering to the subject one of the compounds described herein effective to treat the disease.

The invention provides a method of treating a subject suffering from benign prostatic hyperplasia, which comprises administering to the subject one of the compounds described herein in combination with a 5-alpha reductase inhibitor effective to treat benign prostatic hyperplasia. In one preferred embodiment the 5-alpha reductase inhibitor is finasteride.

This invention provides for a pharmaceutical composition comprising a therapeutically effective amount of any one of the compound described herein in combination with a therapeutically effective amount of finasteride and a pharmaceutically acceptable carrier. This invention also provides for a pharmaceutical composition comprising any one of the compounds described herein present in an amount from about 0.01 mg to about 800 mg and the therapeutically effective amount of the finasteride is about 5 mg. In one embodiment, the pharmaceutical composition is any one of the compounds described herein present in an amount from about 0.1 mg to about 60 mg and the therapeutically effective amount of finasteride is about 5 mg. In another embodiment, the pharmaceutical composition is any one of the compounds described herein present in an amount from about 1 mg to about 20 mg and the therapeutically effective amount of finasteride is about 5 mg.

The invention further provides a method of relaxing lower urinary tract tissue which comprises contacting the lower urinary tract tissue with an amount of one of the compounds described herein effective to relax lower urinary tract tissue. In one embodiment the lower urinary tract tissue is prostatic smooth muscle. In one preferred embodiment, the compound additionally does not cause a fall in blood pressure when it is effective to relax lower urinary tract tissue.

The invention provides a method of relaxing lower urinary tract tissue in a subject which comprises administering to the subject an amount of one of the compounds described herein effective to relax lower urinary tract tissue. In one embodiment the lower urinary tract tissue is prostatic smooth muscle. In one preferred embodiment, the compound additionally does not cause a fall in blood pressure when it is effective to relax lower urinary tract tissue.

This invention provides for a pharmaceutical composition made by combining a therapeutically effective amount of any one of the compounds described herein and a pharmaceutically acceptable carrier.

This invention provides for a pharmaceutical composition made by combining a therapeutically effective amount of any one of the compounds described herein with a therapeutically effective amount of finasteride and a pharmaceutically acceptable carrier.

This invention provides for a process for making a pharmaceutical composition comprising combining a therapeutically effective amount of any one of the compounds described herein and a pharmaceutically acceptable carrier.

This invention provides for a process for making a pharmaceutical composition comprising combining a therapeutically effective amount of any one of the compounds described herein with a therapeutically effective amount of finasteride and a pharmaceutically acceptable carrier.

Included in this invention are pharmaceutically acceptable salts and complexes of all of the compounds described herein. The salts include but are not limited to the following acids and bases: inorganic acids which include hydrochloric acid, hydrobromic acid, hydroiodic acid, sulfuric acid, and boric acid; organic acids which include acetic acid, oxalic acid, malonic acid, succinic acid, fumaric acid, tartaric acid, maleic acid, citric acid, methanesulfonic acid, benzoic acid, glycolic acid, lactic acid, and mandelic acid; inorganic bases which include ammonia; and organic bases which include methylamine, ethylamine, hydroxyethylamine, propylamine, dimethylamine, diethylamine, trimethylamine, triethylamine, ethylenediamine, hydroxyethylamine, morpholine, piperazine, and guanidine. This invention further provides for the hydrates and polymorphs of all of the compounds described herein.

The present invention includes within its scope prodrugs of the compounds of this inventions. In general, such prodrugs will be functional derivatives of the compounds of the invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, ed. H. Bundgaard, Elsevier, 1985.

The present invention further includes metabolites of the compounds of the present invention. Metabolites include active species produced upon introduction of compounds of this invention into the biological milieu.

One skilled in the art will readily appreciate that appropriate biological assays will be used to determine the therapeutic potential of the claimed compounds for the treating the above noted disorders.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

I. Synthesis of Morpholinone Examples (Schemes 1 and 2)

1. Synthesis of 3-(3,4-difluorophenyl)-5-oxo-morpholine-4-carboxylic acid-4-nitro-phenyl ester (Scheme 1)

a. 1-Hydroxy-(3,4-difluorophenyl)-acetophenone

To a solution of KOH (56 g, 1.0 mol) in MeOH (500 mL) was added 3,4-difluoroacetophenone (15.6 g, 0.1 mol) dropwise over 15 min at 0° C. Phenyliodosodiacetate (64.4 g, 0.2 mol) was added in small portions over a 20 min period, and the resulting yellow-orange solution was stirred overnight at room temperature. The solvent was removed in vacuo to obtain a yellow-orange gum. The residue was dissolved in 100 mL of water and 100 mL of brine and was thoroughly extracted with ethyl acetate (3×150 mL). The organic layer was dried over $Na_2SO_4$ and was decanted. The solvent was removed in vacuo to obtain 31.0 g of the acetal as thick yellow oil. It was dissolved in 200 mL of acetone and about 10 drops of concentrated sulfuric acid. The reaction mixture was stirred at room temperature for 2 hours until TLC analysis showed complete consumption of the starting material. The solvent was removed in vacuo and the solid that was obtained was first basified by adding saturated $NaHCO_3$ solution and then it was extracted with ethyl acetate (300 mL). The organic layer was separated and washed with brine. The organic layer was dried over $MgSO_4$, filtered, and the solvent was removed in vacuo to obtain a yellow solid. The yellow solid was washed with cold hexane (to remove iodobenzene impurities) and dried to obtain 11.4 g (66% yield) of 1-hydroxy-(3,4-difluorophenyl)-acetophenone as pale yellow solid. The product was shown to be >90% pure by NMR and was used in the next step without further purification.

b. 1-Hydroxy-(3,4-difluorophenyl)-acetophenone oxime

To a solution of 1-hydroxy-(3,4-difluorophenyl)-acetophenone (6.0 g, 34.9 mmol) in 150 mL of MeOH was added hydroxylamine hydrochloride (3.16 g, 45.6 mmol) and sodium acetate (9.6 g, 69.6 mmol) at room temperature and the resulting solution was stirred overnight. The solvent was removed and the residue was dissolved in methylene chloride (150 mL) and was washed with 100 mL of saturated $NaHCO_3$ solution followed by brine. The organic layer was separated and dried over $MgSO_4$, filtered, and the solvent was removed in vacuo to obtain 1-hydroxy-(3,4-difluorophenyl)-acetophenone-oxime as a yellow solid (5.6 g, 86%). It was used in the next step without any purification.

c. 2-Amino-2-(3,4-difluorophenyl)-ethanol

To a well stirred suspension of $LiAlH_4$ (3.4 g, 89.5 mmol) in THF (120 mL) in a 3-necked round bottom flask fitted with a condenser and a dropping funnel was added a solution of 1-hydroxy-(3,4-difluorophenyl)-acetophenone-oxime (4.6 g, 24.6 mmol) in THF (50 mL) dropwise at 0° C. The resulting greyish yellow suspension was heated to reflux for 2 hours. The reaction mixture was cooled to 0° C. and then carefully quenched sequentially with 3.4 mL of water, 3.4 mL of 3N NaOH, and 10 mL of water. The resulting suspension was filtered through a fritted glass funnel. To the residue was added 100 mL $Et_2O$ and the suspension was heated to reflux for 20 min. The suspension was filtered and was combined with the previous filtrate, dried over $MgSO_4$, filtered, and the solvent was removed in vacuo. 2-Amino-2-(3,4-difluorophenyl)-ethanol was obtained as a yellow glassy syrup (4.1 g, 96%) which was used in the next step without further purification.

Method A for the synthesis of 5-(3,4-difluoro-phenyl) morpholin-3-one:

d. 2-Chloro-N-[1-(3,4-difluoro-phenyl)-2-hydroxy-ethyl]-acetamide

To a solution of 2-amino-2-(3,4-difluorophenyl)-ethanol 2.6 g, 15.0 mmol) in $CH_2Cl_2$ (15 mL) and 20% (by wt.) NaOH (15 mL) was added a solution of chloroacetyl chloride (1.32 mL, 16.5 mmol) in 15 mL of $CH_2Cl_2$ at −10° C. dropwise under argon atmosphere. After the addition was complete, the reaction mixture was stirred for 15 min and then it was transferred to a separatory funnel. The organic layer was separated and the aqueous layer was extracted with $CH_2Cl_2$ (2×20 mL). The combined organic extracts were washed with a solution containing 10 mL of brine and 5 drops of concentrated HCl. The organic layer was dried over $MgSO_4$, filtered and the solvent was removed in vacuo to give a white solid. It was further purified with flash column chromatography on silica gel with 1:1 hexane/ EtOAc followed by EtOAc as the eluting system. 2-Chloro-N-[1-(3,4-difluorophenyl)-2-hydroxy-ethyl]-acetamide was obtained as a white solid (2.6 g, 69.5% yield).

e. 5-(3,4-Difluoro-phenyl)-morpholin-3-one

To a suspension of sodium hydride (0.29 g, 11.39 mmol) in 48 mL THF was added a solution of 2-chloro-N-[1-(3,4-difluoro-phenyl)-2-hydroxy-ethyl]-acetamide (2.6 g, 10.4 mmol) in 48 mL THF dropwise via a dropping funnel at −25° C. over 20 min. After the addition was over, the cooling bath was removed and the reaction mixture was stirred at room temperature for 8 hours. TLC analysis indicated a complete disappearance of the starting material. The reaction was quenched by adding a few crystals of ice. It was extracted thoroughly with EtOAc (3×30 mL) and was washed with brine. The organic layer was separated and dried over $MgSO_4$. The organic layer was filtered and the solvent was removed in vacuo. The residue was suspended in EtOAc and the white solid was collected via filtration which was found to be 5-(3,4-difluoro-phenyl)-morpholin-3-one (0.8 g, 38% yield).

Method B for the synthesis of 5-(3,4-difluoro-phenyl)-morpholin-3-one:

f. 5-(3,4-difluoro-phenyl)-morpholin-3-one

To a suspension of NaH (8.0 mmol, 0.19 g) in 10 mL THF at 0° C. was added a solution of 2-amino-2-(3,4-difluorophenyl)-ethanol (7.51 mmol, 1.3 g) in 20 mL THF dropwise via an addition funnel and after 30 min ethyl chloroacetate was added dropwise via syringe. The orange colored reaction mixture was stirred for 2 hours at 0° C. and then for 2 hours at 35° C. The solvent was removed and the 5-(3,4-difluoro-phenyl)-morpholin-3-one was isolated as a thick yellow oil (0.5 g). $^1$H NMR showed that the product was about 85% pure and any attempts to purify it further by column chromatography were not successful. It was used in the next reaction as described below without further purification.

g. 3-(3,4-Difluorophenyl)-5-oxo-morpholine-4-carboxylic acid-4-nitro-phenyl ester To a solution of 5-(3,4-difluoro-phenyl)-morpholin-3-one (0.34 g, 1.57 mmol) in 10 mL of THF was added NaH (0.05 g, 1.9 mmol) and the resulting solution was stirred for 30 min. It was then transferred via a syringe into a solution of 4-nitrophenyl chloroformate in 20 mL of anhydrous THF at −78° C. under argon. The resulting solution was stirred for 2 hours after which the solvent was removed and the residue was purified by column chromatography on silica gel with 1:1 hexane/$CH_2Cl_2$ followed by $CH_2Cl_2$ to obtain 3-(3,4-difluorophenyl)-5-oxo-morpholine-4-carboxylic acid-4-nitro-phenyl ester as a colorless thick oil (0.31 g, 51%).

2. Synthesis of (+)-3-(3,4-difluorophenyl)-5-oxo-morpholine-4-carboxylic acid-4-nitro-phenyl ester (Scheme 2)

a. [1-(3,4-Difluorophenyl)-2-hydroxy-ethyl]-carbamic acid-tert-butyl ester

To a solution of 2-amino-2-(3,4-difluorophenyl)-ethanol (8.6 g, 49.7 mmol) in $CHCl_3$ (150 mL) at 0° C. was added a solution of di-tert-butyl dicarbonate (11.4 g, 52.0 mmol) in $CHCl_3$ (50 mL) in one portion and the resulting solution was stirred overnight at room temperature. The solvent was removed in vacuo and the residue was subjected to column chromatography on silica gel (2:1 hexane-EtOAc followed by EtOAc) to obtain [1-(3,4-difluorophenyl)-2-hydroxy-ethyl]-carbamic acid-tert-butyl ester as white solid (10.0 g, 74%).

b. (+)-4-(3,4-Difluorophenyl)-oxazolidin-2-one

To a well stirred suspension of NaH (1.1 g, 45.8 mmol) in THF (40 mL) at room temperature was added a solution of [1-(3,4-difluorophenyl)-2-hydroxy-ethyl]-carbamic acid-tert-butyl ester (5.0 g, 18.3 mmol) in 20 mL THF via a dropping funnel at room temperature. The resulting suspension was stirred for 3 hours and then quenched carefully with 10 mL of water. The biphasic mixture was extracted with 100 mL of $Et_2O$, washed with brine, filtered, and the solvent was removed in vacuo. The gummy residue thus obtained was purified by column chromatography over silica gel ($R_f$=0.15, 3:2 hexane-EtOAc) to obtain 4-(3,4-difluorophenyl)-oxazolidin-2-one as a white flaky solid (2.8 g, 77%). M.P. 81–83° C.; $^1$H NMR δ 4.13 (dd, J=6.6 Hz, J=8.7 Hz, 1 H), 4.73 (t, J=8.7 Hz, 1 H), 4.94 (dd, J=6.6 Hz, J=8.7 Hz, 1 H), 6.08 (br, s, 1 H), 7.03–7.23 (m, 3 H). The enantiomers were separated by using Chiralcel OD column (4.6×250 mm) using 80% hexane/20% isopropyl alcohol/0.1% diethylamine as the eluting system under isothermal conditions (U.V. 254 nM). The retention times for the two isomers were 16.19 min and 20.08 min respectively. First isomer: $[\alpha]_D$=+62.9 (c=0.67, acetone); Analysis calculated for $C_9H_7NO_2F_2$: C, 54.28; H, 3.54; N, 7.03. Found: C, 54.16; H, 3.44; N, 6.96. Second isomer: $[\alpha]_D$=−56.9 (c=0.75, acetone); Analysis calculated for $C_9H_7NO_2F_2$: C, 54.28; H, 3.54; N, 7.03. Found: C, 54.31; H, 3.46; N, 6.98. The first isomer was used in the next step.

c. (+)-2-Amino-2-(3,4-difluorophenyl)-ethanol

To a solution of (+)-4-(3,4-difluorophenyl)-oxazolidin-2-one (1.39 mmol, 0.27 g) in 5.0 mL ethanol was added 5.0 mL of water and pellets of potassium hydroxide (5.0 mmol, 0.28 g). The resulting solution was then heated to reflux overnight. The solvent was removed in vacuo and the resulting residue was extracted with EtOAc (2×50 mL). The organic extracts were washed with brine and the organic layer was dried over $Na_2SO_4$. It was filtered and the solvent was removed in vacuo to obtain (+)-2-amino-2-(3,4-difluorophenyl)-ethanol as a white solid (0.21 g, 87% yield).

This material was converted into (+)-3-(3,4-difluorophenyl)-5-oxo-morpholine-4-carboxylic acid-4-nitro-phenyl ester in the same manner as described in section I part 1g.

3. Typical Reaction for the Coupling of Side Chains ($RNH_2$) With Activated Morpholinones (Schemes 1 and 2) Synthesis of (+)-3-(3,4-difluorophenyl)-5-oxo-morpholine-4-carboxylic acid-{3-[4-(5-fluoro-2-methoxyphenyl)-4-phenyl-piperidin-1-yl]-propyl}-amide (Compound 1)

a. 4-(5-Fluoro-2-methoxy)-phenyl-4-phenyl-piperidine hydrochloride

To a 100 mL round bottom flask equipped with a rubber septum and a stirring bar was added 4-hydroxy-4-phenyl-piperidine (1.25 g, 7.0 mmol) followed by 10 mL of 4-fluoroanisole. The resulting solution was stirred at room temperature under argon atmosphere and $AlCl_3$ (2.82 g, 21.0 mmol) was added in one portion. An exotherm was observed. The reaction mixture was stirred for 8 hours and then poured carefully over 150 ml of ice-water. The white solid that precipitated out was filtered and washed thoroughly with water followed by diethyl ether to obtain 4-(5-fluoro-2-methoxy)-phenyl-4-phenyl-piperidine hydrochloride (1.59 g, 50%) as a white solid.

b. 3-[4-(2-methoxy-5-fluoro)phenyl-4-phenyl-piperidin-1-yl]propylamine

To a solution of 4-(5-fluoro-2-methoxy)-phenyl-4-phenyl-piperidine (0.6 g, 2.1 mmol) in 30 mL dioxane was added 3-bromo-N-tert-butoxycarbonyl-propylamine (0.6 g, 2.5 mmol) and $K_2CO_3$ (0.6 g, 6.0 mmol) and the resulting suspension was heated to reflux for 10 hours. The suspension was allowed to cool, filtered, and the solvent was evaporated to obtain yellow residue which was purified by column chromatography (Rf=0.4, 3:1 EtOAc/MeOH) to obtain 3-[4-(5-fluoro-2-methoxy)phenyl-4-phenyl-piperidin-1-yl]-N-tert-butoxycarbonyl-propylamine as a yellow oil (0.35 g). This was dissolved in 15 mL of $CH_2Cl_2$ and 3.0 mL of trifluoroacetic acid was added with stirring at room temperature under argon atmosphere for 1 hour. The solvent was evaporated in vacuo and the residue was basified to pH 10 by adding minimum amount of 1 N KOH solution. The product was extracted with $CH_2Cl_2$ (3×25 mL), dried over MgSO4, filtered, and the solvent was removed in vacuo to obtain 3-[4-(5-fluoro-2-methoxy)phenyl-4-phenyl-piperidin-1-yl]propylamine as a yellow oil (0.25 g, 35% for two steps). It was used in the next step without further purification.

c. (+)-3-(3,4-Difluorophenyl)-5-oxo-morpholine-4-carboxylic acid-{3-[4-(5-fluoro-2-methoxyphenyl)-4-phenyl-piperidin-1-yl]-propyl}-amide (Compound 1)

To a solution of (+)-3-(3,4-difluorophenyl)-5-oxo-morpholine-4-carboxylic acid-4-nitro-phenyl ester (0.05 g, 0.13 mmol) in 5 mL THF was added 3-[4-(5-fluoro-2-methoxy)phenyl-4-phenyl-piperidin-1-yl)-propylamine (0.06 g) in one portion and the resulting mixture was stirred at room temperature overnight. The solvent was removed in vacuo and the residue was passed through a short silica gel column with 1: hexane/EtOAc followed by 10% MeOH/EtOAc as the eluting system. 3-(3,4-Difluorophenyl)-5-oxo-morpholine-4-carboxylic acid-{3-[4-(5-fluoro-2-methoxyphenyl)-4-phenyl-piperidin-1-yl}-propyl}-amide was obtained as a colorless oil (0.05 g). It was dissolved in 4 mL of $CHCl_3$ and then treated with 1 mL of 1N HCl in diethyl ether to obtain its HCl salt. White solid. M.P.=110–113° C.; $[\alpha]_D$=+25.3 (c=0.14, MeOH); Analysis calculated for $C_{32}H_{35}N_3O_4F_3Cl.1.1\ CHCl_3$: C, 53.05; H, 4.86; N, 5.61. Found: C, 53.24; H, 5.06; N, 5.44.

4. Morpholinone Example: The Synthesis of (+)-3-(3,4-Difluoro-phenyl)-5-oxo-morpholine-4-carboxylic acid-{3-[4-(4-fluoro-2-methyl)phenyl piperidin-1-yl]-propyl}-amide (Compound 2)

a. 1-Benzyl-4-(5-fluoro-2-methyl)-phenyl-4-piperidinol

To a cooled solution of n-BuLi (6.0 mL, 15.0 mmol) in 20 mL THF was added 2-bromo-5-fluoro toluene (1.9 mL, 15.0 mmol) dropwise at −78° C. over 15 min. The reaction mixture was allowed to warm to 0° C. over 1 hour and was then cooled to −78° C. 1-Benzyl-4-piperidone (1.48 mL, 8.0 mmol) was added to the white slurry and the reaction mixture was warmed to 0° C. over 2 hours. The reaction was quenched with 10 mL of saturated $NH_4Cl$ solution. The organic layer was extracted with diethyl ether (2×50 mL) and the combined organic layers were washed with brine (100 mL). The organic layer was separated, dried over $Na_2SO_4$, filtered, and the solvent was removed in vacuo to obtain a yellow oil. It was purified by column chromatography over silica gel with 3:2 hexane-EtOAc as the eluting system to obtain 1-benzyl-4-(5-fluoro-2-methyl)-phenyl-4-piperidinol as a yellow thick oil (1.1 g, 46% yield).

b. 1-Benzyl-4-(4-Fluoro-2-methyl)-phenyl-1,2,3,6-tetrahydropyridine

To a solution of 1-benzyl-4-(5-fluoro-2-methyl)-phenyl-4-piperidinol (1.1 g, 3.68 mmol) in 100 mL toluene was added p-toluenesulfonic acid monohydrate (1.39 g, 7.35 mmol) and the resulting solution was heated to reflux for 8 hours. The suspension was cooled and the basified with 10% KOH solution and extracted with EtOAc (2×50 mL). The organic layer was washed with brine (30 mL). The organic layer was separated, dried over $Na_2SO_4$, filtered, and the solvent was removed in vacuo to obtain 1-benzyl-4-(4-fluoro-2-methyl)-phenyl-1,2,3,6-tetrahydropyridine as a pale yellow oil (0.9 g, 87% yield). It was used in the next step without further purification.

c. 4-(4-Fluoro-2-methyl)-phenyl-piperidine

To a cooled suspension of 10% Pd-C (0.1 g) in 10 mL methanol was added a solution of 1-benzyl-4-(4-fluoro-2-methyl)-phenyl-1,2,3,6-tetrahydropyridine (0.9 g, 3.2 mmol) in 20 mL of methanol and the resulting suspension was hydrogenated at room temperature under 1 atm of hydrogen for 10 hours. The suspension was filtered through a pad of celite and the solvent was removed from the filtrate to obtain 4-(4-fluoro-2-methyl)phenyl-piperidine which was converted into its hydrochloride salt (0.62 g, 99% yield). It was used in the next step without further purification.

d. (+)-3-(3,4-Difluoro-phenyl)-5-oxo-morpholine-4-carboxylic acid-{3-[4-(4-fluoro-2-methyl)phenyl piperidin-1-yl]-propyl}-amide (Compound 2)

4-(4-Fluoro-2-methyl)-phenyl-piperidine was converted into 3-amino-propyl-4-(4-fluoro-2-methyl)phenyl-piperidine by the same manner as described in section I, part 3b. This was further converted into (+)-3-(3,4-difluoro-phenyl)-5-oxo-morpholine-4-carboxylic acid-{3-[4-(4-fluoro-2-methyl)phenyl piperidin-1-yl]-propyl}-amide by the same manner as described in section I part 3c. White solid. M.P.=92–96° C.; $[\alpha]_D$=+19.1 (c=0.12, MeOH); Analysis calculated for $C_{26}H_{31}N_3O_3F_3Cl.0.5\ CHCl_3$: C, 54.35; H, 5.42; N, 7.17. Found: C, 54.20; H, 5.51; N, 6.81.

5. Morpholinone Example: The Synthesis of (+)-3-(3,4-difluoro-phenyl)-5-oxo-morpholine-4-carboxylic acid-{3-[4-(4-fluoro)phenyl-piperidin-1-yl]-propyl}-amide (Compound 3)

a. 1-benzyl-4-(4-fluoro-phenyl)-1,2,3,6-tetrahydropyridine

To a solution of 4-fluorophenylmagnesium bromide (110.0 mmol, 55.0 mL of 2.0 M solution) in 150.0 mL THF at 0° C. was added 1-benzyl-4-piperidone (55.0 mmol, 10.2 mL) dropwise. The resulting solution was stirred under argon atmosphere for 1.5 hours and then quenched with 100.0 mL of saturated $NH_4Cl$ solution. The organic layer was separated and the aqueous layer was extracted with 100.0 mL of $Et_2O$. The combined organic extracts were washed with brine, separated, and dried over $Na_2SO_4$. The solution was filtered and the solvent was removed in vacuo to obtain a yellow oil which was purified by passing through a silica gel column with 4:1 hexane/EtOAc followed by 1:1 hexane/EtOAc as the eluting system. 1-Benzyl-4-(4-fluoro-phenyl)-piperidin-4-ol was obtained as a pale yellow oil in 89% yield (13.9 g). It was dissolved in 150.0 mL of toluene and p-toluenesulfonic acid monohydrate (50.0 mmol, 9.5 g) was added. The resulting suspension was heated to reflux for 8 hours. After the suspension was cooled, it was basified with 3 N NaOH solution and was extracted with $Et_2O$ (2×50 mL). The organic extracts were combined, washed with brine, and the organic layer was dried over $Na_2SO_4$. The solvent was removed in vacuo to obtain 1-benzyl-4-(4-fluoro-phenyl)-1,2,3,6-tetrahydropyridine as a yellow viscous oil (12.0 g, 92% yield) which was used in the next step without further purification.

b. 4-(4-fluoro)-phenyl-piperidine

To a solution of 1-benzyl-4-(4-fluoro-phenyl)-1,2,3,6-tetrahydro-pyridine (45.0 mmol, 12.0 g) in 100 mL MeOH was added 1.0 g of $Pd(OH)_2$ and the resulting suspension was hydrogenated under 200 psi of $H_2$ in a stainless steel bomb for two days. The suspension was passed through a pad of celite and the filtrate was concentrated in vacuo to obtain 4-(4-fluoro)-phenyl-piperidine (7.5 g, 94%) as a viscous oil.

c. (+)-3-(3,4-Difluoro-phenyl)-5-oxo-morpholine-4-carboxylic acid-{3-[4-(4-fluoro)phenyl-piperidin-1-yl]-propyl}-amide (Compound 3) 4-(4-Fluoro)-phenyl-piperidine was converted into 3-[4-(4-fluoro-phenyl)-piperidin-1-yl]-propylamine in the same manner as described in section I part 3b. This was further converted into (+)-3-(3,4-difluoro-phenyl)-5-oxo-morpholine-4-carboxylic acid-{3-[4-(4-fluoro)phenyl-piperidin-1-yl]-propyl}-amide by the same manner described section I part 3c. White solid. M.P.=86–90° C.; $[\alpha]_D$=+22.7 (c=0.23, MeOH); Analysis calculated for $C_{25}H_{29}N_3O_3F_3Cl.0.4\ CHCl_3$: C, 54.51; H, 5.29; N, 7.51. Found: C, 54.74; H, 5.48; N, 7.26.

6. Morpholinone Example: 3-(3,4-Difluoro-phenyl)-5-oxo-morpholine-4-carboxylic acid-{3-[4-(2-carboxamido)-phenyl-piperiazin-1-yl]-propyl}-amide (Compound 4)

a. 1-(2-carboxamidophenyl)piperazine

Concentrated sulfuric acid (15 mL) was added to 1-(2-cyanophenyl)piperazine (1.5 g, 8.0 mmol) placed in a round bottom flask, and the resulting slurry was stirred at room temperature for 48 hours. The reaction mixture was poured on crushed ice very slowly and then basified (pH 9) with 50% solution of NaOH. The aqueous layer was extracted several times with EtOAc, dried over $K_2CO_3$, filtered, and the solvent was evaporated. 1-(2-carboxamidophenyl) piperazine was obtained as an off-white solid (1.2 g, 73%).

b. 3-(3,4-difluoro-phenyl)-5-oxo-morpholine-4-carboxylic acid-{3-[4-(2-carboxamido)-phenyl-piperiazin-1-yl]-propyl}-amide (Compound 4)

1-(2-carboxamidophenyl)piperazine was converted into 1-(3-amino-propyl)-4-(2-carboxamido)-phenyl-piperazine in the same manner as described in section I part 3b. This was further converted into 3-(3,4-difluorophenyl)-5-oxo-morpholine-4-carboxylic acid-{3-[4-(2-carboxamido)-phenyl- piperiazin-1-yl]-propyl}-amide in the same manner as described in section I part 3c. Pale yellow powder. M.P. 118–122° C.; Analysis calculated for $C_{25}H_{30}N_5O_4F_2Cl.1.1$ hexane: C, 59.98; H, 7.23; N, 11.07. Found: C, 60.20; H, 7.50; N, 11.32.

7. Morpholinone Example: Synthesis of 3-(3,4-Difluoro-phenyl)-5-oxo-morpholine-4-carboxylic Acid-{3-[4-(2-nitro)-phenyl-piperazin-1-yl)propyl}-amide (Compound 5)

a. 1-(2-nitrophenyl)-piperazine

A heterogenous reaction mixture containing 2-bromonitrobenzene (2.02 g, 10.0 mmol) and piperazine (4.3 g, 50.0 mmol) was heated at 100° C. for 10 hours. The orange-red solid was extracted with ethyl acetate and washed thoroughly with 3 N NaOH solution followed by brine. The organic layer was separated and dried over $Na_2SO_4$, filtered and the solvent was removed in vacuo. The resulting red oil was purified by column chromatography on silica gel (1:1 hexane/EtOAc followed by 4:1 EtOAc/MeOH) to yield 1-(2-nitrophenyl)piperazine as an orange-red oil (1.90 g, 92%). It was characterized as a hydrochloride salt. Analysis calculated for $C_{10}H_{14}N_3O_2Cl.0.10.$ $CHCl_3$: C, 47.46; H. 5.56; N, 16.44. Found: C, 47.63; H. 5.69; N, 16.42.

b. 3-(3,4-difluoro-phenyl)-5-oxo-morpholine-4-carboxylic acid-{3-[4-(2-nitro)-phenyl-piperazin-1-yl]-propyl}-amide (Compound 5)

1-(2-nitrophenyl)-piperazine was converted into 1-(3-amino-propyl)-4-(2-nitrophenyl)-phenyl-piperazine in the same manner as described in section I part 3b. This was further converted into 3-(3,4-difluoro-phenyl)-5-oxo-morpholine-4-carboxylic acid-{3-[4-(2-nitro)-phenyl-piperiazin-1-yl)-propyl}-amide in the same manner as described in section I part 3c. Pale yellow sticky solid. M.P.=68–72° C.; Mass spec. 504 (M+1, 100%); Analysis calculated for $C_{24}H_{28}N_5O_5F_2Cl.1.2$ hexane: C, 58.25; H, 7.02; N, 10.89. Found: C, 58.39; H, 7.02; N, 10.13.

8. Morpholinone Example: 3-(3,4-Difluoro-phenyl)-5-oxo-morpholine-4-carboxylic acid-{3-[4-(2-methyl)phenyl-4-(4-methyl)-phenyl-piperidin-1-yl]-propyl}amide (Compound 6)

a. 4-(4-Methyl)-phenyl-4-(2-methyl)phenyl piperidine hydrochloride

To a 100 mL round bottom flask equipped with a rubber septum and a stirring bar was added 4-hydroxy-4-(4-methyl) phenyl-piperidine (1.25 g, 6.54 mmol) followed by 20 mL of anhydrous toluene. The resulting solution was stirred at room temperature under argon atmosphere and then $AlCl_3$ (1.4 g, 10.2 mmol) was added in one portion. An exotherm was observed. The reaction mixture was stirred for 10 hours and then poured carefully over 100 ml of ice-water. The white solid that precipitated out was filtered and washed thoroughly with water followed by diethyl ether to obtain 4-(4-methyl)-phenyl-4-(2-methyl)phenyl piperidine hydrochloride (1.95 g, 99%) as a white solid. Mass spectrum: 266 (M+1, 100%). Analysis calculated for $C_{19}H_{24}NCl$ 0.15 $CH_2Cl_2$: C, 73.11; H, 7.79; N, 4.45. Found: C, 73.33; H, 7.82; N, 3.92.

b. 3-[4-(4-methyl-phenyl-4-(2-methyl)phenyl piperidin-1-yl]propylamine

To a solution of 4-(4-methyl)-phenyl-4-(2-methyl)phenyl piperidine hydrochloride (2.6 g, 9.8 mmol) in 100 mL dioxane was added 3-bromo-N-tert-butoxycarbonylpropylamine (2.57 g, 10.8 mmol) and $K_2CO_3$ (4.06 g, 29.4 mmol) and the resulting suspension was heated to reflux for 10 hours. The suspension was allowed to cool, filtered, and the solvent was evaporated to obtain a yellow residue which was purified by column chromatography (Rf=0.4, 3:1 EtOAc/MeOH) to obtain 3-[4-(4-methyl-phenyl-4-(2-methyl)phenyl piperidin-1-yl]-N-tert-butoxycarbonyl-propylamine as a yellow oil (2.30 g). It was dissolved in 60 mL of $CH_2Cl_2$ and 10.0 mL of trifluoroacetic acid was added with stirring at room temperature under argon atmosphere for 1 hour. The solvent was evaporated in vacuo and the residue was basified to pH 10 by adding minimum amount of 1 N KOH solution. The product was extracted with $CH_2Cl_2$ (3×25 mL), dried over MgSO4, filtered, and the solvent was removed in vacuo to obtain 3-[4-(4-methyl)-phenyl-4-(2-methyl)phenyl piperidin-1-yl] propylamine as a yellow oil (1.39 g, 44% for two steps).

c. 3-(3,4-difluoro-phenyl)-5-oxo-morpholine-4-carboxylic acid-{3-[4-(2-methyl)-phenyl-4-(4-methyl)phenyl-piperidin-1-yl]-propyl}-amide (Compound 6)

3-[4-(4-methyl-phenyl-4-(2-methyl)phenyl piperidin-1-yl]propylamine was converted into 3-(3,4-difluorophenyl)-5-oxo-morpholine-4-carboxylic acid-{3-[4-(2-methyl)-phenyl-4-(4-methyl)-phenyl-piperidin-1-yl]-propyl}-amide in the same manner as described in section I part 3c. Yellow sticky solid.; Mass spec. 562 (M+1, 100%); Analysis calculated for $C_{33}H_{38}N_3O_3F_2Cl.0.75$ $CH_2Cl_2$: C, 61.25; H, 6.02; N. 6.35. Found: C, 61.07; H, 6.46; N, 5.95.

9. Morpholinone Example: The Synthesis of 3-(3,4-Difluoro-phenyl)-5-oxo-morpholine-4-carboxylic acid-{3-[4-cyano-4-(phenyl)cyclohex-1-yl]-ethyl}]-amide (Compound 7)

A general procedure was utilized to form 3-[4-cyano-4-(phenyl)cyclohex-1-yl]-ethylamine. A mixture of 4-cyano-4-aryl-cyclohexanone (48.7 mmol) and ethylenediamine (8.78 g, 146 mmol) and p-toluenesulfonic acid (92 mg) in benzene (200 mL) was refluxed for 4 hour with Dean-Stark trap to remove the water that formed. Solvent was evaporated and the residue was redissolved in methanol (60 mL) and cooled to 0° C. Sodium borohydride (6.45 g) was added in portions and the mixture was stirred at room temperature for 3 hours. Solvent was evaporated, the residue was dissolved in dichloromethane (300 mL), washed with brine (3×500 mL), dried (potassium carbonate), and the solvent evaporated to leave the product as a pale yellow viscous oil (90–95%). The product was found to contain the cis/trans isomers in a ratio of about 9:1. Careful chromatography of this mixture with chloroform/methanol/2 M ammonia in methanol (100/10/5 to 100/20/10) yielded several earlier fractions enriched in trans isomer with respect to the amino and cyano groups. Later fractions eluted contained almost pure cis isomer relative to the amino and cyano groups. 3-[4-cyano-4-(phenyl)cyclohex-1-yl]ethylamine was converted to 3-(3,4-difluoro-phenyl)-5-oxo-morpholine-4-carboxylic acid-{3-[4-cyano-4-(phenyl)cyclohex-1-yl]-ethyl}-amide in the same manner as described in section I part 3c. Yellow powder.; M.P.=85–89° C.; Analysis calculated for $C_{26}H_{29}N_4O_3F_2Cl1.0$ $CH_2Cl_2$: C, 53.70; H, 5.17; N, 9.28. Found: C, 53.78; H, 5.30; N. 8.87.

10. Morpholinone Example: The Synthesis of 3-(3,4-difluoro-phenyl)-5-oxo-morpholine-4-carboxylic acid-{3-[4-(2-carbomethoxy-phenyl-piperazin-1-yl]-propyl}-amide (Compound 8)

a. 1-(2-carbomethoxyphenyl)-piperazine

To a solution of methyl 2-bromobenzoate (1.63 g, 17.8 mmol) in 1,6-dioxane (100 ml) at room temperature was added piperazine (15.3 g, 178 mmol) and $K_2CO_3$ (4.92 g, 35 mmol). The resulting mixture was heated to reflux for 7 days after which the reaction mixture was cooled to room temperature. The solvent and the excess piperazine were removed in vacuo along with heating with a hot water bath. The residue was dissolved in 1N NaOH solution, extracted with $CH_2Cl_2$ (6×30 ml), and dried over $Na_2SO_4$. The solvent was removed in vacuo to obtain 1-(2-carbomethoxyphenyl)-piperazine as a yellow oil (1.0 g, 26%).

b. 3-(3,4-Difluoro-phenyl)-5-oxo-morpholine-4-carboxylic acid-{3-[4-(2-carbomethoxy-phenyl-piperazin-1-yl]-propyl}-amide (Compound 8)

1-(2-Carbomethoxyphenyl)-piperazine was converted into 1-(3-amino-propyl)-4-(2-carbomethoxyphenyl)-piperazine in the same manner as described in section I part 3b. This was further converted into 3-(3,4-difluorophenyl)-5-oxo-morpholine-4-carboxylic acid-{3-[4-(2-carbomethoxy-phenyl-piperazin-1-yl]-propyl}-amide in the same manner as described in section I, part 3c. Yellow hygroscopic solid; Analysis calculated for $C_{26}H_{32}N_4O_5F_2Cl_2.0.3$ $CH_2Cl_2$: C, 51.37; H, 5.34; N, 9.11. Found: C, 51.16; H, 5.37; N. 8.27.

11. 3-(3,4-Difluoro-phenyl)-5-oxo-morpholine-4-carboxylic acid-{2-[4-carbomethoxy-4-phenyl-piperidin-1-yl]-ethyl}-amide (Compound 9)

a. 3-[4-Carbomethoxy-4-phenyl-piperidin-1-yl]-ethylamide

To a solution of 4-carbomethoxy-4-phenyl-piperidine (0.4 g, 2.1 mmol) in 30 mL dioxane was added 3-bromo-N-tert-butoxycarbonyl-ethylamine (0.5 g, 2.5 mmol) and $K_2CO_3$ (0.6 g, 6.0 mmol) and the resulting suspension was heated to reflux for 10 hours. The suspension was allowed to cool, was filtered, and the solvent was evaporated to obtain a yellow residue which was purified by column chromatography (Rf=0.4, 3:1 EtOAc/MeOH) to obtain 3-[4-carbomethoxy-4-phenyl-piperidin-1-yl]-N-tert-butoxycarbonyl-ethylamine as a yellow oil (0.35 g). It was dissolved in 15 mL of $CH_2Cl_2$ and 3.0 mL of trifluoroacetic acid was added with stirring at room temperature under argon atmosphere for 1 hours. The solvent was evaporated in vacuo and the residue was basified to pH 10 by adding minimum amount of 1 N KOH solution. The product was extracted with $CH_2Cl_2$ (3×25 mL), dried over MgSO4, filtered and the solvent was removed in vacuo to obtain 3-[4-carbomethoxy-4-phenyl-piperidin-1-yl]ethylamine as a yellow oil (0.25 g, 55% for two steps). Yellow solid; M.P.=113–117° C.; Analysis calculated for $C_{26}H_{30}N_3O_5F_2Cl.0.3$ $Et_2O$: C, 58.32; H, 6.14; N, 6.81. Found: C, 58.31; H, 5.94; N. 7.50.

b. 3-(3,4-Difluoro-phenyl)-5-oxo-morpholine-4-carboxylic acid-{2-[4-carbomethoxy-4-phenyl-piperidin-1-yl]-ethyl}-amide (Compound 9)

3-[4-Carbomethoxy-4-phenyl-piperidin-1-yl]-ethylamine was converted into 3-(3,4-difluoro-phenyl)-5-oxo-morpholine-4-carboxylic acid-{2-[4-carbomethoxy-4-phenyl-piperidin-1-yl]-ethyl}-amide in the same manner as described in section I, part 3c. Yellow solid; M.P.=113–117° C.; Analysis calculated for $C_{26}H_{30}N_3O_5F_2Cl.0.3$ $Et_2O$: C, 58.32; H, 6.14; N, 6.81. Found: C, 58.31; H, 5.94; N, 7.50.

12. Morpholinone Example: Synthesis of 3-(3,4-Difluoro-phenyl)-5-oxo-morpholine-4-carboxylic acid-{3-[4-hydroxy-4-phenyl-piperidin-1-yl]-propyl}amide (Compound 10)

a. 3-[4-Hydroxy-4-phenyl-piperidin-1-yl]-propylamine

3-[4-Hydroxy-4-phenyl-piperidin-1-yl]-propylamine was synthesized from commercially available 4-hydroxy-4-phenyl piperidine using the same procedure as described in section I, part 3b.

b. 3-(3,4-Difluoro-phenyl)-5-oxo-morpholine-4-carboxylic acid-{3-[4-hydroxy-4-phenyl-piperidin-1-yl]-propyl}-amide (Compound 10)

3-[4-Hydroxy-4-phenyl-piperidin-1-yl]-propylamine was converted into 3-(3,4-difluoro-phenyl)-5-oxo-morpholine-4-carboxylic acid-{3-[4-hydroxy-4-phenyl-piperidin-1-yl]-propyl}-amide in the same manner as described in section I, part 3c. Yellow solid.; M.P.=85–88° C.; Analysis calculated for $C_{25}H_{30}N_3O_4F_2Cl.0.2$ MeOH: C, 58.61; H, 6.01; N, 8.14. Found: C, 58.29; H, 6.42; N, 7.98.

13. (−)-3-Phenyl)-5-oxo-morpholine-4-carboxylic acid-{3-[4-(5'-fluoro-2'-methoxy)phenyl-4-phenyl-piperidin-1-yl]-propyl}-amide (Compound 11)

3-Phenyl-5-oxo-morpholine-4-carboxylic acid-4-nitrophenyl ester was prepared from R-(−)-phenyl glycinol in the same manner as described in section I, parts 1d–g. It was coupled with 3-[4-(5-fluoro-2-methoxy)phenyl-4-phenyl-piperidin-1-yl)-propylamine (section I parts 3a–b) in the same manner as described in section I, part 3c. White powder. M.P.=105–109° C.; $[\alpha]_D$=−49.0 (c=0.12, MeOH) Analysis calculated for $C_{32}H_{37}N_3O_4F_2Cl.1.0$ $CH_2Cl_2$: C, 59.42; H, 5.89; N, 6.30. Found: C, 59.51; H, 6.22; N, 6.05.

II. Synthesis of Substituted Morpholinone Examples

1. Synthesis of 3-(3,4-difluorophenyl)-2-methyl-5-oxo-morpholine-4-carboxylic acid-4-nitro-phenyl ester (Scheme 3)

a. 2-Hydroxy-1-pyrrolidin-1-yl-propan-1-one

The procedure has been reported (Vilarrasa et al., *Tetrahedron Lett.* 38, 1633, 1997). S-(+)-Methyl lactate (48.03 mmol, 5.0 g) and pyrrolidine (52.8 mmol, 4.4 mL) were mixed in a round bottom flask and the reaction mixture was allowed to stir at room temperature for four days. Methanol was distilled off using a short path distillation apparatus to obtain 2-hydroxy-1-pyrrolidin-1-yl-propan-1-one as a yellow oil. It was used in the next reaction without further purification.

b. 2-(tert-Butyl-dimethyl-silanyloxy)-1-pyrrolidin-1-yl-propan-1-one

To a solution of 2-hydroxy-1-pyrrolidin-1-yl-propan-1-one (47.0 mmol, 6.72 g) in DMF (25 mL) was added imidazole (70.5 mmol, 4.8 g), N,N-dimethyl-4-aminopyridine (4.7 mmol, 0.57 g) at room temperature. tert-Butyl-dimethylsilyl chloride (48.5 mmol, 7.31 g) was then added while stirring. Some exotherm was observed. The initial pale yellow solution turned brown-red in color and some precipitate was observed after 30 min. The reaction mixture was stirred overnight and was then filtered through a sintered glass funnel. The solid was washed with $Et_2O$. The filtrate was diluted with water (150 mL) and it was extracted with $Et_2O$ (2×100 mL). The organic extracts were combined and washed successively with water (100 mL), saturated $NH_4Cl$ solution, and the organic layer was separated. It was dried over $Na_2SO_4$, filtered, and the solvent was removed in vacuo to obtain 2-(tert-butyl-dimethyl-silanyloxy)-1-pyrrolidin-1-yl-propan-1-one as a golden yellow oil (10.4 g, 86% yield). The product was judged to be >95% pure by NMR and was used in next step without any purification.

c. 2-(tert-Butyl-dimethyl-silanyloxy)-1-(3,4-difluorophenyl)-1-yl-propan-1-one

To a round bottom flask containing 72.0 mL of THF at −78° C. was added a solution of n-butyllithium in hexane (72.0 mmol, 45.0 mL) under an argon atmosphere followed by 1-bromo-3,4-difluorobenzene (72.0 mmol, 8.1 mL). A solution of 2-(tert-butyl-dimethyl-silanyloxy)-1-pyrrolidin-1-yl-propan-1-one (60.0 mmol, 15.4 g) in 10.0 mL THF was then added in a steady stream and the orange colored solution was stirred for 35 min at −78° C. It was quenched with 20.0 mL of saturated $NH_4Cl$ solution and was allowed to attain room temperature. The solution was extracted with $Et_2O$ (2×50 mL), washed with brine, and the organic layer was dried over $Na_2SO_4$. The solution was filtered, and the solvent was removed in vacuo to obtain the product as an orange oil. The crude product was subjected to silica gel flash column chromatography (9:1 hexane/EtOAc to 4:1 hexane/EtOAc as the eluent system). 2-(tert-Butyl-dimethyl-silanyloxy)-1-(3,4-difluoro-phenyl)-1-yl-propan-1-one was obtained as a pale yellow oil (14.1 g, 78% yield, 96% based on the recovered starting material).

d. 2-(tert-Butyl-dimethyl-silanyloxy)-1-(3,4-difluorophenyl)-1-yl-propan-1-one-oxime To a solution of 2-(tert-butyl-dimethyl-silanyloxy)-1-(3,4-difluoro-phenyl)-1-yl-propan-1-one (13.7 mmol, 4.1 g) in 60.0 mL of methanol was added sodium acetate (3.76 g) and hydroxylamine hydrochloride (1.24 g) and the resulting solution was stirred at room temperature overnight. Methanol was then removed in vacuo and the resulting residue was extracted with EtOAc (2×50 mL) and brine. The organic layer was separated, dried over $Na_2SO_4$, filtered, and the solvent was removed in vacuo. 2-(tert-Butyl-dimethyl-silanyloxy)-1-(3,4-difluorophenyl)-1-yl-propan-1-one-oxime was obtained as a colorless oil (4.04 g, 94% yield) and was used in the next step without further purification.

e. 1-Amino-1-(3,4-difluorophenyl)-propan-2-ol

To a solution of 2-(tert-butyl-dimethyl-silanyloxy)-1-(3,4-difluoro-phenyl)-1-yl-propan-1-one-oxime (12.2 mmol, 3.84 g) in 20.0 mL of $Et_2O$ was added a 1.0 M solution of lithium aluminum hydride (25.0 mmol, 25.0 mL) at 0° C. under an argon atmosphere. After 1 hour, the solution was heated to reflux for 2 hours at which time some solid was observed. The reaction mixture was cooled to 0° C. and then quenched sequentially with water (1.0 mL), 1.0 N KOH (1.0 mL), and water (3.0 mL). The residue was filtered and the solid was washed with warm $Et_2O$ (20.0 mL). The filtrates were combined and dried over $Na_2SO_4$. The solution was filtered and the solvent was removed in vacuo to obtain 1-amino-1-(3,4-difluorophenyl)-propan-2-ol as a colorless oil which solidified into a low melting solid (2.1 g, 92% yield). It was used in the next step without purification.

f. 3-(3,4-Difluorophenyl)-2-methyl-5-oxo-morpholine-4-carboxylic acid-4-nitro-phenyl ester 1-Amino-1-(3,4-difluorophenyl)-propan-2-ol was converted to 3-(3,4-difluorophenyl)-2-methyl-5-oxo-morpholine-4-carboxylic acid-4-nitro-phenyl ester in the same manner as described in section I, parts 1d–g or 2.

2. Substituted Morpholinone Example: (+)-3-(3,4-Difluoro-phenyl)-2-methyl-5-oxo-morpholine-4-carboxylic acid-{3-[4-(4-fluoro)phenyl-piperidin-1-yl]-propyl}-amide (Compound 12)

3-(3,4-Difluorophenyl)-2-methyl-5-oxo-morpholine-4-carboxylic acid-4-nitro-phenyl ester (section II part 1) was coupled to 3-[4-(4-fluoro)phenyl-piperidin-1-yl]-propylamine (section I part 5) in the same manner as described in section I, part 3c. Yellow hygroscopic solid. M.P.=69–73° C.; Mass spec. 490 (M+1, 100%); $[\alpha]_D$=+20.2 (c=0.08, MeOH). Analysis calculated for $C_{26}H_{31}N_3O_3F_2Cl.2.0\ H_2O$: C, 57.51; H, 6.50; N, 7.74. Found: C, 57.61; H, 6.15; N, 7.27.

3. Substituted Morpholinone Example: (+)-3-(3,4-Difluoro-phenyl)-2-methyl-5-oxo-morpholine-4-carboxylic acid-{3-[4-(4-fluoro-2-methoxy)phenyl-4-phenyl-piperidin-1-yl]-propyl}-amide (Compound 13)

3-(3,4-Difluorophenyl)-2-methyl-5-oxo-morpholine-4-carboxylic acid-4-nitro-phenyl ester (section II part 1) was coupled to 3-[4-(4-fluoro-2-methoxy)phenyl-4-phenyl-piperidin-1-yl]-propylamine (section I, part 3a-b) in the same manner as described in section I, part 3c. Yellow powder. M.P.=95–99° C.; Mass spec. 596 (M+1, 100%); $[\alpha]_D$=+56.9 (c=0.13, MeOH) Analysis calculated for $C_{33}H_{36}N_3O_4F_2Cl.1.5\ CH_2Cl_2$: C, 54.56; H, 5.31; N, 5.53. Found: C, 54.51; H, 5.63; N, 5.20.

4. Substituted Morpholinone Example: (+)-3-(3,4-Difluoro-phenyl)-2-methyl-5-oxo-morpholine-4-carboxylic acid-{3-[4-(cyano-4-phenyl-piperidin-1-yl]-propyl}-amide (Compound 14)

a. 3-(4-Cyano-4-phenylpiperidin-1-yl)propylphthalimide

A mixture of 4-cyano-4-phenylpiperidine hydrochloride (111 g, 0.5 mol), 3-bromopropylphthalimide (135.39 g, 0.505 mol), potassium carbonate (276.42 g, 2 mol), and potassium iodide (5.4 g) in DMF (1 L) was stirred and heated at 100–110° C. for 8 hours. About 80% of the solvent was evaporated at reduced pressure, the residue was diluted with dichloromethane (1 L) and washed with brine (3×300 mL) and dried ($Na_2SO_4$). Solvent was evaporated from the dichloromethane solution and the residue was treated with isopropanol (400 mL) and cooled. The pale yellow crystalline product formed was filtered, washed with ice-cold isopropanol and dried (168.6 g, 90%); M.p. 96–98° C.

b. 3-(4-Cyano-4-phenylpiperidin-1-yl)propylamine

To a solution of 3-(4-cyano-4-phenylpiperidin-1-yl) propylphthalimide (112 g, 0.3 mol) in methanol (1.5 L), hydrazine (30 mL) was added and the mixture was stirred and refluxed for 20 hours. It was cooled, the white solid formed was filtered and washed with more methanol (200 mL). Solvent was evaporated from the filtrate and residue was dried under vacuum for 4 hours. Chloroform (500 mL) was added to this, stirred for 1 hour and filtered. The white solid was washed with more chloroform (200 mL), the solvent was evaporated from the combined filtrates to leave the product as an oil (70 g, 96%).

c. (+)-3-(3,4-Difluoro-phenyl)-2-methyl-5-oxo-morpholine-4-carboxylic acid-{3-[4-(cyano-4-phenyl-piperidin-1-yl]-propyl}-amide 3-(3,4-Difluorophenyl)-2-methyl-5-oxo-morpholine-4-carboxylic acid-4-nitro-phenyl ester (section II, part 1) was coupled to 3-[4-(cyano-4-phenyl-piperidin-1-yl]-propylamine in the same manner as described in section I, part 3c. White powder. M.P.=191–194° C.; Mass spec. 497 (M+1, 100%); $[\alpha]_D$=+23.1 (c=0.09, MeOH) Analysis calculated for $C_{33}H_{36}N_3O_4F_2Cl \cdot 0.35\ CH_2Cl_2$: C, 58.38; H, 5.68; N, 9.96. Found: C, 58.57; H, 6.03; N, 9.72.

III. Synthesis of Substituted Morpholinone Examples (Schemes 4a and 4b)

1. Synthesis of (+)-4-nitrophenyl 2,2-dimethyl-3-(3,4-difluorophenyl)-5-oxo-morpholinecarboxylate (Scheme 4a)

a. Amino-(3,4,-difluorophenyl)-acetonitrile

Through a solution of 3,4-difluorobenzaldehyde (25.0 g, 0.18 mol) in MeOH (500 mL) in a round bottom flask was bubbled ammonia gas for two hours at room temperature. The flask was then cooled to 0° C. and trimethylsilyl cyanide (1.3 eq., 0.23 mmol) was then added slowly. The reaction mixture was stirred for 2 hours when TLC analysis indicted that the reaction was complete ($R_f$= 0.35, 3:2 hexane/EtOAc). Solvent was removed in vacuo and the residue was subjected to flash column chromatography on silica gel to obtain 25.0 g (81%) of amino-(3,4-difluorophenyl)-acetonitrile as a yellow syrup.

b. Methyl 2-amino-2-(3,4-difluorophenyl)acetate

To a well stirred solution of amino-(3,4-difluorophenyl)-acetonitrile (22.0 g., 0.130 mol), a solution of HCl in MeOH (200 mL) was added at room temperature. The resulting yellow solution was stirred at room temperature for 10 hours and then heated to reflux for 1.5 hours. After cooling, the solvent was removed in vacuo and the resulting yellow solid was dissolved in water (200 mL). The aqueous solution was then carefully basified with 20% NaOH solution to pH 9. The aqueous layer was extracted with $CH_2Cl_2$ (3×100 mL). The organic layer was separated and dried over $Na_2SO_4$, filtered and the solvent was removed in vacuo to obtain 22.2 g (84%) of methyl 2-amino-2-(3,4-difluorophenyl)acetate as a brownish yellow liquid. It was used in the next step without purification.

c. (+)-1-(3,4-Difluorophenyl)-2,2-dimethyl-2-hydroxypropylamine

To a well-stirred solution of methyl 2-amino-2-(3,4-difluorophenyl)acetate (10.5 g, 52.19 mmol) in anhydrous ether (200 mL) at 0° C. was added a solution of methylmagnesium bromide in ether (3 M, 87 mL, 261 mmol) over 10 minutes. The mixture was stirred at 0° C. for 2.5 hours and allowed to warm to room temperature. After 12 hours, the mixture was carefully poured onto a mixture of ice (300 g) and saturated ammonium chloride (50 g). The ether layer was separated and the aqueous layer was extracted with more ether (4×200 mL). The combined extracts were dried over magnesium sulfate and the solvent evaporated. The crude product was purified by column chromatography on silica gel using chloroform/methanol/2M ammonia in methanol (1000:20:10/1000:40:20, 1000:80:40) as eluents to give the product as an oil (6.5 g, 62%). The $^1$H-NMR and MS confirmed this to be the desired product.

d. (+)-1-(3,4-Difluorophenyl)-2,2-dimethyl-2-hydroxypropylamine chloroacetamide

To a solution of 1-(3,4-difluorophenyl)-2,2-dimethyl-2-hydroxypropylamine (10.20 g, 50.70 mmol) and triethylamine (5.0 mL) in dichloromethane (100 mL) at −78° C. was added chloroacetyl chloride (4.64 mL, 60.83 mmol) dropwise over 10 min. The resulting mixture was stirred at −78° C. for 2 hours and was then slowly warmed to −40° C. over one hour. The reaction was quenched by adding $H_2O$ (20 mL) and the mixture was extracted with EtOAc (2×100 mL). The ethyl acetate extracts were dried over $MgSO_4$ and concentrated to a residue which was purified by column chromatography ($SiO_2$, 30% to 50% EtOAc/Hex) to afford the product as a colorless oil (6.50 g, 46 % yield).

e. (+)-2,2-Dimethyl-3-(3,4-difluorophenyl)-5-oxo-morpholine

Lithium bis(trimethylsilyl)amide (5.68 mL, 1.0 M in THF) was added to a stirred solution of 1-(3,4-difluorophenyl)-2-methyl-2-hydroxypropylamine 2-chloroacetamide (1.21 g, 4.37 mmol) in THF at 0° C. The resulting mixture was stirred while warmed to room temperature over 30 min. It was then heated to 50° C. and stirred for 60 min. The mixture was quenched with water (2 mL) and extracted with EtOAc (2×100 mL). The extracts were dried ($Na_2SO_4$) and the solvent was evaporated. The crude product was purified by column chromatography ($SiO_2$, 50:50 to 90:10 EtOAc/Hexanes) to give 0.36 g (34%) of morpholinone as a pale yellow oil.

f (+)-4-Nitrophenyl 2,2-dimethyl-3-(3,4-difluorophenyl)-5-oxo-morpholinecarboxylate To a solution of (+)-2,2-dimethyl-3-(3,4-difluorophenyl)-5-oxo-morpholine (240 mg, 0.996 mmol) in THF (10 mL) at −78° C. was added lithium bis(trimethylsilyl)amide (1.10 mL, 1.0 M in THF). The mixture was stirred for 30 min at 0° C. and then cooled back to −78° C. The mixture was transferred via a cannula to a precooled solution of 4-nitrophenyl chloroformate (605 mg, 3.0 mmol) in THF (10 mL) at −78° C. The resulting mixture was stirred while warmed to room temperature over 3 hours. The reaction was quenched with water (2 mL) and extracted with EtOAc (2×100 mL). The organic layer was dried with $Na_2SO_4$ and the solvent was evaporated. The residue was purified by column chromatography ($SiO_2$, 40:60 EtOAc/Hexanes) to afford 0.328 g (81%) of the product as a pale oil.

2. Synthesis of Enantiomerically Pure 4-nitrophenyl 2,2-dimethyl-3-(3,4-difluorophenyl)-5-oxo-morpholinecarboxylate (Scheme 4b)

a. (S)-(+)-O-Acetylmandelyl (±)-2,2-dimethyl-3-(3,4-difluorophenyl)-5-oxo-morpholine-3-amide To a solution of (S)-(+)-O-acetylmandelic acid (408 mg, 2.10 mmol) in $Et_2O$ (50 mL) and triethylamine (212 mg) under argon at −78° C., was added 2,2,2-trimethylacetyl chloride (272 mg, 2.10 mmol). The resulting mixture was warmed to 0° C. in ice-bath for 10 min to yield the acid chloride and it was then cooled back to −78° C. At the same time, (±)-2,2-dimethyl-3-(3,4-difluorophenyl)-6-oxo-morpholine (406 mg, 1.68 mmol) was dissolved in THF (15 mL) in another dried flask and cooled to −78° C., and n-BuLi (0.75 mL, 2.5 M) was added dropwise. The resulting solution was stirred for 10 min and was then transferred to the acid chloride via a cannula. The reaction mixture was stirred for 10 min at −78° C. and was then warmed to 0° C. and stirred for 1 hour before quenching with water (2 mL). The mixture was extracted with EtOAc (2×50 mL), dried ($Na_2SO_4$), and the solvent was evaporated. The crude product was purified by column chromatography ($SiO_2$, 15:85 to 30:70 EtOAc/Hexanes) to obtain 0.476 g of the two diastereomers as pure compounds. (combined yield: 68%) (Higher $R_f$ product: 318 mg; Lower Rf product: 158 mg).

b. (−)-2,2-Dimethyl-3-(3,4-difluorophenyl)-5-oxo-morpholine $LiOH.H_2O$ (281 mg, 6.71 mmol) was added to a solution of the amide from the previous step (Higher $R_f$ compound, 280 mg, 0.671 mmol) in THF (20 mL), $H_2O$ (2 mL) and $H_2O_2$ (5 mL). The resulting mixture was stirred vigorously for one hour. The mixture was filtered and the filtrate was extracted with EtOAc (2×50 mL), dried ($Na_2SO_4$), and the solvent was evaporated. The crude product was purified by column chromatography ($SiO_2$, 50:50 to 90:10 EtOAc/Hexanes) (0.120 g, 74%). optical rotation $[\alpha]_D=-10.0$ (c 4.5, MeOH).

c. (+)-2,2-Dimethyl-3-(3,4-difluorophenyl)-5-oxomorpholine

Prepared in the same manner as described in section III, part 2b from 150 mg of amide (lower $R_f$ compound). Yield: 65 mg (75%); $[\alpha]_D=+9.6$ (c=2.5, MeOH)

d. Enantiomerically pure 4-nitrophenyl 2,2-dimethyl-3-(3,4-difluorophenyl)-5-oxo-morpholinecarboxylate The enantiomerically pure 4-nitrophenyl-2,2-dimethyl-3-(3,4-difluorophenyl)-5-oxo-morpholinecarboxylates were prepared from (−)-2,2-dimethyl-3-(3,4-difluorophenyl)-5-oxo-morpholine and (+)-2,2-dimethyl-3-(3,4-difluorophenyl)-5-oxo-morpholine in a similar manner as described in section III, part 1d.

3. Typical Reaction Sequence for the Coupling of Side Chains ($RNH_2$) With Activated Morpholinones (Scheme 4) Synthesis of N-4-[3-(4-methoxycarbonyl-4-phenylpiperidino)propyl]-3-(3,4-difluorophenyl)-2,2-dimethyl-5-oxo-4-morpholinecarboxamide hydrochloride (Compound 15)

a. 4-Methoxycarbonyl-4-phenylpiperidine

To a stirred solution of $H_2SO_4$ (16 mL) in MeOH (400 mL), 4-phenyl-4-piperidinecarboxylic acid 4-methyl benzenesulfonate (37.7 g, 0.1 mole) was added and the mixture was stirred and refluxed for 8 hours. Excess methanol was evaporated at reduced pressure and the residue was poured into a mixture of ice and 6 N NaOH. The pH was adjusted to 10–11 by adding more 6 N NaOH and extracted with $CH_2Cl_2$ (3×150 mL). The combined $CH_2Cl_2$ extracts were dried ($MgSO_4$) and the solvent evaporated to leave the desired product as a viscous oil. The product (20.2 g, 92%) was used without further purification.

b. 3-(4-Methoxycarbonyl-4-phenylpiperidin-1-yl)propylamine

A mixture of 4-methoxycarbonyl-4-phenylpiperidine (8.5 g, 0.039 mol), 3-bromopropylamine hydrobromide (12.7 g, 0.058 mol), potassium carbonate (13.475 g, 0.0957 mole), and KI (3.24 g, 0.0195 mol) in 1,4-dioxane (200 mL) was stirred and refluxed for 24 hours. Dioxane was evaporated at reduced pressure, the residue was treated with ice-cold 6 N NaOH (400 mL) and extracted with $CH_2Cl_2$ (4×120 mL). Solvent was evaporated from the combined dried ($K_2CO_3$) extracts and the residue was purified by column chromatography on silica gel using $CHCl_3$/MeOH/2 M $NH_3$ in MeOH (20:2:1) as the eluent to afford the product as a viscous oil (7.8 g, 72%).

c. N-4-[3-(4-methoxycarbonyl-4-phenylpiperidino)propyl]-3-(3,4-difluorophenyl)-2,2-dimethyl-5-oxo-4-morpholinecarboxamide hydrochloride 4-Methylcarboxyl-4-phenyl-piperidinyl-N-propylamine (100 mg, 0.384 mmol) was added to a stirred solution of (±)-4-nitrophenyl-2,2-dimethyl-3-(3,4-difluorophenyl)-5-oxo-morpholinecarboxylate (15 mg, 0.037 mmol) in $CH_2Cl_2$ (5 mL). The resulting mixture was stirred at room temperature overnight and purified by prep. TLC on silica gel using EtOAc as the eluent to give 10 mg product (50%). The HCl salt was prepared by treatment with 1 N HCl in ether.

4. Substituted Morpholinone Example: Methyl 4-[2-([3-(3,4-difluorophenyl)-2,2-dimethyl-5-oxomorpholino]carbonylamino)ethyl]amino-1-phenyl-1-cyclohexanecarboxylate hydrochloride (cis isomer) (Compound 16)

a. 2-[4-Methoxycarbonyl-4-phenyl-cyclohexylamino]ethylamine

A mixture of 2-[4-cyano-4-phenylcyclohexylamino]ethylamine (2.34 g, 10 mmol) and concentrated sulfuric acid (20 mL) was heated at 80–85° C. for 10 hours. It was cooled to room temperature, mixed with anhydrous methanol (200 mL), and refluxed for 20 hours. Solvent was evaporated and the residue was poured onto ice (200 g) and basified to pH 11 by addition of 6 N NaOH. It was extracted with dichloromethane (4×125 mL), dried (potassium carbonate) and solvent evaporated to leave the product as an oil (2.1 g, 76%). This product was a pure mixture of cis and trans isomers. It was used in the next step without any further purification.

b. Methyl 4-[2-([3-(3,4-difluorophenyl)-2,2-dimethyl-5-oxomorpholino]carbonylamino)ethyl]amino-1-phenyl-1-cyclohexanecarboxylate hydrochloride (cis isomer)

4-Methylcarboxyl-4-phenyl-cyclohexyl-amino-ethylamine (25 mg, 0.091 mmol) was added to a stirred solution of (±)-4-nitrophenyl 2,2-dimethyl-3-(3,4-difluorophenyl)-5-oxo-morpholinecarboxylate (15 mg, 0.037 mmol) in $CH_2Cl_2$ (5 mL). The resulting mixture was stirred at RT overnight and purified by prep. TLC on silica gel using EtOAc as eluent to give 10 mg product (51%). $MH^+=544$. The HCl salt was prepared by treatment with 1 N HCl in ether.

5. Substituted Morpholinone Example: N-4-[3-{4-(2-pyridyl}piperidino)propyl]-3-(3,4-difluorophenyl)-2,2-dimethyl-5-oxo-4-morpholinecarboxanide hydrochloride (Compound 17)

a. 1-Benzyl-4-cyano-4-(2-pyridyl)piperidine

To a mixture of N,N-bis-(2-chloroethyl)benzylamine (Szarvasi, E., Eur. J. Med. Chem. Chim. Ther. 11(2), 115–124, 1976) (60 g, 22 mmol), 2-pyridylacetonitrile (2.51 mL, 22 mmol) and tetrabutylammonium hydrogen sulfate (0.26 g, 0.7 mmol) in toluene (10 mL), sodium hydroxide solution (2.43 g in 4.86 mL $H_2O$) was added over a 20 minute period. The reaction mixture was heated at 65° C. for 4 hours. The reaction mixture was cooled to room temperature, 10 mL of water was added and the solution partitioned between ethyl acetate (45 mL) and water. The organic layer was dried over sodium sulfate, filtered and concentrated. Purification of the crude product by column chromatography (hexane: EtOAc, 2:3) gave 6.2 g (87 %) of the title compound as a red solid; $^1$H-NMR (CDCl$_3$): δ 2.05 (d, J=13.1 Hz, 2H), 2.30 (t, J=13.2 Hz, 2H), 2.48 (t, J=13.2 Hz, 2 H), 2.97 (d, J=12.1 Hz, 2 H), 3.57 (s, 2 H), 7.19–7.27 (m, 6 H), 7.30 (d, J=7.6 Hz, 1 H), 7.60 (t, J=7.6 Hz, 1 H ), 8.58 (d, J=4.6 Hz, 1 H).

b. 1-Benzyl-4-carboxamido-4-(2-pyridyl)piperidine

To 1-benzyl-4-cyano-4-(2-pyridyl) piperidine (4.5 g, 14.3 mmol), 10 mL of conc. H$_2$SO$_4$ was added and the solution was stirred at room temperature for 24 hours. It was cooled to 0° C., diluted with ice pieces and poured into crushed ice. The mixture was then carefully neutralized with 50% NaOH solution. The reaction mixture was repeatedly extracted with chloroform (3×25 mL), dried over sodium sulfate, filtered and concentrated to give 4.5 g (95%) of the crude product which was used as such for the subsequent step; $^1$H-NMR (CDCl$_3$): δ 2.21 –2.28 (m, 2 H), 2.47 (s, 6 H), 3.41 (s, 2 H), 5.23 (s, 1 H), 6.40 (s, 1 H), 7.12–7.29 (m, 6 H), 7.33 (d, J=7.6 Hz, 1 H), 7.63 (t, J=7.6 Hz, 1 H), 8.55 (d, J=4.6 Hz, 1 H).

c. 1-Benzyl-4-(2-pyridyl)-piperidine

To 1-benzyl-4-carboxamido-4-(2-pyridyl)piperidine (4.5 g, 13.5 mmol) in anhydrous methanol (100 mL), HCl gas was bubbled through the solution at 0° C. for 15 minutes. The reaction mixture was then refluxed for 24 hours. It was cooled to room temperature, concentrated, neutralized with 50% NaOH and repeatedly extracted with chloroform (3×25 mL). The combined organic layer was then dried over sodium sulfate, filtered and concentrated. Flash chromatography (hexane:ethylacetate, 1:4) of the crude product yielded 1.72 g (50%) of the product as a syrup; $^1$H-NMR (CDCl$_3$): δ 1.8–1.94 (m, 4 H), 2.11 (t, J=11.4 Hz, 2 H), 2.70–2.72 (m, 1 H), 3.02 (d, J=11.4 Hz, 2 H), 3.54 (s, 2 H), 7.07–7.36 (m, 7 H), 7.58 (t, J=7.6 Hz, 1 H), 8.52 (d, J=4.6 Hz, 1 H).

d. 3-[4-(2-Pyridyl)-piperidine-1-yl]propylamine

To 1-benzyl-4-(2-pyridyl)-piperidine (3.26 g, 12.9 mmol) in dry methanol (25 mL), 10% palladium hydroxide (1.9 g) was added and the solution was hydrogenated at 200 psi for 24 hours. The solution was filtered over celite, concentrated to give 2.1 g (99%) of 4-(2-pyridyl)-piperidine which was used as such for the subsequent step. A mixture of 3-bromopropylamine hydrobromide (20 g, 91.3 mmol), potassium carbonate (37.85 g, 273.9 mmol) and di-tert-butyldicarbonate (21.90 g, 100 mmol) in methanol was stirred at room temperature for 24 hours. The reaction mixture was concentrated and partitioned between 250 mL EtOAc and 50 mL water, dried over sodium sulfate, filtered and concentrated. Purification of the crude product by column chromatography (hexane: EtOAc, 4. 5:0.5) gave 17.5 g (80%) of the product as a pale yellow oil. To a stirred solution of the 4-(2-pyridyl)-piperidine (1.86 g, 11.4 mmol) in dioxane (20 mL), N-(tert-butoxycarbonyl)-3-bromopropylamine (2.82 g, 11.4 mmol) and potassium carbonate (3.16 g, 22.9 mmol) were added and the solution was refluxed for 24 hours. The reaction mixture was cooled to room temperature, concentrated and partitioned between 40 mL chloroform and 5 mL water. The organic layer was dried over sodium sulfate, filtered and concentrated. The crude product was purified by column chromatography (ethyl acetate:methanol, 4:1) to yield 1.86 g (49%) of the required product as a colorless oil; $^1$H-NMR (CDCl$_3$): δ 1.45 (s, 9 H), 1.54–1.69 (m, 8 H), 2.21–2.68 (m, 2 H), 2.74–2.80 (m, 1 H), 3.02–3.22 (m, 4 H), 5.41 ( s, 1 H), 7.13–7.17 (m, 1 H), 7.33 (d, J=7.93 Hz, 1 H), 7.63 (t, J=7.6 Hz, 1 H), 8.54 (d, J=4.6 Hz, 1 H). To N-(tert-butoxycarbonyl)-3-[4-(2-pyridyl)-piperidin-1-yl]propylamine (0.15 g, 0.45 mmol) in 5 mL of dichloromethane, 1 mL of trifluoroacetic acid was added and the solution was stirred at room temperature for 1 hour. The solution was concentrated, neutralized with 10% KOH solution and extracted into 25 mL of dichloromethane. The organic layer was dried over sodium sulfate, filtered, and concentrated to give 0.098 g (100%) of 3-[4-2-pyridyl)-piperidin-1-yl]propylamine which was used as such for the subsequent step.

e. N-4-[3-{4-(2-pyridyl}piperidino)propyl]-3-(3,4-difluorophenyl)-2,2-dimethyl-5-oxo-4-morpholinecarboxamide hydrochloride 4-(2-Pyridinyl)piperidinyl-N-propylamine (25 mg, 0.114 mmol) was added to a stirred solution of (±)-4-nitrophenyl 2,2-dimethyl-3-(3,4-difluorophenyl)-5-oxo-morpholinecarboxylate (15 mg, 0.037 mmol) in CH$_2$Cl$_2$ (5 mL). The resulting mixture was stirred at RT overnight and purified by prep. TLC on silica gel using EtOAc as eluent to give 10 mg product (52%). MH$^+$=487. The HCl salt was prepared by treatment with 1 N HCl in ether.

6. Substituted Morpholinone Example: N-4-[3-(4-Cyan-4-phenylpiperidino)propyl]-3-(3,4-difluorophenyl)-2,2-dimethyl-5-oxo-4-morpholinecarboxamide Hydrochloride (Compound 18)

a. 3-(4-Cyano-4-phenylpiperidin-1-yl)propyl phthalimide

A mixture of 4-cyano-4-phenylpiperidine hydrochloride (111 g, 0.5 mol), 3-bromopropylphthalimide (135.39 g, 0.505 mol), potassium carbonate (276.42 g, 2 mol), and potassium iodide (5.4 g) in DMF (1 L) was stirred and heated at 100–110° C. for 8 hours. About 80% of the solvent was evaporated at reduced pressure, the residue was diluted with dichloromethane (1 L) and washed with brine (3×300 mL) and dried (Na$_2$SO$_4$). Solvent was evaporated from the dichloromethane solution and the residue was treated with isopropanol (400 mL) and cooled. The pale yellow crystalline product formed was filtered, washed with ice-cold isopropanol and dried (168.6 g, 90%); M.p. 96–98° C.

b. 3-(4-Cyano-4-phenylpiperidin-1-yl)propylamine

To a solution of 3-(4-cyano-4-phenylpiperidin-1-yl) propylphthalimide (112 g, 0.3 mol) in methanol (1.5 L), hydrazine (30 mL) was added and the mixture was stirred and refluxed for 20 hours. It was cooled, the white solid formed was filtered and washed with more methanol (200 mL). Solvent was evaporated from the filtrate and residue was dried under vacuum for 4 hours. Chloroform (500 mL) was added to this, stirred for 1 hour and filtered. The white solid was washed with more chloroform (200 mL), the solvent was evaporated from the combined filtrates to leave the product as an oil (70 g, 96%).

c. N-4-[3-(4-Cyan-4-phenylpiperidino)propyl]-3-(3,4-difluorophenyl)-2,2-dimethyl-5-oxo-4-morpholinecarboxamide hydrochloride 4-Cyan-4-phenyl-piperidinyl-N-propylamine (25 mg, 0.103 mmol) was added to a stirred solution of (±)-4-nitrophenyl 2,2-dimethyl-3-(3,4-difluorophenyl)-5-oxo-morpholinecarboxylate (15 mg, 0.037 mmol) in CH$_2$Cl$_2$(5 mL). The resulting mixture was stirred at room temperature overnight and purified by prep. TLC on silica gel using EtOAc as eluent to give 10 mg product (51%). MH$^+$=511. The HCl salt was prepared by treatment with 1 N HCl in ether.

7. Substituted Morpholinone Example: (+)- N-4-[3-(4-Cyano-4-phenylpiperidino)propyl]-3-(3,4-difluorophenyl)-2,2-dimethyl-5-oxo-4-morpholinecarboxamide Hydrochloride (Compound 18)

a. 3-(4-Cyano-4-phenylpiperidin-1-yl)propyl phthalimide

A mixture of 4-cyano-4-phenylpiperidine hydrochloride (111 g, 0.5 mol), 3-bromopropylphthalimide (135.39 g, 0.505 mol), potassium carbonate (276.42 g, 2 mol), and potassium iodide (5.4 g) in DMF (1 L) was stirred and heated at 100–110° C. for 8 hours. About 80% of the solvent was evaporated at reduced pressure, the residue was diluted with dichloromethane (1 L) and washed with brine (3×300 mL) and dried ($Na_2SO_4$). Solvent was evaporated from the dichloromethane solution and the residue was treated with isopropanol (400 mL) and cooled. The pale yellow crystalline product formed was filtered, washed with ice-cold isopropanol and dried (168.6 g, 90%); M.p. 96–98° C.

b. 3-(4-Cyano-4-phenylpiperidin-1-yl)propylamine

To a solution of 3-(4-cyano-4-phenylpiperidin-1-yl)propylphthalimide (112 g, 0.3 mol) in methanol (1.5 L), hydrazine (30 mL) was added and the mixture was stirred and refluxed for 20 hours. It was cooled, the white solid formed was filtered and washed with more methanol (200 mL). Solvent was evaporated from the filtrate and residue was dried under vacuum for 4 hours. Chloroform (500 mL) was added to this, stirred for 1 hour and filtered. The white solid was washed with more chloroform (200 mL), the solvent was evaporated from the combined filtrates to leave the product as an oil (70 g, 96%).

c. (+)-N-4-[3-(4-Cyano-4-phenylpiperidino)propyl]-3-(3,4-difluorophenyl)-2,2-dimethyl-5-oxo-4-morpholinecarboxamide hydrochloride 4-Cyano-4-phenyl-piperidinyl-N-propylamine (40 mg, 0.165 mmol) was added to a stirred solution of (−)-4-nitrophenyl 2,2-dimethyl-3-(3,4-difluorophenyl)-5-oxo-morpholinecarboxylate (15 mg, 0.037 mmol) in $CH_2Cl_2$ (5 mL). The resulting mixture was stirred at room temperature overnight and purified by prep. TLC on silica gel using EtOAc as the eluent to give 16 mg product (85%). $[\alpha]_D$=+26.3 (c=0.8, $CH_2Cl_2$). MH$^+$=511. The HCl salt was prepared by treatment with 1 N HCl in ether.

8. Substituted Morpholinone Example: (−)- N4-[3-(4-Cyano-4-phenylpiperidino)propyl]-3-(3,4-difluorophenyl)-2,2-dimethyl-5-oxo-4-morpholinecarboxamide Hydrochloride (Compound 18)

a. 3-(4-Cyano-4-phenylpiperidin-1-yl)propyl phthalimide

A mixture of 4-cyano-4-phenylpiperidine hydrochloride (111 g, 0.5 mol), 3-bromopropylphthalimide (135.39 g, 0.505 mol), potassium carbonate (276.42 g, 2 mol), and potassium iodide (5.4 g) in DMF (1 L) was stirred and heated at 100–110° C. for 8 hours. About 80% of the solvent was evaporated at reduced pressure, the residue was diluted with dichloromethane (1 L) and washed with brine (3×300 mL) and dried ($Na_2SO_4$). Solvent was evaporated from the dichloromethane solution and the residue was treated with isopropanol (400 mL) and cooled. The pale yellow crystalline product formed was filtered, washed with ice-cold isopropanol and dried (168.6 g, 90%); M.p. 96–98° C.

b. 3-(4-Cyano-4-phenylpiperidin-1-yl)propylamine

To a solution of 3-(4-cyano-4-phenylpiperidin-1-yl)propylphthalimide (112 g, 0.3 mol) in methanol (1.5 L), hydrazine (30 mL) was added and the mixture was stirred and refluxed for 20 hours. It was cooled, the white solid formed was filtered and washed with more methanol (200 mL). Solvent was evaporated from the filtrate and residue was dried under vacuum for 4 hours. Chloroform (500 mL) was added to this, stirred for 1 hour and filtered. The white solid was washed with more chloroform (200 mL), the solvent was evaporated from the combined filtrates to leave the product as an oil (70 g, 96%).

c. (−)- N4-[3-(4-Cyano-4-phenylpiperidino)propyl]-3-(3,4-difluorophenyl)-2,2-dimethyl-5-oxo-4-morpholinecarboxamide hydrochloride 4-Cyano-4-phenyl-piperidinyl-N-propylamine (40 mg, 0.165 mmol) was added to a stirred solution of (+)-4-nitrophenyl 2,2-dimethyl-3-(3,4-difluorophenyl)-5-oxo-morpholinecarboxylate (15 mg, 0.037 mmol) in $CH_2Cl_2$ (5 mL). The resulting mixture was stirred at room temperature overnight and purified by prep. TLC with EtOAc as eluent to give 14 mg product (74%). $[\alpha]_D$=−25.7 (c=0.7, $CH_2Cl_2$). MH$^+$=511. The HCl salt was prepared by treatment with 1 N HCl in ether.

9. Substituted Morpholinone Example: 3-(3,4-Difluorophenyl)-2,2-dimethyl-5-oxo-morpholine-4-carboxylic acid-{2-[4-(2-pyridyl)piperidin-1-yl]-1-methyl-ethyl}-amide Hydrochloride (Compound 19)

a. N-(tert-Butoxycarbonyl)-L-alanine 4-(2-pyridyl)piperidin-1-yl amide

To a solution of N-(tert-butoxycarbonyl)-L-alanine (1.485 g, 7.847 mmol) and 4-(2-pyridyl)piperidine (0.910 g, 5.60 mmol) in dichloromethane (20 mL) at 0° C., was added N,N-dimethylaminopyridine (DMAP, 2.05 g, 16.8 mmol) and 1-(3-dimethylaminopropyl)3-ethylcarbodiimide hydrochloride (DMAPECD, 2.147 g, 11.2 mmol). The resulting mixture was stirred overnight while warmed up to room temperature. The reaction mixture was quenched with aqueous $NH_4Cl$ (30 mL) and extracted with $CH_2Cl_2$ (30 mL×2). The combined extracts were dried ($K_2CO_3$), concentrated, and purified by flash chromatography on silica gel (100% EtOAc) to obtain 2.09 g (80%) of N-(tert-Butoxycarbonyl)-L-alanine 4-(2-pyridyl)piperidin-1-yl amide.

b. (S)-N-(tert-Butoxycarbonyl)amino-3-[4-(2-pyridyl)piperidin-1-yl]propane

To a solution of N-(tert-butoxycarbonyl)-L-alanine 4-(2-pyridyl)piperidin-1-yl amide (0.650 g, 1.95 mmol) in THF (20 mL) at 0° C. was added LAH (4.0 mL, 1.0 M in THF) dropwise. The resulting mixture was stirred for 3 hours before quenching with 1 mL of $H_2O$ and 5 mL of 1 N NaOH. The mixture was extracted with $CH_2Cl_2$ (30 mL×2). The combined extracts were dried ($K_2CO_3$), concentrated, and purified by flash chromatography on silica gel (chloroform:MeOH:2.0 M $NH_3$ in MeOH=100:5:1) to afford the product (0.479 g, 77%) as a colorless oil.

c. (S)-Amino-3-[4-(2-pyridyl)piperidin-1-yl]propane

A solution of (S)-N-(tert-butoxycarbonyl)amino-3-[4-(2-pyridyl)piperidin-1-yl]propane (0.460 g, 1.44 mmol) in $CH_2Cl_2$ (10 mL) and TFA (5 mL) was stirred for 12 hours at room temperature. The mixture was concentrated at reduced pressure and the residue was washed with 20% NaOH, and extracted with extracted with $CH_2Cl_2$ (50 mL×2). The combined extracts were dried ($K_2CO_3$), concentrated to yield the product (0.209 g, 66%) without further purification.

d. 3-(3,4-Difluorophenyl)-2,2-dimethyl-5-oxo-morpholine-4-carboxylic acid-{2-[4-(2-pyridyl) piperidin-1-yl]-1- methyl-ethyl}-amide hydrochloride (Compound 19)

4-(2-Pyridinyl)piperidinyl-N-(1-methyl)ethylamine (25 mg, 0.114 mmol) was added to a stirred solution of (±)-4-nitrophenyl 2,2-dimethyl-3-(3,4-difluorophenyl)-5-oxo-morpholinecarboxylate (15 mg, 0.037 mmol) in $CH_2Cl_2$ (5 mL). The resulting mixture was stirred at room temperature overnight and purified by prep. TLC on silica gel using EtOAc as eluent to give 10 mg product (55%). $MH^+$=487. The HCl salt was prepared by treatment with 1 N HCl in ether.

10. Substituted Morpholinone Example: N-4-(2-[1-(2,4-Difluorobenzoyl)-4-piperidyl]aminoethyl)-3-(3,4-difluorophenyl)-2,2-dimethyl-5-oxo-4-morpholinecarboxamide Hydrochloride (Compound 20) (Scheme 5)

a. 4-(2,4-Difluorobenzoyl)piperidinone

To a suspension of 4-piperidinone monohydrate hydrochloride (2.00 g, 13.28 mmol) in $CH_2Cl_2$ (40 mL) and triethylamine (5.0 mL) was added 2,4-difluorobenzoyl chloride (2.84 g, 15.93 mmol). The resulting mixture was stirred at room temperature for 5 hours before quenching with aqueous $NaHCO_3$ (30 mL). Extracted with EtOAc (3×50 mL), dried ($MgSO_4$), and concentrated to a residue which was purified by flash chromatography (EtOAc:Hexanes 9:1 to 1:1 ) afford product as an oil (2.25 g, 71%).

b. 2-{[4-(2,4-Difluorobenzoyl)piperidinyl]amino}ethylamine

A solution of 4-(2,4-difluorobenzoyl)piperidinone (1.50 g, 6.27 mmol) in benzene (40 mL) and ethylenediamine (4.0 mL) was refluxed for 6 hours. The resulting mixture was concentrated to a residue which was dissolved in MeOH (30 mL). The mixture was cooled (0° C.) and $NaBH_4$ (1.0 g, 26.4 mmol) was slowly added. After stirred for an hour, the mixture was concentrated and quenched with 1 N NaOH (50 mL). The mixture was extracted with $CH_2Cl_2$ (5×20 mL), dried ($K_2CO_3$), and was concentrated. The residue was purified by flash chromatography ($CHCl_3$-MeOH-2 M $NH_3$ in MeOH 100:10:2 to 100:20:5) to afford the product as an pale yellow solid (670 mg, 38%).

c. 3-(3,4-Difluorophenyl)-2,2-dimethyl-5-oxo-morpholine-4-carboxylic acid-{2-[1-(2,4-difluoro benzoylpiperidin-4-yl]-aminoethylamide hydrochloride 4-N-(2,4-Difluorobenzoyl)-piperidinyl-aminoethylamine (25 mg, 0.088 mmol) was added to a stirred solution of (±)-4-nitrophenyl 2,2-dimethyl-3-(3,4-difluorophenyl)-5-oxo-morpholinecarboxylate (15 mg, 0.037 mmol) in $CH_2Cl_2$ (5 mL). The resulting mixture was stirred at room temperature overnight and purified by prep. TLC on silica gel using EtOAc as eluent to give 10 mg product (49%). $MH^+$=551. The HCl salt was prepared by treatment with 1 N HCl in ether.

IV. Synthesis of Morpholine Example (Scheme 6)

1. Synthesis of 3-(3,4-difluoro-phenyl)-morpholine-4-carboxylic Acid[3-(4,4-diphenyl-piperidin-1-yl)-propyl]-amide (Compound 21)

a. 3-(3,4-Difluoro-phenyl)-morpholine

To a suspension of $LiAlH_4$ (6.0 mmol, 0.23 g) in 25.0 mL of $Et_2O$ was added a solution of 5-(3,4-difluoro-phenyl)-morpholin-3-one (2.0 mmol, 0.42 g) in 20.0 mL $Et_2O$ and 5.0 mL THF at room temperature. The resulting suspension was heated to reflux for 2 hours and was then quenched with water and aq. NaOH solution. The solid was filtered off and the filtrate was dried over $Na_2SO_4$. The filtrate was then decanted and the solvent was removed in vacuo to obtain 5-(3,4-difluoro-phenyl)morpholine as a viscous oil. It was converted to its hydrochloride salt for its analysis. Yellow powder. M.P.=171–173° C.; Mass spec. 200 (M+1, 100%). Analysis calculated for $C_{10}H_{12}NOF_2Cl.0.5$ acetone: C, 51.96; H, 5.61; N, 5.41. Found: C, 51.98; H, 5.70; N, 5.34.

b. 3-(4,4-Diphenyl-piperidin-1-yl)-propyl]-carbamic acid-4-nitro-phenyl ester

To a solution containing 3-(4,4-diphenyl-piperidin-1-yl)-propylamine (0.8 mmol, 0.24 g) and triethylamine (0.96 mmol, 0.13 mL) in 10 mL of THF was added 4-nitrophenylchloroformate (0.94 mmol, 0.19 g) at 0° C. The solution was allowed to reach room temperature over 1 hour. The solvent was removed and the product was passed through a short silica gel column with EtOAc as an eluent (Rf=0.25). 3-(4,4-Diphenyl-piperidin-1-yl)propyl]-carbamic acid-4-nitro-phenyl ester was obtained as a yellow oil which was immediately used in the next step.

c. 3-(3,4-Difluoro-phenyl)-morpholine-4-carboxylic acid [3-(4,4-diphenyl-piperidin-1-yl)-propyl]-amide To a solution of 3-(4,4-diphenyl-piperidin-1-yl)propyl]-carbamic acid-4-nitro-phenyl ester (0.35 mmol, 150 mg) in 10.0 mL THF was added 3-(3,4-difluorophenyl)-morpholine (0.4 mmol, 50 mg) at room temperature. The solvent was removed in vacuo and the residue was subjected to silica gel column chromatography (8:1 EtOAc/MeOH as the eluting system). 3-(3,4-Difluoro-phenyl)-morpholine-4-carboxylic acid[3-(4,4-diphenyl-piperidin-1-yl)-propyl]-amide was obtained as a pale yellow oil which was converted into its hydrochloride salt by treatment with 1 N HCl in ether (34 mg, 61%). Yellow sticky solid. M.P.=71–74° C.; Mass spec. 520 (M+1, 100%); Analysis calculated for $C_{31}H_{36}N_3O_2F_2Cl.0.8\ CH_2Cl_2$: C, 61.21; H, 6.07; N, 6.73. Found: C, 61.45; H, 6.35; N, 6.27.

V. General Syntheses of Morpholinones and Morpholines

The examples described in Sections I–IV are merely illustrative of the methods used to synthesize morpholine and morpholinone derivatives. Further derivatives may be obtained utilizing the methods shown in Schemes 7–22. The substituents in Schemes 7–22 are described in the Detailed Description.

It may be necessary to incorporate protection and deprotection strategies for substituents such as amino, amido, carboxylic acid, and hydroxyl groups in the synthetic methods described above to form morpholine and morpholinone derivatives. Methods for protection/deprotection of such groups are well-known in the art, and may be found, for example in Greene, T. W. and Wuts, P. G. M. (1991) *Protective Groups in Organic Synthesis. 2nd Edition* John Wiley & Sons, New York.

VI. Oral Composition

As a specific embodiment of an oral composition of a compound of this invention, 100 mg of one of the compounds described herein is formulated with sufficient finely divided lactose to provide a total amount of 580 to 590 mg to fill a size O hard gel capsule.

VII. Pharmacological Profiles of the Compounds in Cloned Human Adrenergic Receptors Binding affinities were measured for selected compounds of the invention at six cloned human $\alpha_1$ and $\alpha_2$ receptor subtypes, as well as at the L-type calcium channel. The protocols for these experiments are given below.

1. Protocol for the Determination of the Potency of $\alpha_1$ Antagonists

The activity of compounds at the different human receptors was determined in vitro using cultured cell lines that selectively express the receptor of interest. These cell lines were prepared by transfecting the cloned cDNA or cloned genomic DNA or constructs containing both genomic DNA and cDNA encoding the human a-adrenergic receptors as follows:

$\alpha_{1d}$ Human Adrenergic Receptor:

The entire coding region of $\alpha_{1d}$ (1719 bp), including 150 base pairs of 5' untranslated sequence (5' UT) and 300 bp of 3' untranslated sequence (3' UT), was cloned into the BamHI and ClaI sites of the polylinker-modified eukaryotic expression vector pCEXV-3, called EXJ.HR. The construct involved the ligation of partial overlapping human lymphocyte genomic and hippocampal cDNA clones: 5' sequence were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid α1A/EXJ (expression vector containing the $\alpha_{1a}$ receptor gene (old nomenclature)) and the plasmid pGCcos3neo (plasmid containing the aminoglycoside transferase gene) into LM(tk–) cells using calcium phosphate technique. The cells were grown, in a controlled environment (37° C., 5% $CO_2$), as monolayers in Dulbecco's modified Eagle's Medium (GIBCO, Grand Island, N.Y.) containing 25 mM glucose and supplemented with 10% bovine calf serum, 100 units/ml penicillin g, and 100 μg/ml streptomycin sulfate. Stable clones were then selected for resistance to the antibiotic G-418 (1 mg/ml), and membranes were harvested and assayed for their ability to bind [$^3$H] prazosin as described below (see "Radioligand Binding assays").

The cell line expressing the human $\alpha_{1d}$ receptor used herein was designated L-$\alpha_{1A}$ (old nomenclature) and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. The cell line expressing the human $\alpha_{1d}$ receptor, was accorded ATCC Accession No. CRL 11138, and was deposited on Sep. 25, 1992.

$\alpha_{1b}$ Human Adrenergic Receptor:

The entire coding region of $\alpha_{1b}$ (1563 bp), including 200 base pairs and 5' untranslated sequence (5' UT) and 600 bp of 3' untranslated sequence (3' UT), was cloned into the EcoRI site of pCEXV-3 eukaryotic expression vector. The construct involved ligating the full-length containing EcoRI brainstem cDNA fragment from λ ZapII into the expression vector. Stable cell lines were selected as described above. The cell line used herein was designated L-$\alpha_{1B}$ and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. The cell line L-$\alpha_{1B}$ was accorded ATCC Accession No. CR 11139, on Sep. 29, 1992.

$\alpha_{1a}$ Human Adrenergic Receptor:

The entire coding region of $\alpha_{1a}$ (1401 bp), including 400 base pairs of 5' untranslated sequence (5' UT) and 200 bp of 3' untranslated sequence (3' UT), was cloned into the KpnI site of the polylinker-modified pCEXV-3-derived eukaryotic expression vector, EXJ.RH. The construct involved ligating three partial overlapping fragments: a 5' 0.6 kb HincII genomic clone, a central 1.8 EcoRI hippocampal cDNA clone, and a 3' 0.6Kb PstI genomic clone. The hippocampal cDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were selected as described above. The stable cell line expressing the human $\alpha_{1a}$ receptor used herein was designated L-$\alpha_{1c}$ (old nomenclature) and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. The cell line expressing the human $\alpha_{1a}$ receptor was accorded Accession No. CR 11140, on Sep. 25, 1992.

Radioligand Binding Assays for $\alpha_1$ receptors:

Transfected cells from culture flasks were scraped into 5 ml of 5 mM Tris-HCl, 5 mM EDTA, pH 7.5, and lysed by sonication. The cell lysates were centrifuged at 1000 rpm for 5 min at 4° C., and the supernatant was centrifuged at 30,000×g for 20 min at 4° C. The pellet was suspended in 50 mM Tris-HCl, 1 mM $MgCl_2$, and 0.1% ascorbic acid at pH 7.5. Binding of the $\alpha_1$ antagonist [$^3$H]prazosin (0.5 nM, specific activity 76.2 Ci/mmol) to membrane preparations of LM(tk–) cells was done in a final volume of 0.25 ml and incubated at 37° C. for 20 min. Nonspecific binding was determined in the presence of 10 μg phentolamine. The reaction was stopped by filtration through GF/B filters using a cell harvester. Inhibition experiments, routinely consisting of 7 concentrations of the tested compounds, were analyzed using a non-linear regression curve-fitting computer program to obtain Ki values.

$\alpha_2$ Human Adrenergic Receptors:

To determine the potency of $\alpha_1$ antagonists at the $\alpha_2$ receptors, LM(tk–) cell lines stably transfected with the genes encoding the $\alpha_{2a}$, $\alpha_{2b}$, and $\alpha_{2c}$ receptors were used. The cell line expressing the $\alpha_{2a}$ receptor is designated L-$\alpha_{2A}$, and was deposited on Nov. 6, 1992 under ATCC Accession No. CRL 11180. The cell line expressing the $\alpha_{2b}$ receptor is designated L-NGC-$\alpha_{2B}$, and was deposited on Oct. 25, 1989 under ATCC Accession No. CRL10275. The cell line expressing the $\alpha_{2c}$ receptor is designated L-$\alpha_{2C}$, and was deposited on Nov. 6, 1992 under ATCC Accession No. CRL-11181. All the cell lines were deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. Cell lysates were prepared as described above (see Radioligand Binding Assays), and suspended in 25 mM glycylglycine buffer (pH 7.6 at room temperature). Equilibrium competition binding assay were performed using [3H] rauwolscine (0.5 nM), and nonspecific binding was determined by incubation with 10 μM phentolamine. The bound radioligand was separated by filtration through GF/B filters using a cell harvester.

Determination of the Activity of $\alpha_1$ Antagonists at Calcium Channels:

The potency of $\alpha_1$ antagonists at calcium channels may be determined in competition binding assays of [3H]

nitrendipine to membrane fragments of rat cardiac muscle, essentially as described by Glossman and Ferry (Methods in Enzymology 109:513–550, 1985). Briefly, the tissue is minced and homogenized in 50 mM Tris-HCl (pH 7.4) containing 0.1 mM phenylmethylsulfonyl fluoride. The homogenates are centrifuged at 1000 g for 15 minutes, and the resulting supernatant centrifuged at 45,000 g for 15 minutes. The 45,000 g pellet is suspended in buffer and centrifuged a second time. Aliquots of membrane protein are then incubated for 30 minutes at 37° C. in the presence of [3H]nitrendipine (1 nM), and nonspecific binding determined in the presence of 10 μg nifedipine. The bound radioligand is separated by filtration through GF/B filters using a cell harvester.

The compounds described above were assayed using cloned human alpha adrenergic receptors. The preferred compounds were found to be selective $\alpha_{1a}$ antagonists. The binding affinities of several compounds are illustrated in the following table.

Binding affinities of selected compounds of the present invention at cloned human $\alpha_{1d}$, $\alpha_{1b}$ and $\alpha_{1a}$ receptors. (h=human)

| Compound | h$\alpha_{1d}$ $K_i$ (nM) | h$\alpha_{1b}$ $K_i$ (nM) | h$\alpha_{1a}$ $K_i$ (nM) |
| --- | --- | --- | --- |
| 1 | 306.7 | 243.6 | 1.6 |
| 4 | 3162.3 | 3630.8 | 32.0 |
| 7 | 204.2 | 245.5 | 12.6 |
| 14 | 4200.8 | 1456.6 | 2.6 |
| 17 | 579.9 | 464.2 | 3.8 |

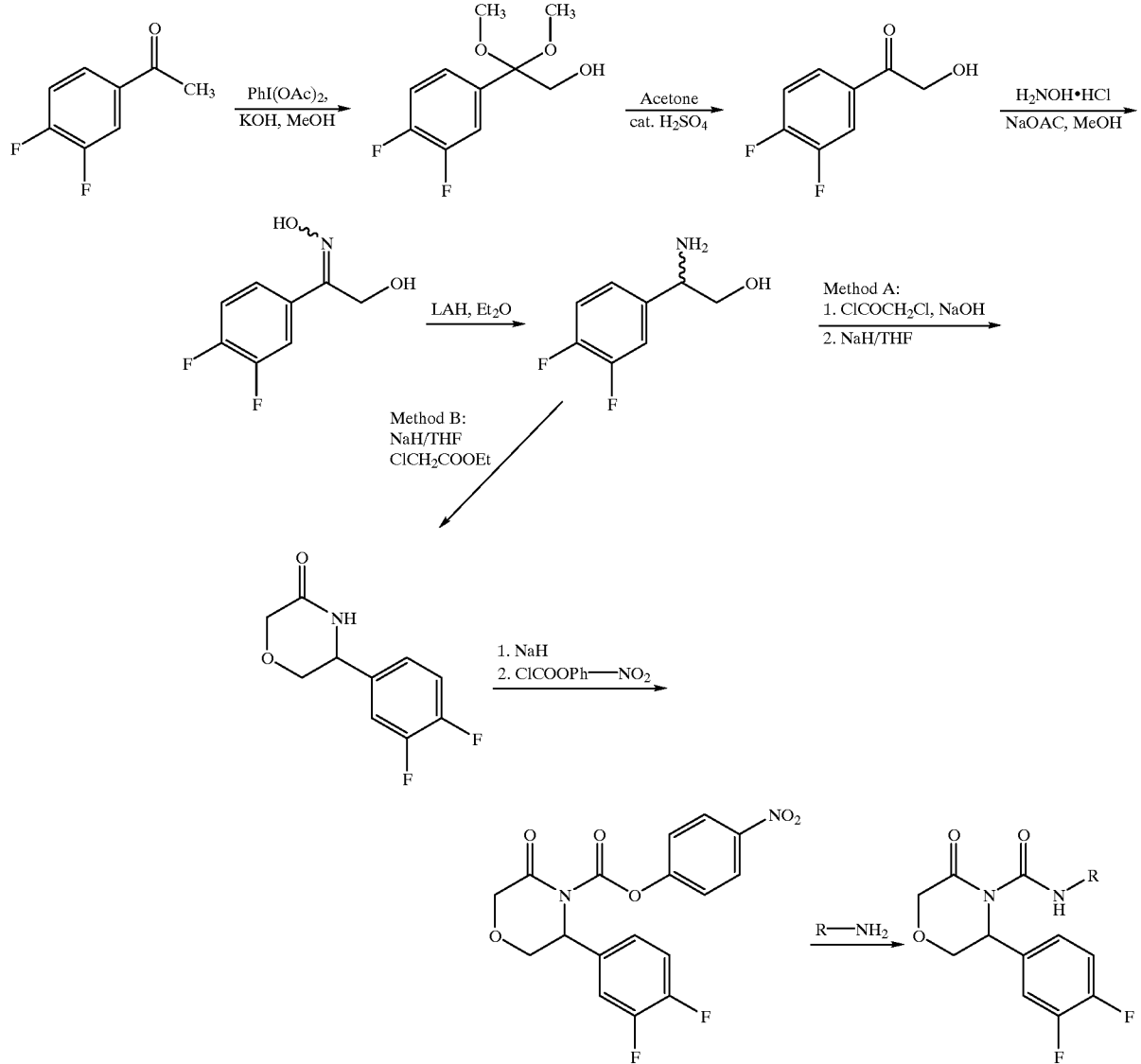

Scheme 1
Synthesis of Morpholinone Examples

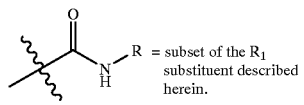
Scheme 2
Synthesis of Chiral Morpholinone Examples
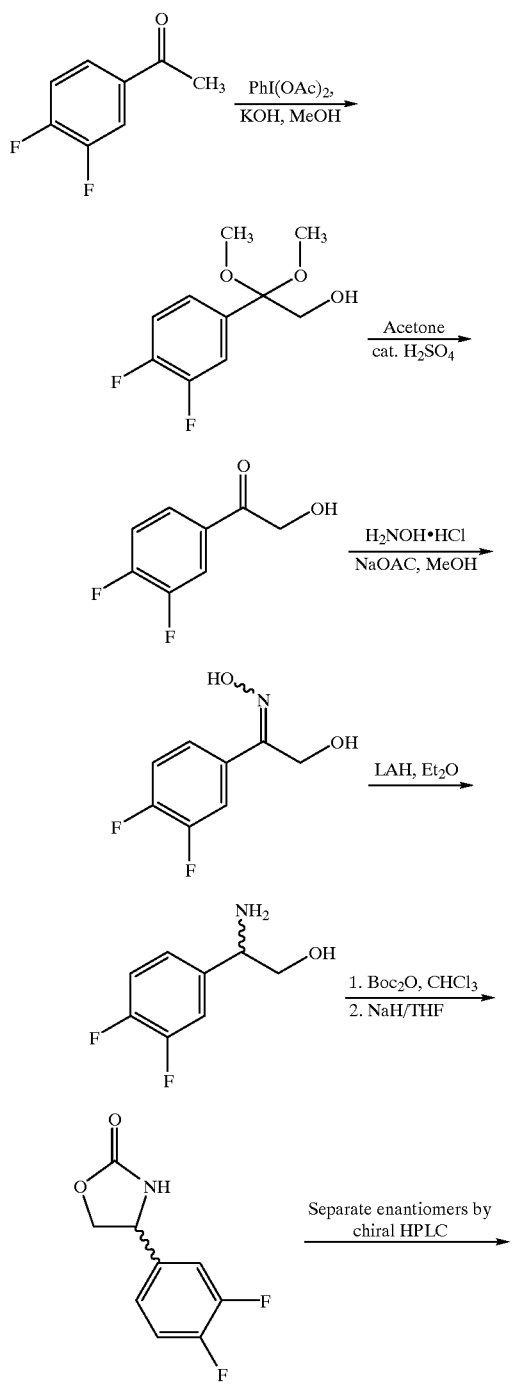
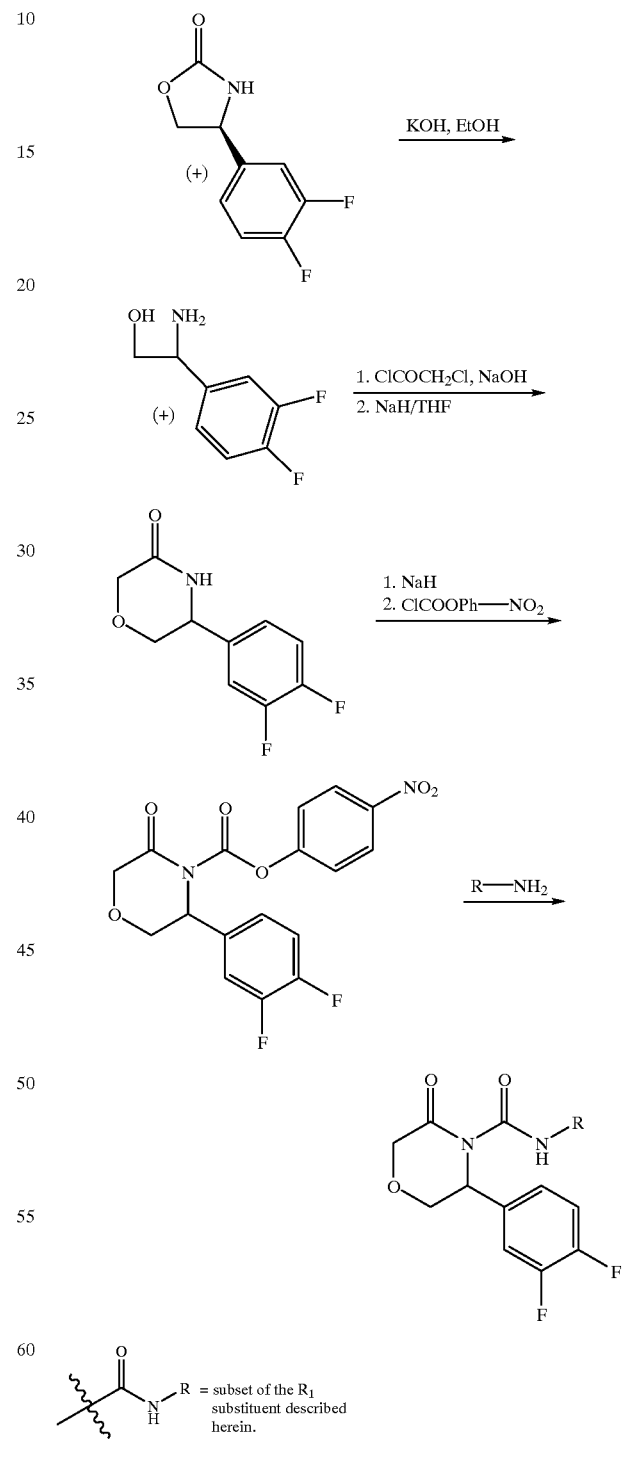

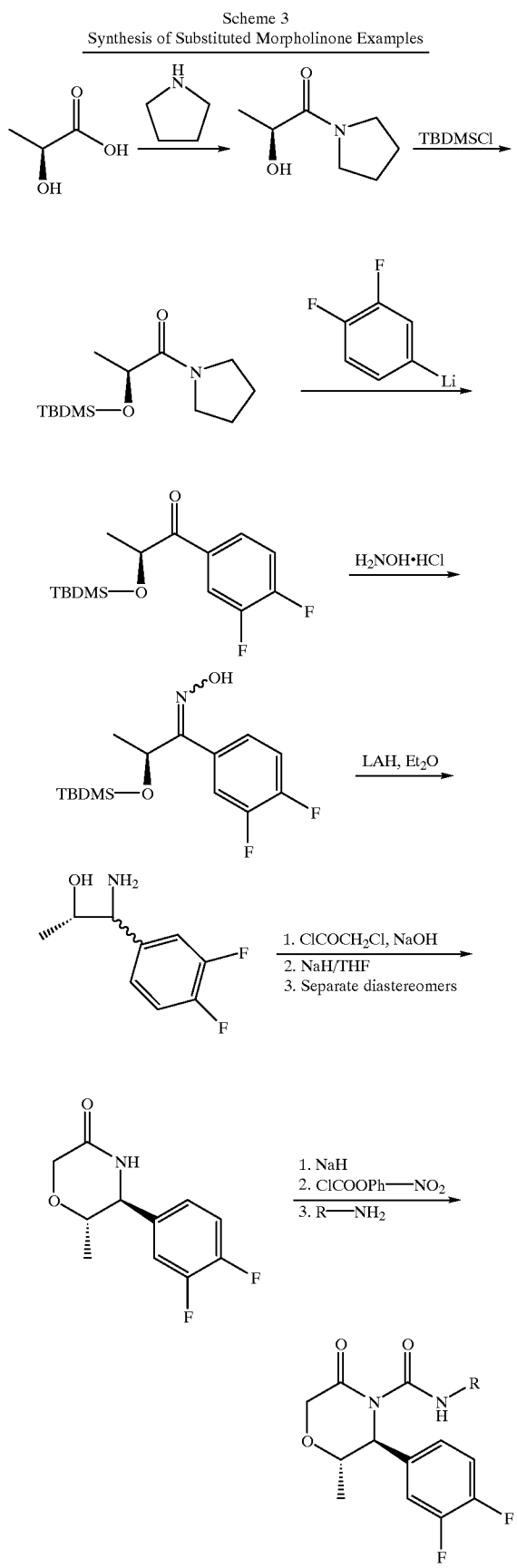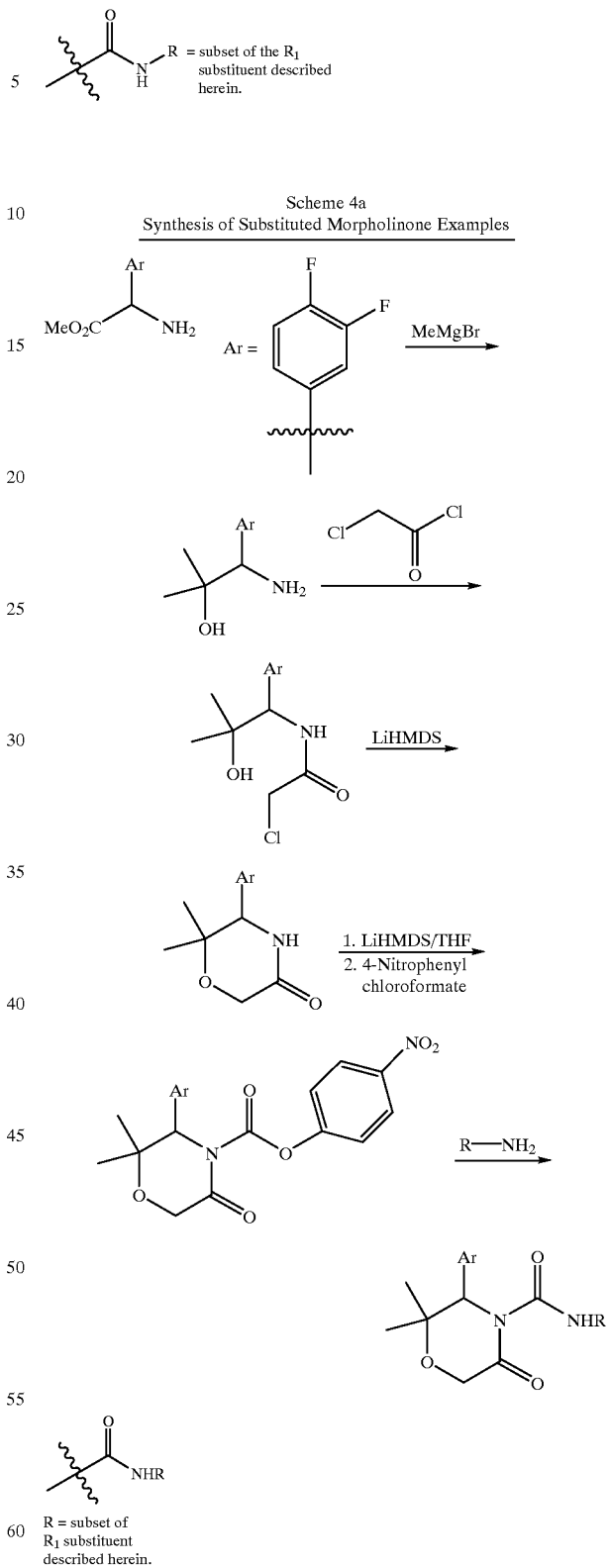

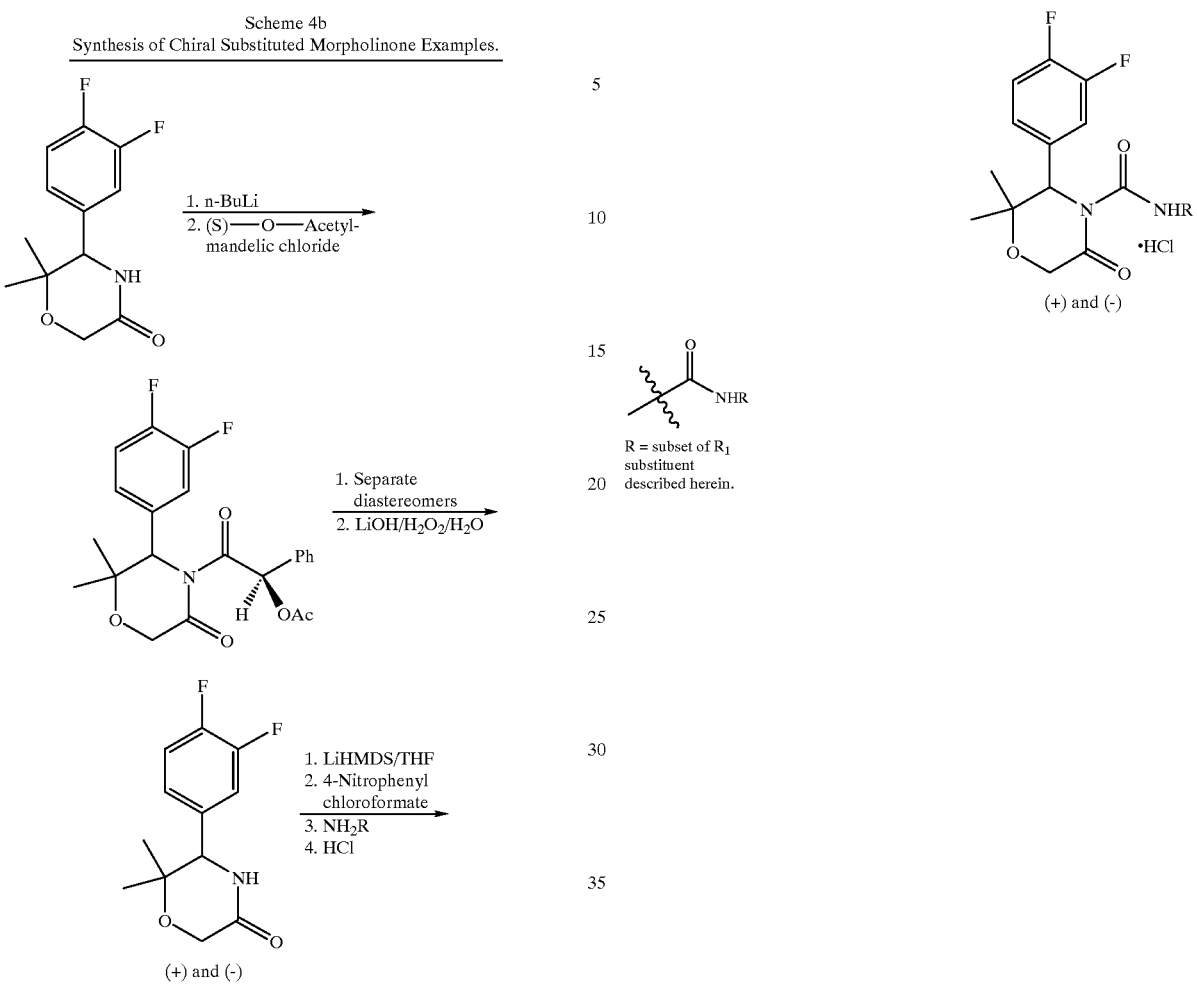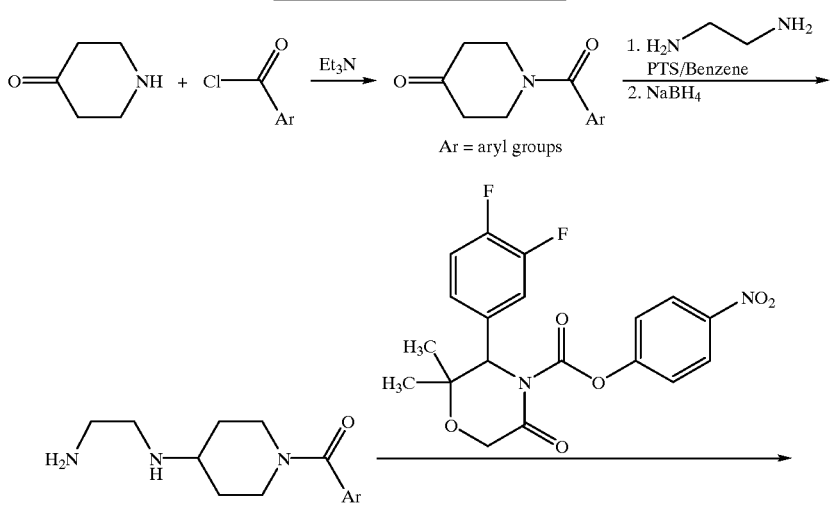

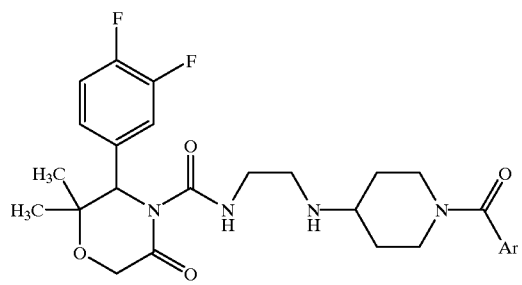
Scheme 6
Synthesis of Morpholine Example (Compound 21).
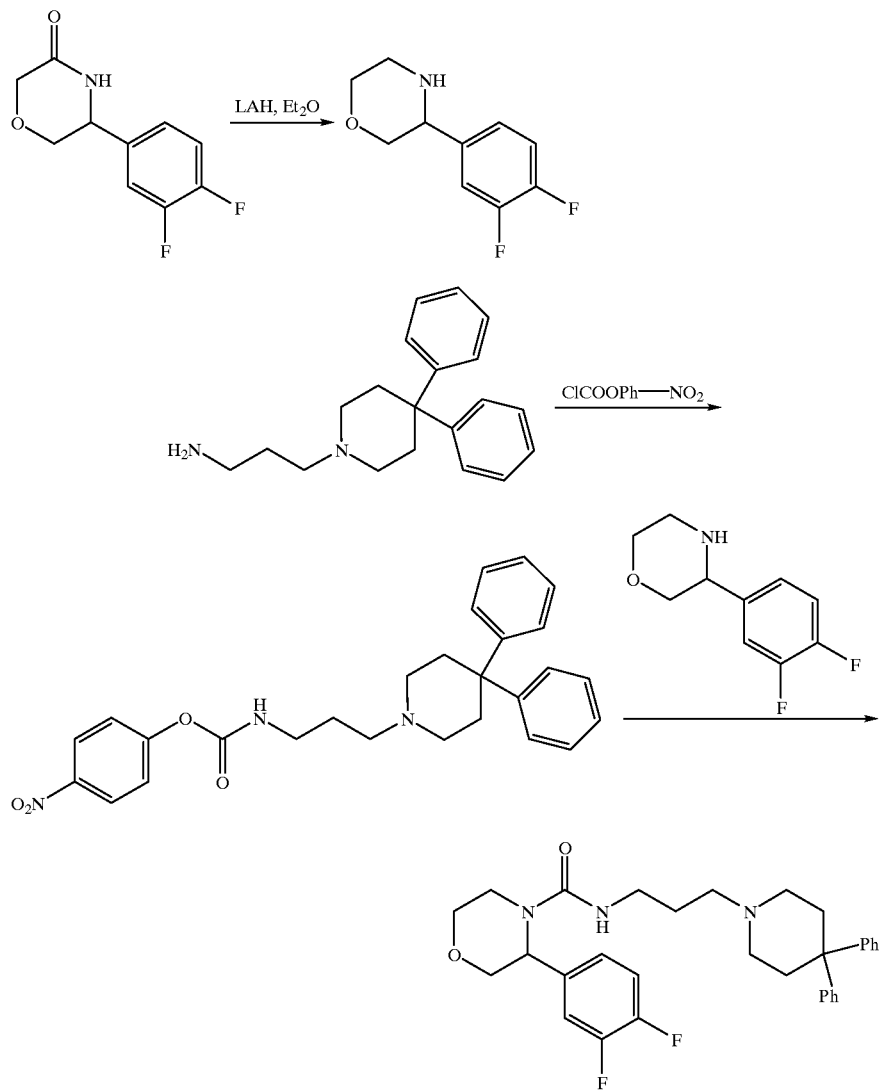

Scheme 7
General Synthesis of Substituted Morpholinones.
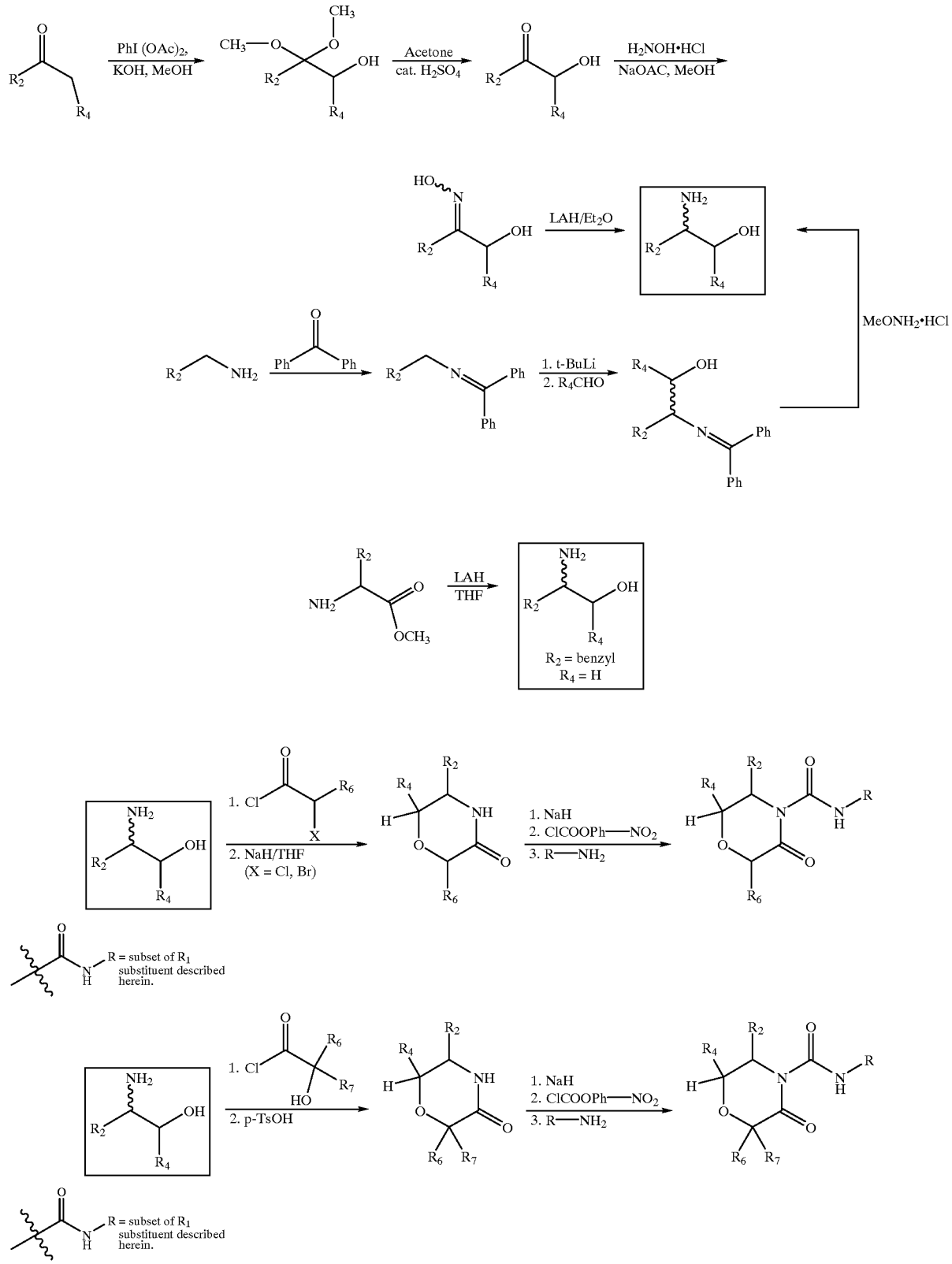

Scheme 8
General Synthesis of Substituted Morpholinones.
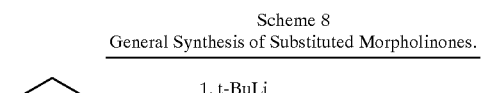
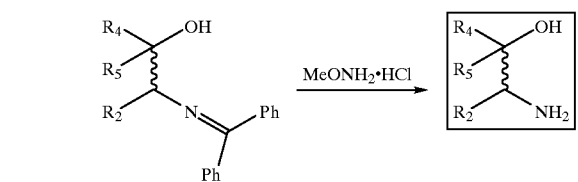
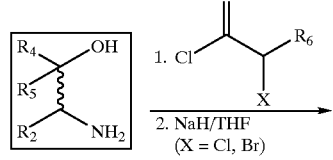
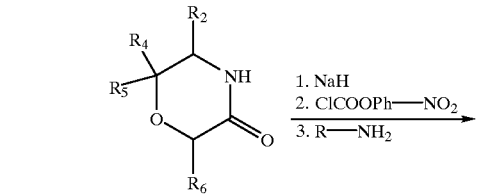
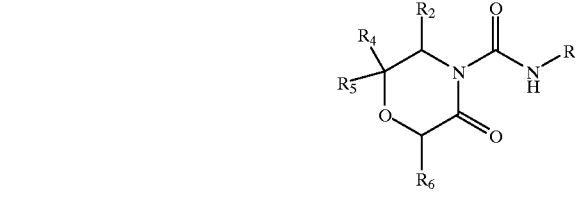
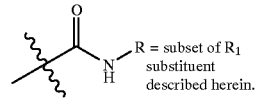
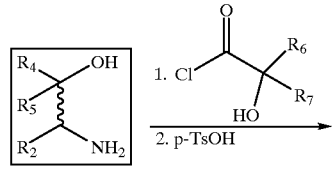
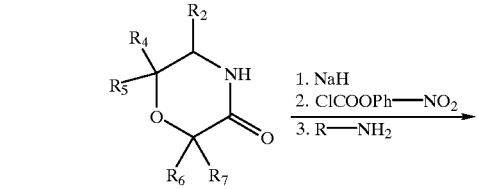
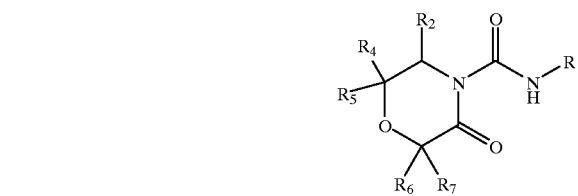
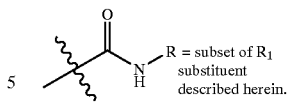
Scheme 9
General Synthesis of Substituted Morpholinones.
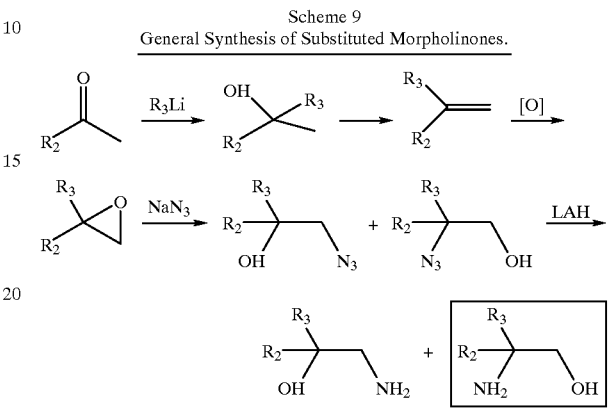
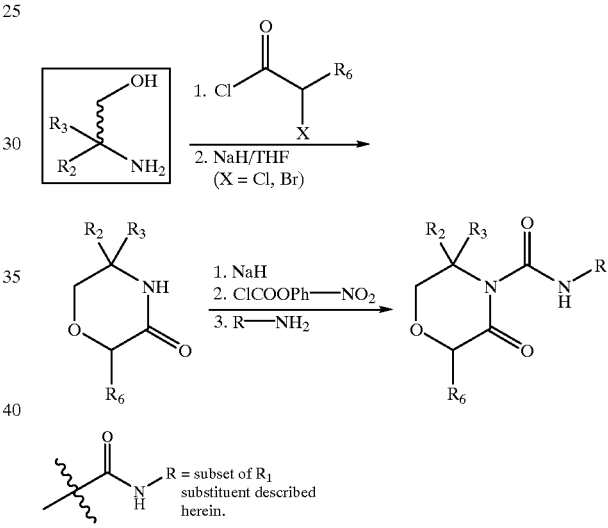
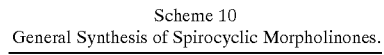
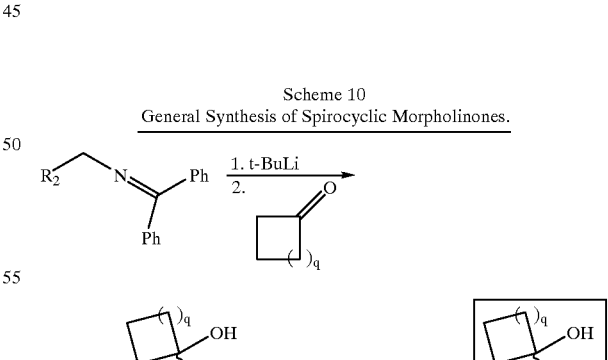
Scheme 10
General Synthesis of Spirocyclic Morpholinones.
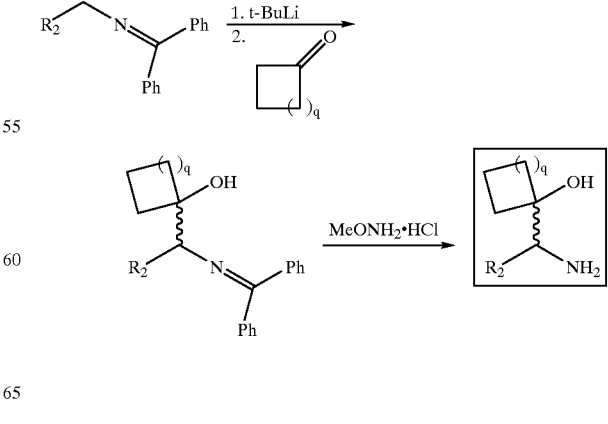

-continued
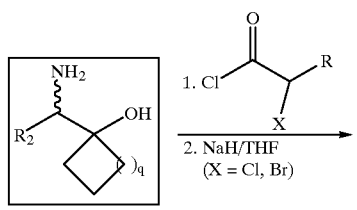
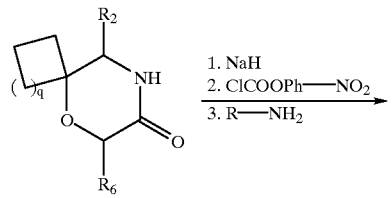
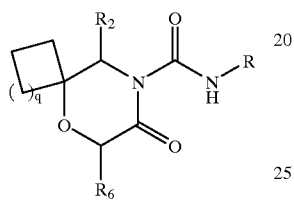
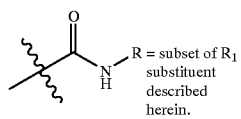
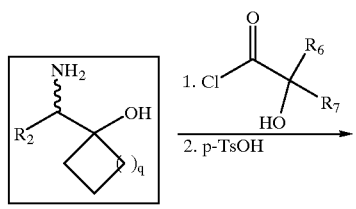
-continued
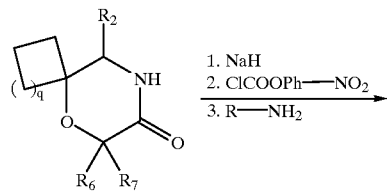
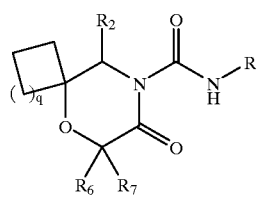
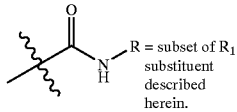
Scheme 11
General Synthesis of Thiomorpholinones.
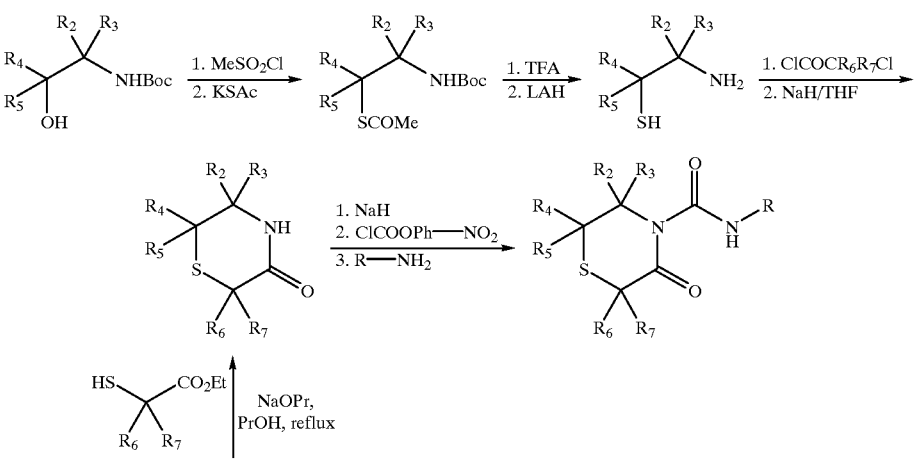

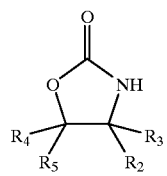
(Ref. Ishibashi, et al. Synlett, 1997, 915)
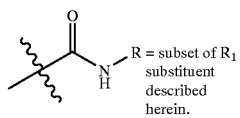
R = subset of $R_1$ substituent described herein.
Scheme 12
General Synthesis of Morpholines and Thiomorpholines.
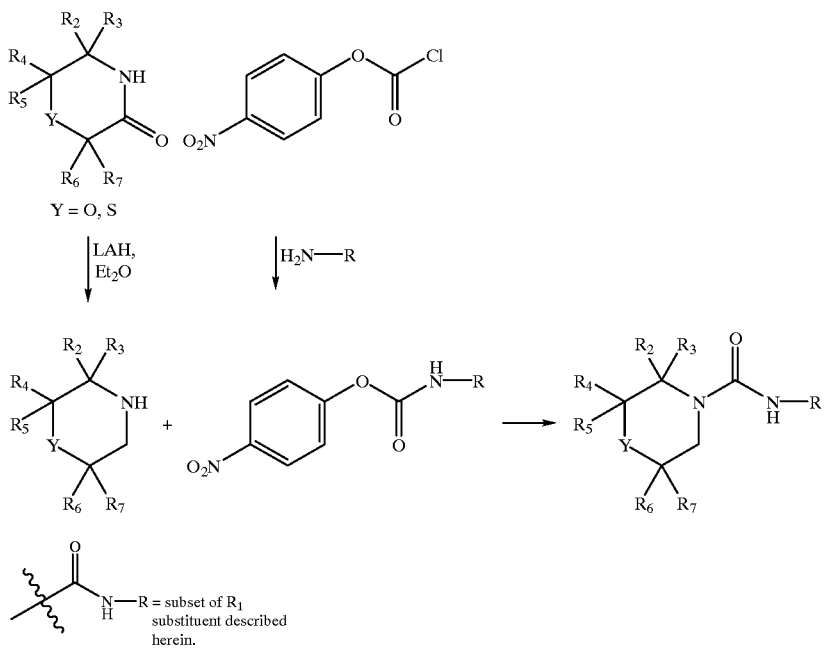
R = subset of $R_1$ substituent described herein.
Scheme 13
General Synthesis of Piperizines and piperizinones.
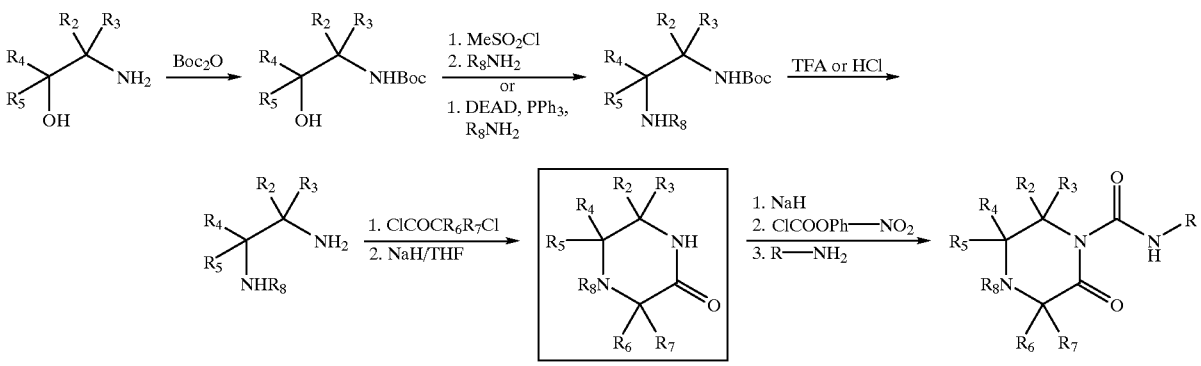

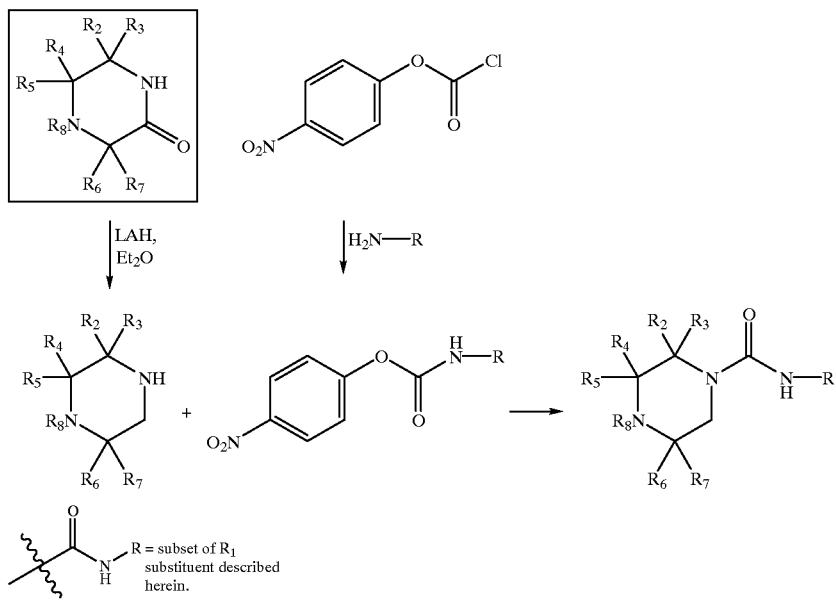
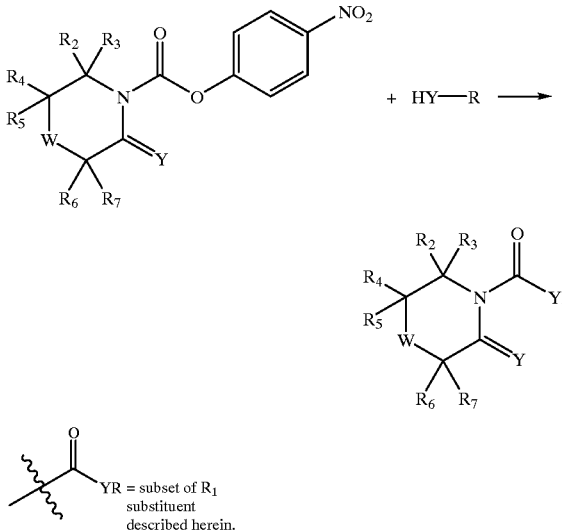
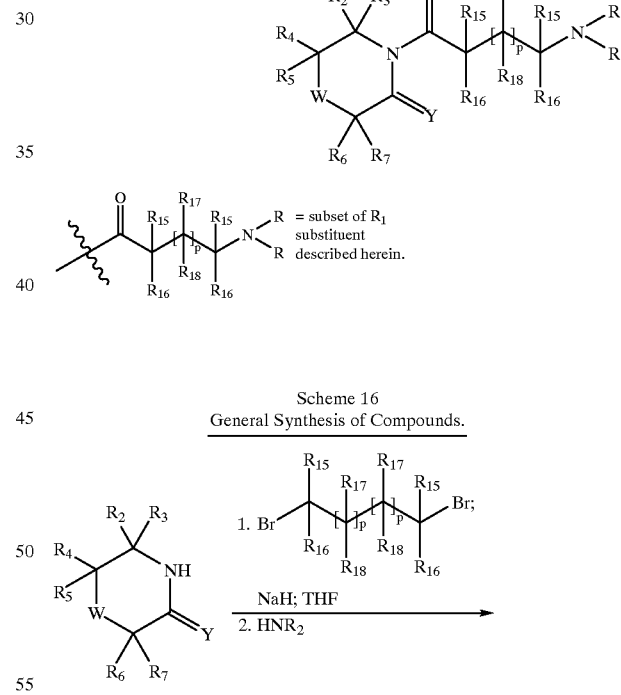

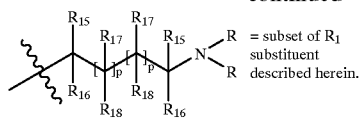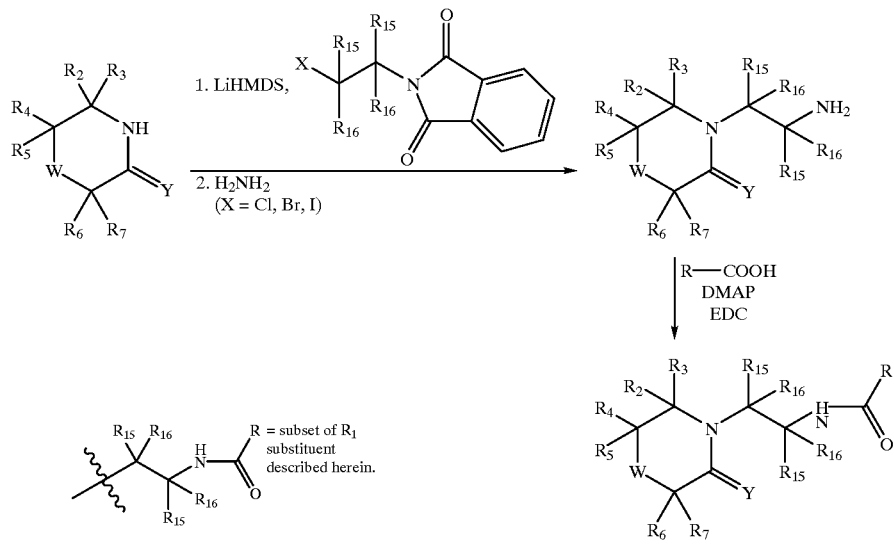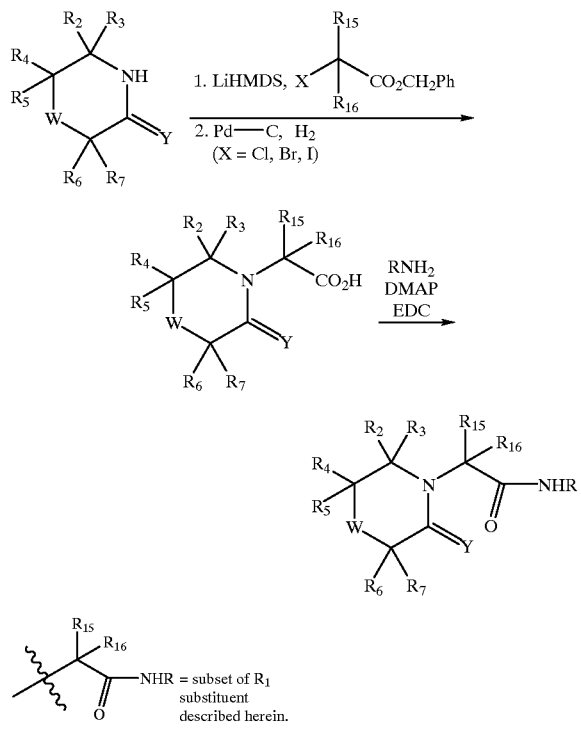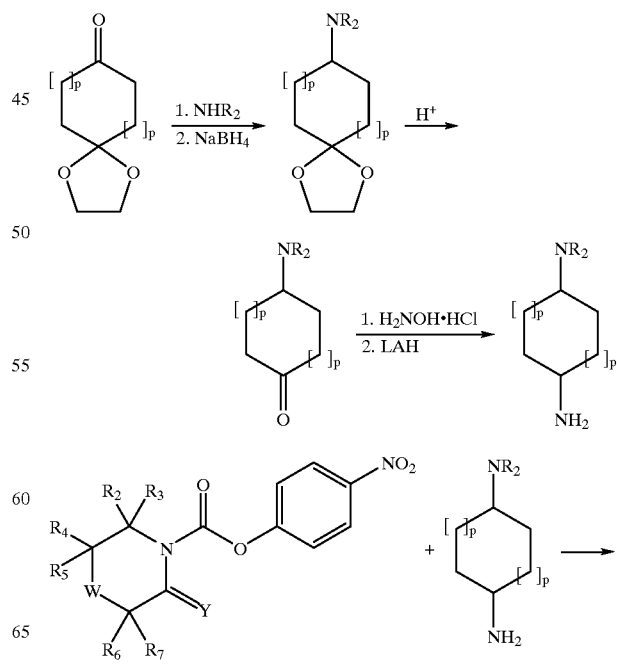

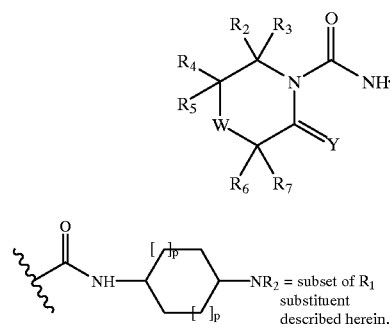
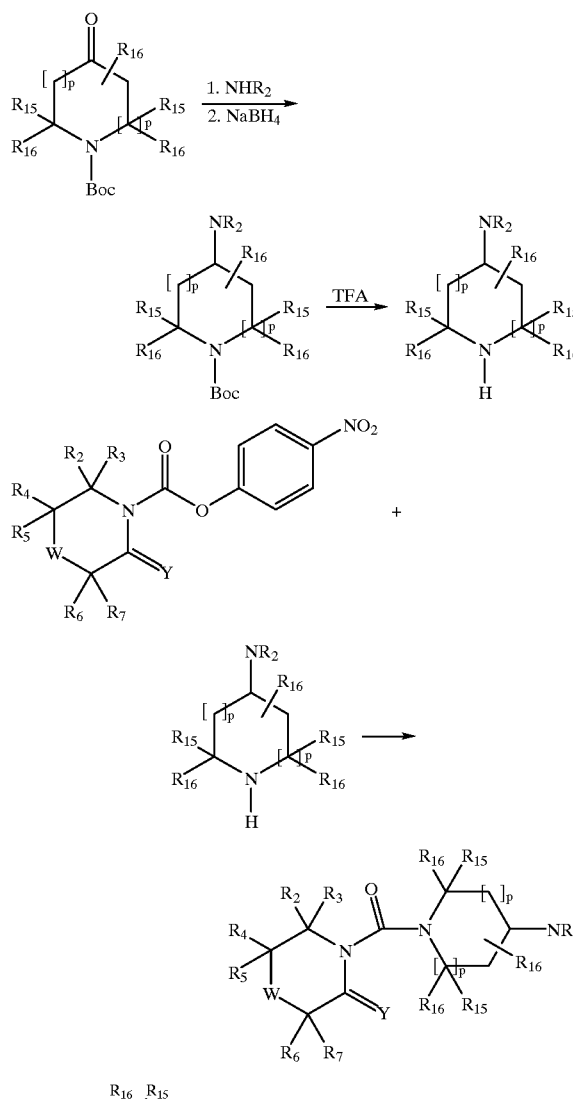
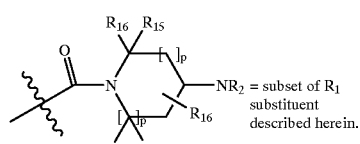
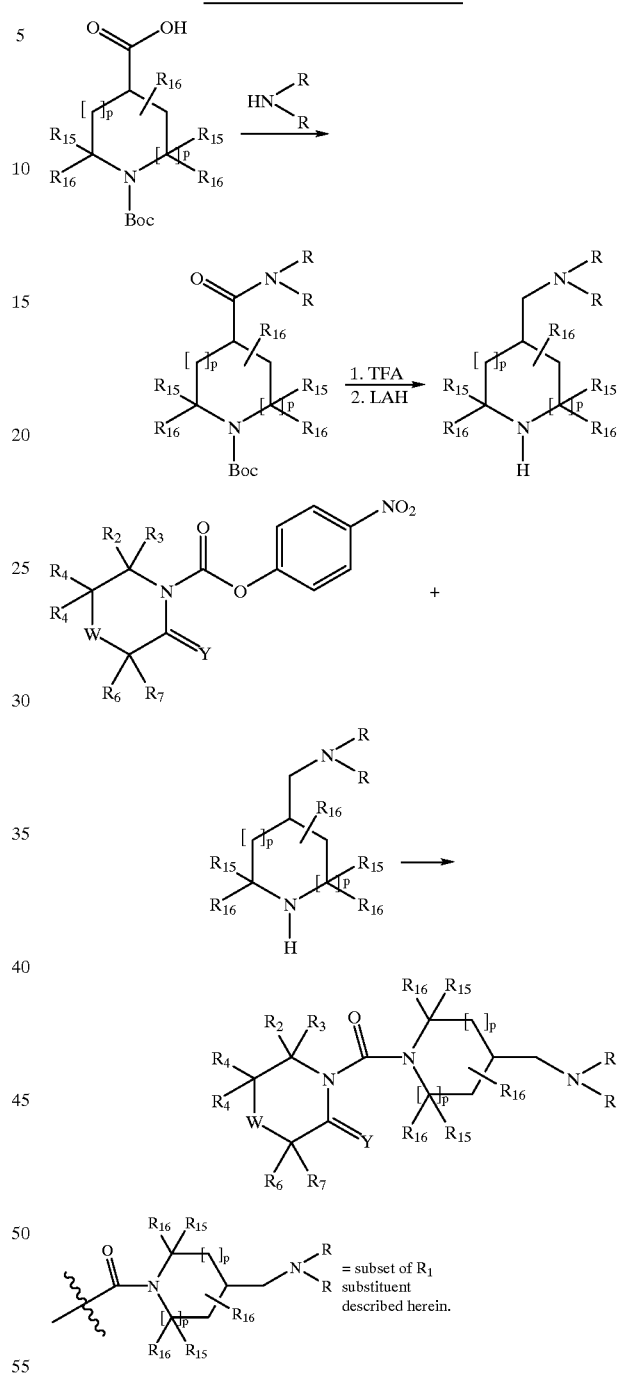
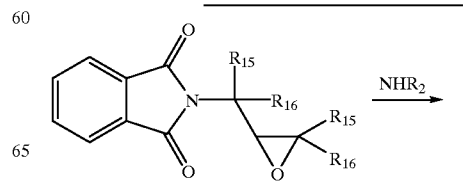

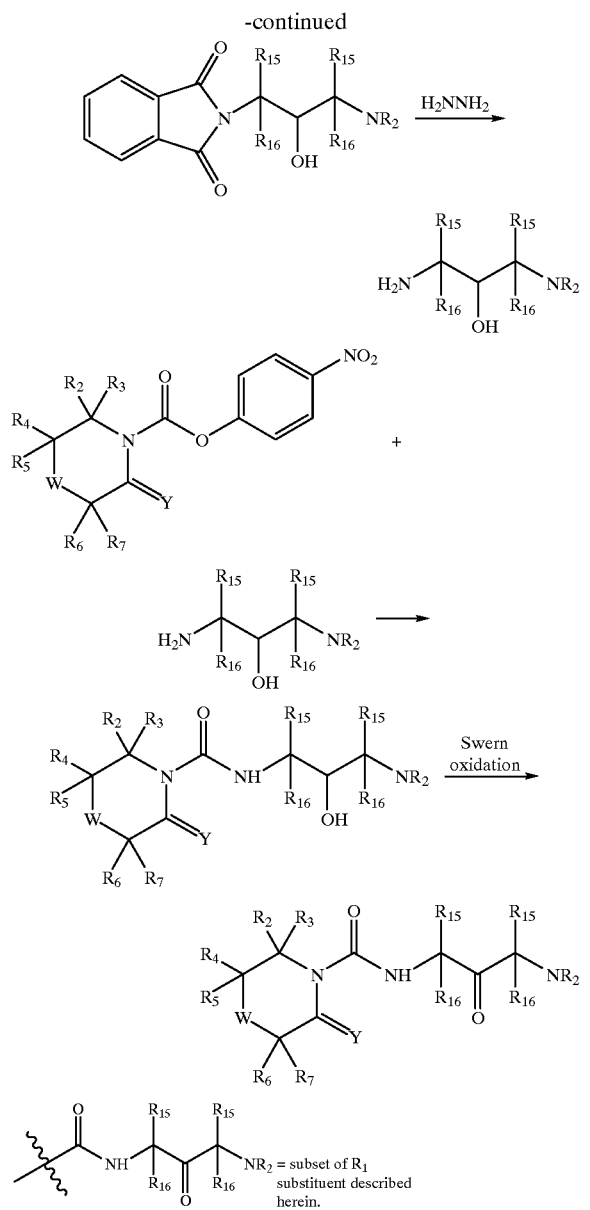

What is claimed is:
1. A compound having the structure:

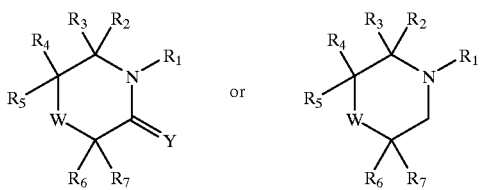

wherein W is O;
where Y is independently O or S;
where $R_2$ is aryl; wherein the aryl may be substituted with one or more of F; Cl; Br; I; —CN; —NO$_2$; —N(R$_8$)$_2$; —SO$_2$R$_8$; —(CH$_2$)$_n$C(Y)R$_8$; —(CH$_2$)$_n$YR$_8$; —(CH$_2$)$_n$C(Y)N(R$_8$)$_2$; —(CH$_2$)$_n$CO$_2$R$_8$; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl or alkynyl; C$_3$–C$_7$ cycloalkyl; or C$_5$–C$_7$ cycloalkenyl; and wherein n independently is an integer from 0 to 7 inclusive;

wherein R$_8$ is independently H, straight chained or branched C$_1$–C$_7$ alkyl, straight chained or branched C$_2$–C$_7$ alkenyl or alkynyl, C$_3$–C$_7$ cycloalkyl, or cycloalkenyl;

where R$_3$ is independently H; straight chained or branched C$_1$–C$_7$ alkyl, monofluoroalkyl, or polyfluoroalkyl;

where R$_4$ is H, —(CH$_2$)$_t$YR$_8$, —(CH$_2$)$_t$C(Y)N(R$_8$)$_2$, —(CH$_2$)$_t$C(Y)R$_8$, —(CH$_2$)$_t$CO$_2$R$_8$, —(CH$_2$)$_t$N(R$_8$)$_2$, —(CH$_2$)$_t$CN, —C(Y)R$_8$, —C(Y)N(R$_8$)$_2$, —CO$_2$R$_8$, straight chained or branched C$_1$–C$_7$ alkyl, straight chained or branched C$_2$–C$_7$ alkenyl or alkynyl, C$_3$–C$_7$ cycloalkyl, C$_5$–C$_7$ cycloalkenyl, or phenyl or benzyl; wherein the phenyl or benzyl may be substituted with one or more of F; Cl; Br; I; —CN; —NO$_2$; —N(R$_8$)$_2$; —SO$_2$R$_8$; —(CH$_2$)$_n$C(Y)R$_8$; —(CH$_2$)$_n$YR$_8$; —(CH$_2$)$_n$C(Y)N(R$_8$)$_2$; —(CH$_2$)$_n$CO$_2$R$_8$; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl or alkynyl; or C$_3$–C$_7$ cycloalkyl; or C$_5$–C$_7$ cycloalkenyl; and wherein t independently is an integer from 1 to 4 inclusive;

where R$_5$ is H, —(CH$_2$)$_t$YR$_8$, —(CH$_2$)$_t$C(Y)N(R$_8$)$_2$, —(CH$_2$)$_t$C(Y)R$_8$, —(CH$_2$)$_t$CO$_2$R$_8$, —(CH$_2$)$_t$N(R$_8$)$_2$, —(CH$_2$)$_t$CN, straight chained or branched C$_1$–C$_7$ alkyl, straight chained or branched C$_2$–C$_7$ alkenyl or alkynyl, C$_3$–C$_7$ cycloalkyl, C$_5$–C$_7$ cycloalkenyl, or phenyl or benzyl; wherein the phenyl or benzyl may be substituted with one or more of F; Cl; Br; I; —CN; —NO$_2$; —N(R$_6$)$_2$; —SO$_2$R$_8$; —(CH$_2$)$_n$C(Y)R$_8$; —(CH$_2$)$_n$YR$_8$; —(CH$_2$)$_n$C(Y)N(R$_8$)$_2$; —(CH$_2$)$_n$CO$_2$R$_8$; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl or alkynyl; C$_3$–C$_7$ cycloalkyl; or C$_5$–C$_7$ cycloalkenyl;

where R$_6$ is H, —(CH$_2$)$_t$YR$_8$, —(CH$_2$)$_t$C(Y)N(R$_8$)$_2$, —(CH$_2$)$_t$C(Y)R$_8$, —(CH$_2$)$_t$CO$_2$R$_8$, —(CH$_2$)$_t$N(R$_8$)$_2$, —(CH$_2$)$_t$CN, —C(Y)R$_8$, —C(Y)N(R$_8$)$_2$, —CO$_2$R$_8$, straight chained or branched C$_1$–C$_7$ alkyl, straight chained or branched C$_2$–C$_7$ alkenyl or alkynyl, C$_3$–C$_7$ cycloalkyl, C$_5$–C$_7$ cycloalkenyl, or phenyl or benzyl; wherein the phenyl or benzyl may be substituted with one or more of F; Cl; Br; I; —CN; —NO$_2$; —N(R$_8$)$_2$; —SO$_2$R$_8$; —(CH$_2$)$_n$C(Y)R$_8$; —(CH$_2$)$_n$YR$_8$; —(CH$_2$)$_n$C(Y)N(R$_8$)$_2$; —(CH$_2$)$_n$CO$_2$R$_8$; straight chained or branched C$_2$–C$_7$ alkyl, monofluoroalkyl, polyfluoroalkyl, aminoalkyl, or carboxamidoalkyl; straight chained or branched C$_2$–C$_7$ alkenyl or alkynyl; C$_3$–C$_7$ cycloalkyl; or C$_5$–C$_7$ cycloalkenyl;

where R$_7$ is H, —(CH$_2$)$_t$YR$_8$, —(CH$_2$)$_t$C(Y)N(R$_8$)$_2$, —(CH$_2$)$_t$C(Y)R$_8$, —(CH$_2$)$_t$CO$_2$R$_8$, —(CH$_2$)$_t$N(R$_8$)$_2$, —(CH$_2$)$_t$CN, straight chained or branched C$_1$–C$_7$ alkyl, straight chained or branched C$_2$–C$_7$ alkenyl or alkynyl, C$_3$–C$_7$ cycloalkyl, C$_5$–C$_7$ cycloalkenyl, or phenyl or benzyl; wherein the phenyl or benzyl may be substituted with one or more of F; Cl; Br; I; —CN; —NO$_2$; —N(R$_8$)$_2$; —SO$_2$R$_8$; —(CH$_2$)$_n$C(Y)R$_8$; —(CH$_2$)$_n$YR$_8$; —(CH$_2$)$_n$C(Y)N(R$_8$)$_2$; —(CH$_2$)$_n$CO$_2$R$_8$; straight chained or branched C$_1$–C$_7$ alkyl, monofluoroalkyl, polyfluoroalkyl, aminoalkyl, or carboxamidoalkyl; straight chained or branched C$_2$–C$_7$ alkenyl or alkynyl; C$_3$–C$_7$ cycloalkyl; or C$_5$–C$_7$ cycloalkenyl;

where each $R_8$, n, and t independently is as defined above; where $R_1$ is

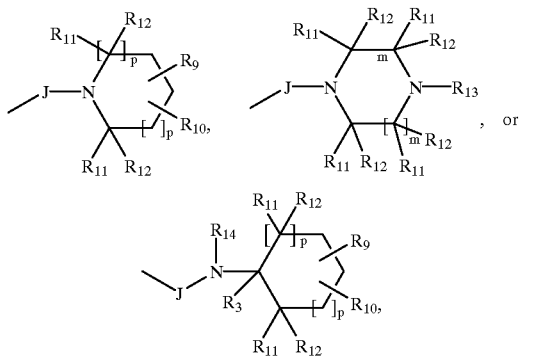

wherein each $R_9$ is H; straight chained or branched $C_1$–$C_7$ alkyl, hydroxyalkyl, aminoalkyl, alkoxyalkyl, monofluoroalkyl, or polyfluoroalkyl; straight chained or branched $C_2$–$C_7$ alkenyl or alkynyl; $C_3$–$C_7$ cycloalkyl, monofluorocycloalkyl, or polyfluorocycloalkyl; $C_5$–$C_7$ cycloalkenyl; or aryl or heteroaryl, wherein the aryl or heteroaryl may be substituted with one or more of F; Cl; Br; I; —$(CH_2)_nYR_8$; —$(CH_2)_nC(Y)R_8$; —$(CH_2)_nC(Y)N(R_8)_2$; —$(CH_2)_nCO_2R_8$; —CN; —$NO_2$; —$N(R_8)_2$; —$SO_2R_8$; straight chained or branched $C_1$–$C_7$ alkyl, monofluoroalkyl, or polyfluoroalkyl; straight chained or branched $C_2$–$C_7$ alkenyl or alkynyl; $C_3$–$C_7$ cycloalkyl, monofluorocycloalkyl, or polyfluorocycloalkyl; or $C_5$–$C_7$ cycloalkenyl;

wherein each $R_{10}$ is H; F; —OH; —$(CH_2)_nC(Y)R_8$; —$(CH_2)_nYR_8$; —$(CH_2)_nC(Y)N(R_8)_2$; —$(CH_2)_nCO_2R_8$; —CN; —$NO_2$; —$N(R_8)_2$; aryl or heteroaryl; straight chained or branched $C_1$–$C_7$ alkyl, hydroxyalkyl, aminoalkyl, carboxamidoalkyl, alkoxyalkyl, monofluoroalkyl, or polyfluoroalkyl; straight chained or branched $C_2$–$C_7$ alkenyl or alkynyl; $C_3$–$C_7$ cycloalkyl, monofluorocycloalkyl or polyfluorocycloalkyl; or $C_5$–$C_7$ cycloalkenyl; wherein the alkyl, hydroxyalkyl, alkoxyalkyl, aminoalkyl, carboxamidoalkyl, alkenyl, alkynyl, cycloalkyl or cycloalkenyl may be substituted with one or more aryl or heteroaryl; wherein the aryl or heteroaryl may be substituted with one or more of F; Cl; Br; I; —$(CH_2)_nYR_8$; —$(CH_2)_nC(Y)R_8$; —$(CH_2)_nC(Y)N(R_8)_2$; —$(CH_2)_nCOR_8$; —CN; —$NO_2$; —$N(R_8)_2$; —$SO_2R_8$; straight chained or branched $C_1$–$C_7$ alkyl, monofluoroalkyl, or polyfluoroalkyl; straight chained or branched $C_2$–$C_7$ alkenyl or alkynyl; $C_3$–$C_7$ cycloalkyl, monofluorocycloalkyl, or polyfluorocycloalkyl; or $C_5$–$C_7$ cycloalkenyl;

wherein each $R_{11}$ is independently H, —$(CH_2)_tYR_8$, —$(CH_2)_tC(Y)N(R_8)_2$, —$(CH_2)_tC(Y)R_8$, —$(CH_2)_t CO_2R_8$, —$(CH_2)_nN(R_8)_2$, —$(CH_2)_tCN$, —$C(Y)R_8$, —$C(Y)N(R_8)_2$, —$CO_2R_8$, straight chained or branched $C_1$–$C_7$ alkyl, straight chained or branched $C_2$–$C_7$ alkenyl or alkynyl, $C_3$–$C_7$ cycloalkyl, or $C_5$–$C_7$ cycloalkenyl;

wherein each $R_{12}$ is independently H, —$(CH_2)_tYR_8$, —$(CH_2)_tC(Y)N(R_8)_2$, —$(CH_2)_tC(Y)R_8$, —$(CH_2)_t CO_2R_8$, —$(CH_2)_nN(R_8)_2$, —$(CH_2)_tCN$, straight chained or branched $C_1$–$C_7$ alkyl, straight chained or branched $C_2$–$C_7$ alkenyl or alkynyl, $C_3$–$C_7$ cycloalkyl, or $C_5$–$C_7$ cycloalkenyl;

wherein $R_{13}$ is H, $C_1$–$C_7$ alkyl, —$C(O)R_2$, aryl, heteroaryl, $C_1$–$C_7$ alkyl substituted with one or two aryl, or $C_1$–$C_7$ alkyl substituted with one or two heteroaryl; wherein the aryl or heteroaryl may be substituted with one or more of F; Cl; Br; I; —CN; —$NO_2$; —$N(R_8)_2$; —$SO_2R_8$; —$(CH_2)_nC(Y)R_8$; —$(CH_2)_nYR_8$; —$(CH_2)_nC(Y)N(R_8)_2$; —$(CH_2)_nCO_2R_8$; straight chained or branched $C_1$–$C_7$ alkyl, monofluoroalkyl, polyfluoroalkyl, or carboxamidoalkyl; straight chained or branched $C_2$–$C_7$ aminoalkyl, alkenyl or alkynyl; $C_3$–$C_7$ cycloalkyl; or $C_5$–$C_7$ cycloalkenyl;

wherein $R_{14}$ is H, straight chained or branched $C_1$–$C_7$ alkyl;

wherein each m is independently 1 or 2;

wherein each p is independently an integer from 0 to 2 inclusive;

wherein J is

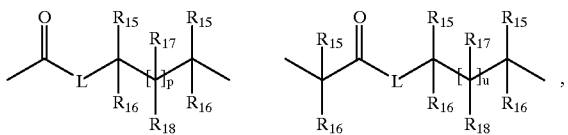

wherein each $R_{15}$ is independently H, —$(CH_2)_tYR_8$, —$(CH_2)_tC(Y)N(R_8)_2$, —$(CH_2)_tC(Y)R_8$, —$(CH_2)_t CO_2R_8$, —$(CH_2)_tN(R_8)_2$, —$(CH_2)_tCN$, —$C(Y)R_8$, —$C(Y)N(R_8)_2$, —$CO_2R_8$, straight chained or branched $C_1$–$C_7$ alkyl, straight chained or branched $C_2$–$C_7$ alkenyl or alkynyl, $C_3$–$C_7$ cycloalkyl, or $C_5$–$C_7$ cycloalkenyl;

wherein each $R_{16}$ is independently H, —$(CH_2)_tYR_8$, —$(CH_2)_tC(Y)N(R_8)_2$, —$(CH_2)_tC(Y) R_8$, —$(CH_2)_t CO_2R_8$, —$(CH_2)_tN(R_8)_2$, —$(CH_2)_tCN$, straight chained or branched $C_1$–$C_7$ alkyl, straight chained or branched $C_2$–$C_7$ alkenyl or alkynyl, $C_3$–$C_7$ cycloalkyl, or $C_5$–$C_7$ cycloalkenyl;

wherein each $R_{17}$ is independently H; F; —$(CH_2)_tYR_8$; —$(CH_2)_tC(Y)N(R_8)_2$; —$(CH_2)_tC(Y)R_8$; —$(CH_2)_t CO_2R_8$; —$(CH_2)_tN(R_8)_2$; —$(CH_2)_tCN$; —$C(Y)R_8$; —$C(Y)N(R_8)_2$; —$CO_2R_8$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

wherein each $R_{18}$ is independently H; F; —$(CH_2)_tYR_8$; —$(CH_2)_tC(Y)N(R_8)_2$; —$(CH_2)_tC(Y) R_8$; —$(CH_2)_t CO_2R_8$; —$(CH_2)_tN(R_8)_2$; —$(CH_2)_tCN$; straight chained or branched $C_1$–$C_7$ alkyl, monofluoroalkyl, polyfluoroalkyl, aminoalkyl, or carboxamidoalkyl; straight chained or branched $C_2$–$C_7$ alkenyl or alkynyl; $C_3$–$C_7$ cycloalkyl; or $C_5$–$C_7$ cycloalkenyl;

wherein L is S, O, or $N(R_8)$;

or a pharmaceutically acceptable salt thereof.

2. The compound of claim 1, wherein the compound comprises the (+) enantiomer.

3. The compound of claim 1, wherein the compound comprises the (−) enantiomer.

4. The compound of claim 1, wherein $R_9$ is aryl or heteroaryl, wherein the aryl or heteroaryl may be substituted with one or more of F; Cl; Br; I; —$(CH_2)_nYR_8$; —$(CH_2)_nC(Y)R_8$; —$(CH_2)_nC(Y)N(R_8)_2$; —$(CH_2)_nCO_2R_8$; —CN; —$NO_2$; —$N(R_8)_2$; —$SO_2R_8$; straight chained or branched $C_1$–$C_7$ alkyl, monofluoroalkyl, or polyfluoroalkyl; and wherein $R_{10}$ is H; —CN; —OH; —$CO_2R_8$; aryl or heteroaryl; wherein the aryl or heteroaryl may be substituted with one or more of F; Cl; Br; I; —$(CH_2)_nYR_8$; —$(CH_2)_nC(Y)R_8$; —$(CH_2)_nC(Y)N(R_8)_2$; —$(CH_2)_nCO_2R_8$; —CN; —$NO_2$; —$N(R_8)_2$; —$SO_2R_8$; straight chained or branched $C_1$–$C_7$ alkyl, monofluoroalkyl, or polyfluoroalkyl.

5. The compound of claim 4 having the structure:

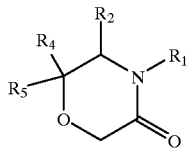

wherein $R_2$ is phenyl; wherein the phenyl may be substituted with one or more of F; Cl; Br; I; —CN; —$NO_2$; —$N(R_8)_2$; —$SO_2R_8$; —$(CH_2)_nC(Y)R_8$; —$(CH_2)_nYR_8$; —$(CH_2)_nC(Y)N(R_8)_2$; —$(CH_2)_nCO_2R_8$; straight chained or branched $C_1$–$C_7$ alkyl, monofluoroalkyl, or polyfluoroalkyl.

6. The compound of claim 5 wherein J is

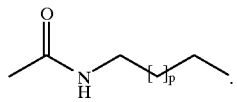

7. The compound of claim 6 wherein $R_1$ is

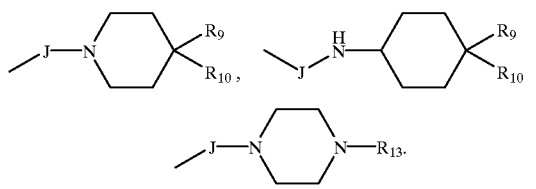

8. The compound of claim 7,
wherein $R_9$ is phenyl or pyridyl, wherein the phenyl or pyridyl may be substituted with one or more of F; Cl; Br; I; —$(CH_2)_nYR_8$; —$(CH_2)_nC(Y)R_8$; —$(CH_2)_nC(Y)N(R_8)_2$; —$(CH_2)_nCO_2R_8$; —CN; —$NO_2$; —$N(R_8)_2$; —$SO_2R_8$; straight chained or branched $C_1$–$C_7$ alkyl, monofluoroalkyl, or polyfluoroalkyl;
wherein $R_{10}$ is H, —CN, —OH, —$CO_2R_8$, or phenyl; wherein the phenyl may be substituted with one or more of F; Cl; Br; I; —$(CH_2)_nYR_8$; —$(CH_2)_nC(Y)R_8$; —$(CH_2)_nC(Y)N(R_8)_2$; —$(CH_2)_nCO_2R_8$; —CN; —$NO_2$; —$N(R_8)_2$; —$SO_2R_8$; straight chained or branched $C_1$–$C_7$ alkyl, monofluoroalkyl, or polyfluoroalkyl; and
wherein $R_{13}$ is phenyl; wherein the phenyl may be substituted with one or more of F; Cl; Br; I; —CN; —$NO_2$; —$N(R_8)_2$; —$SO_2R_8$; —$(CH_2)_nC(Y)R_8$; —$(CH_2)_nYR_8$; —$(CH_2)_nC(Y)N(R_8)_2$; —$(CH_2)_nCOR_8$; straight chained or branched $C_1$–$C_7$ alkyl, monofluoroalkyl, polyfluoroalkyl, or carboxamidoalkyl; straight chained or branched $C_2$–$C_7$ aminoalkyl, alkenyl, or alkynyl; $C_3$–$C_7$ cycloalkyl; or $C_5$–$C_7$ cycloalkenyl.

9. A pharmaceutical composition comprising a therapeutically effective amount of the compound of claim 1 and a pharmaceutically acceptable carrier.

10. The pharmaceutical composition of claim 9, wherein the amount of the compound is an amount from about 0.01 mg to about 800 mg.

11. The pharmaceutical composition of claim 10, wherein the amount of the compound is from about 0.01 mg to about 500 mg.

12. The pharmaceutical composition of claim 11, wherein the amount of the compound is from about 0.01 mg to about 250 mg.

13. The pharmaceutical composition of claim 12, wherein the amount of the compound is from about 0.1 mg to about 60 mg.

14. The pharmaceutical composition of claim 13, wherein the amount of the compound is from about 1 mg to about 20 mg.

15. The pharmaceutical composition of claim 9, wherein the carrier is a liquid and the composition is a solution.

16. The pharmaceutical composition of claim 9, wherein the carrier is a solid and the composition is a tablet.

17. The pharmaceutical composition of claim 9, wherein the carrier is a gel and the composition is a suppository.

18. The pharmaceutical composition of claim 9, wherein the compound additionally does not cause a fall in blood pressure at dosages effective to alleviate benign prostatic hyperplasia.

19. A method of treating a subject suffering from benign prostatic hyperplasia which comprises administering to the subject an amount of the compound of claim 1 effective to treat benign prostatic hyperplasia.

20. A method of claim 19, wherein the compound additionally does not cause a fall in blood pressure at dosages effective to alleviate benign prostatic hyperplasia.

21. The method of claim 20, wherein the compound effects treatment of benign prostatic hyperplasia by relaxing lower urinary tract tissue.

22. The method of claim 21, wherein lower urinary tract tissue is prostatic smooth muscle.

23. A method of treating a subject suffering from high intraocular pressure which comprises administering to the subject an amount of the compound of claim 1 effective to lower intraocular pressure.

24. A method of treating a subject suffering from a disorder associated with high cholesterol which comprises administering to the subject an amount of the compound of claim 1 effective to inhibit cholesterol synthesis.

25. A method of treating a subject suffering from cardiac arrhythmia which comprises administering to the subject an amount of the compound of claim 1 effective to treat cardiac arrhythmia.

26. A method of treating a subject suffering from impotency which comprises administering to the subject an amount of the compound of claim 1 effective to treat impotency.

27. A method of treating a subject suffering from sympathetically mediated pain which comprises administering to the subject an amount of the compound of claim 1 effective to treat sympathetically mediated pain.

28. A method of treating a subject suffering from migraine which comprises administering to the subject an amount of the compound of claim 1 effective to treat migraine.

29. A method of treating a disease which is susceptible to treatment by antagonism of the $\alpha_{1a}$ receptor which comprises administering to the subject an amount of the compound of claim 1 effective to treat the disease.

30. A method of treating a subject suffering from benign prostatic hyperplasia which comprises administering to the subject an amount of the compound of claim 1 in combination with a 5-alpha reductase inhibitor effective to treat benign prostatic hyperplasia.

31. The method of claim 30, wherein the 5-alpha reductase inhibitor is finasteride.

32. A pharmaceutical composition comprising a therapeutically effective amount of the compound of claim 1 in combination with a therapeutically effective amount of finasteride and a pharmaceutically acceptable carrier.

33. The pharmaceutical composition of claim 32, wherein the compound is present in an amount from about 0.01 mg to about 800 mg and the therapeutically effective amount of the finasteride is about 5 mg.

34. The pharmaceutical composition of claim 33, wherein the compound is present in an amount from about 0.1 mg to about 60 mg and the therapeutically effective amount of finasteride is about 5 mg.

35. The pharmaceutical composition of claim 34, wherein the compound is present in an amount from about 1 mg to about 20 mg and the therapeutically effective amount of finasteride is about 5 mg.

36. A method of relaxing lower urinary tract tissue which comprises contacting the lower urinary tract tissue with an amount of the compound of claim 1 effective to relax lower urinary tract tissue.

37. The method of claim 36, wherein the lower urinary tract tissue is prostatic smooth muscle.

38. A method of relaxing lower urinary tract tissue in a subject which comprises administering to the subject an amount of the compound of claim 1 effective to relax lower urinary tract tissue.

39. The method of claim 38, wherein the lower urinary tract tissue is prostatic smooth muscle.

40. A pharmaceutical composition made by combining a therapeutically effective amount of the compound of claim 1 and a pharmaceutically acceptable carrier.

41. A pharmaceutical composition made by combining a therapeutically effective amount of the compound of claim 1 with a therapeutically effective amount of finasteride and a pharmaceutically acceptable carrier.

42. A process for making a pharmaceutical composition comprising combining a therapeutically effective amount of the compound of claim 1 and a pharmaceutically acceptable carrier.

43. A process for making a pharmaceutical composition comprising combining a therapeutically effective amount of the compound of claim 1 with a therapeutically effective amount of finasteride and a pharmaceutically acceptable carrier.

* * * * *

UNITED STATES PATENT AND TRADEMARK OFFICE
CERTIFICATE OF CORRECTION

PATENT NO.   : 6,218,390 B1
DATED        : April 17, 2001
INVENTOR(S)  : Bharat Lagu et al.

It is certified that error appears in the above-identified patent and that said Letters Patent is hereby corrected as shown below:

Column 66,
Line 35, "$N(R_6)_2$" should read -- $N(R_8)_2$ --
Line 51, "branched $C_2$-$C_7$ alkyl" should read -- branched $C_1$-$C_7$ alkyl --

Column 67,
Lines 4-10, the structure shown as

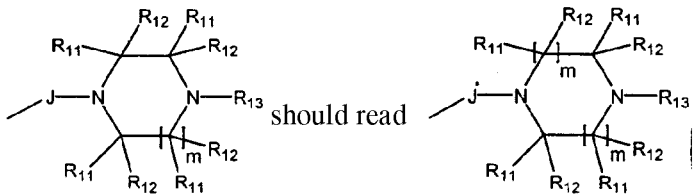 should read 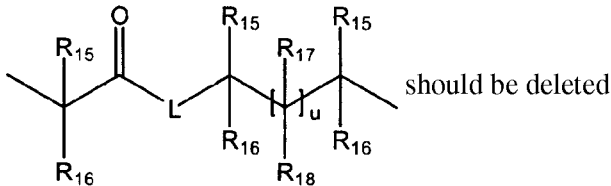

Line 49, "$(CH_2)_nCOR_8$" should read -- $(CH_2)_nCO_2R_8$ --
Line 56, "$(CH)_tC(Y)N(R_8)_2$" should read -- $(CH_2)_tC(Y)N(R_8)_2$ --

Column 68,
Lines 20-24, the structure shown as should be deleted

Line 36, "$CH_2)_tN(R_8)_2$" should read -- $(CH_2)_tN(R_8)_2$ --

UNITED STATES PATENT AND TRADEMARK OFFICE
CERTIFICATE OF CORRECTION

PATENT NO. : 6,218,390 B1
DATED : April 17, 2001
INVENTOR(S) : Bharat Lagu et al.

It is certified that error appears in the above-identified patent and that said Letters Patent is hereby corrected as shown below:

Column 69,
Line 57, "$(CH_2)_nCOR_8$" should read -- $(CH_2)_nCO_2R_8$ --

Signed and Sealed this

Eighteenth Day of March, 2003

JAMES E. ROGAN
*Director of the United States Patent and Trademark Office*